US012797459B2

(12) United States Patent
Lee et al.

(10) Patent No.: US 12,797,459 B2
(45) Date of Patent: Nov. 17, 2026

(54) RECOMBINANT FOOT-AND-MOUTH DISEASE TYPE A VIRUS INDUCING STRONG ADAPTIVE IMMUNE RESPONSE AND OVERCOMING INTERFERENCE FROM MATERNALLY-DERIVED ANTIBODIES, AND FOOT-AND-MOUTH DISEASE VACCINE COMPOSITION COMPRISING SAME

(71) Applicant: REPUBLIC OF KOREA(ANIMAL AND PLANT QUARANTINE AGENCY), Gimcheon-si (KR)

(72) Inventors: Min Ja Lee, Gimcheon-si (KR); Hyun Mi Kim, Gimcheon-si (KR); Sehee Shin, Gimcheon-si (KR); Su-Mi Kim, Daejeon (KR); Jong-Hyeon Park, Gimcheon-si (KR)

(73) Assignee: REPUBLIC OF KOREA(ANIMAL AND PLANT QUARANTINE AGENCY), Gimcheon-si (KR)

( * ) Notice: Subject to any disclaimer, the term of this patent is extended or adjusted under 35 U.S.C. 154(b) by 336 days.

(21) Appl. No.: 18/710,511

(22) PCT Filed: Nov. 11, 2022

(86) PCT No.: PCT/KR2022/017807
§ 371 (c)(1),
(2) Date: May 15, 2024

(87) PCT Pub. No.: WO2023/090772
PCT Pub. Date: May 25, 2023

(65) Prior Publication Data

US 2026/0166137 A1 Jun. 18, 2026

(30) Foreign Application Priority Data

Nov. 17, 2021 (KR) ........................ 10-2021-0158591
Nov. 17, 2021 (KR) ........................ 10-2021-0158592

(51) Int. Cl.

| | |
|---|---|
| ***A61K 39/135*** | (2006.01) |
| ***A61P 31/14*** | (2006.01) |
| ***A61P 37/04*** | (2006.01) |
| ***C12N 7/00*** | (2006.01) |
| ***C12N 15/85*** | (2006.01) |
| ***G01N 33/569*** | (2006.01) |
| *A61K 39/00* | (2006.01) |

(52) U.S. Cl.
CPC ............ *A61K 39/135* (2013.01); *A61P 31/14* (2018.01); *A61P 37/04* (2018.01); *C12N 7/00* (2013.01); *C12N 15/85* (2013.01); *G01N 33/56983* (2013.01); *A61K 2039/525* (2013.01); *A61K 2039/55* (2013.01); *A61K 2039/572* (2013.01); *A61K 2039/575* (2013.01); *C12N 2770/32122* (2013.01); *C12N 2770/32134* (2013.01); *C12N 2770/32171* (2013.01); *G01N 2333/09* (2013.01)

(58) Field of Classification Search
CPC .................. A61K 39/135; A61K 39/12; C12N 2770/32134; C07K 14/005; G01N 2333/09
See application file for complete search history.

(56) References Cited

U.S. PATENT DOCUMENTS

| | | | |
|---|---|---|---|
| 10,973,908 | B1 | 4/2021 | Bermudes |
| 2014/0219918 | A1 | 8/2014 | Seago et al. |
| 2019/0134183 | A1 | 5/2019 | Widener et al. |

FOREIGN PATENT DOCUMENTS

| | | | |
|---|---|---|---|
| CN | 110317278 | A | 10/2019 |
| JP | H10-509723 | A | 9/1998 |
| KR | 10-2015-0014015 | A | 2/2015 |
| KR | 10-2020-0134637 | A | 12/2020 |
| KR | 10-2234754 | B1 | 4/2021 |
| KR | 10-2269272 | B1 | 6/2021 |

OTHER PUBLICATIONS

None Cited.*
International Search Report issued in PCT/KR2022/017801, mailed Feb. 22, 2023.
International Search Report issued in PCT/KR2022/017807, mailed Feb. 21, 2023.
Fan, H. et al. "Immunization of DNA vaccine encoding C3d-VP1 fusion enhanced protective immune response against foot-and-mouth disease virus," Virus Genes 35:347-357 (2007).
Lee, S. Y. et al. "Rapid engineering of foot-and-mouth disease vaccine and challenge viruses," J. Virol. 91:e00155-17 (2017).
Lee, M. J. et al. "Advanced foot-and-mouth disease vaccine platform for stimulation of simultaneous cellular and humoral immune responses," Vaccines (Basel) 8:254 (2020).
Lee, M. J. et al. "The C3d-fused foot-and-mouth disease vaccine platform overcomes maternally-derived antibody interference by inducing a potent adaptive immunity," NPJ Vaccines 7:70 (Jun. 28, 2022).

(Continued)

*Primary Examiner* — Barry A Chestnut
(74) *Attorney, Agent, or Firm* — MEDLER FERRO WOODHOUSE & MILLS PLLC

(57) ABSTRACT

Proposed are a foot-and-mouth disease vaccine composition including recombinant foot-and-mouth disease viruses and an antigen isolated and purified from the viruses. In the early stages of vaccination, a humoral immune response is simultaneously induced through the induction of a robust cellular immune response, while in the presence of maternally-derived antibodies (MDAs), B cell receptors are stimulated. Through this, it is possible to provide the vaccine composition that enables active immunity and overcomes the interference of the maternally-derived antibodies and to provide a method of preventing or treating foot-and-mouth diseases using the same composition.

5 Claims, 19 Drawing Sheets

Specification includes a Sequence Listing.

(56) References Cited

OTHER PUBLICATIONS

NCBI. GenBank Accession No. AY593823.1. Foot-and-mouth disease virus O isolate o1manisa iso87, complete genome. Apr. 28, 2005.

NCBI. GenBank Accession No. XM_034935877.1. Jun. 5, 2020.

Park, Jong-Hyun. "Development of Next-Generation 'Immunity-Enhancing Foot-and-Mouth Disease Vaccine Antigen Platform'," Press Information. Jun. 27, 2022.

Sicard et al., "B cell targeting by molecular adjuvants for enhanced immunogenicity," Expert Rev. Vaccines 19(11):1023-1039 (2020).

De Groot et al., "C3d adjuvant effects are mediated through the activation of C3d-specific autoreactive T cells," Immunol Cell Biol. 93(2):189-197 (2015).

Jo et al., "The HSP70-fused foot-and-mouth disease epitope elicits cellular and humoral immunity and drives broad-spectrum protective efficacy," NPJ Vaccines 6:42 (2021).

Knopf et al., "Novel function of complement C3d as an autologous helper T-cell target," Immunol Cell Biol. 86:221-225 (2008).

Li et al., "Virus-like particles of recombinant PCV2b carrying FMDV-VP1 epitopes induce both anti-PCV and anti-FMDV antibody responses," Appl Microbiol Biotechnol. 102:10541-10550 (2018).

* cited by examiner

RECOMBINANT FOOT-AND-MOUTH DISEASE TYPE A VIRUS INDUCING STRONG ADAPTIVE IMMUNE RESPONSE AND OVERCOMING INTERFERENCE FROM MATERNALLY-DERIVED ANTIBODIES, AND FOOT-AND-MOUTH DISEASE VACCINE COMPOSITION COMPRISING SAME

TECHNICAL FIELD

The present disclosure, to overcome the interference of maternally-derived antibodies by inducing a strong adaptive (cellular and humoral) immune response, relates to an immune-boosting recombinant foot-and-mouth disease virus with the 'C3d gene (B cell epitope)' inserted into a foot-and-mouth disease vaccine strain type A, a method of isolating and purifying inactivated antigens of the foot-and-mouth disease virus with increased immunogenicity, and use of a foot-and-mouth disease vaccine composition for overcoming the interference of maternally-derived antibodies (MDAs).

BACKGROUND ART

Foot-and-mouth disease (FMD) vaccination is required to be regular and repeated in both cattle and pigs. This vaccination induces the production of antibodies in the mother thereof. These antibodies are transferred to calves or piglets in the form of maternally-derived antibodies through the placenta or ingestion of colostrum, inducing the formation of passive immunity. These maternally-derived antibodies show host defense effects in calves and piglets during early foot-and-mouth disease virus infection. However, the MDAs have a short-term protective effect and when young animals are inoculated with foot-and-mouth disease vaccine early, the maternally-derived antibodies cause interference by passive immunity (inhibiting antigen-specific antibody production from plasma cells and memory B cells, resulting in an immunological tolerance mechanism). Therefore, the maternally-derived antibodies have negative effects of inhibiting the efficacy of vaccines and suppressing the formation of active immunity. Current foot-and-mouth disease vaccination programs recommend that calves and piglets be vaccinated after the age of 2 months when maternally-derived antibody levels decrease.

Because the level, titer, and half-life of maternally-derived antibodies vary depending on the individual, it is difficult to determine the appropriate timing for foot-and-mouth disease vaccination in the field. In addition, commercially used foot-and-mouth disease vaccines generally have a limitation in that the current vaccines are difficult to overcome the interference of maternally-derived antibodies, thereby the maternally-derived antibodies inhibit the formation of active immunity through vaccination.

Meanwhile, foot-and-mouth disease viruses (FMD viruses or FMDVs) belong to the Aphthovirus genus (Family: Picornaviridae) and are classified into seven serotypes: O, A, C, Asia1, SAT1, SAT2, and SAT3. Viruses that share more than 85% nucleotide identity to the FMDVs' genome region corresponding to the VP1 protein are mono-serotype viruses. These viruses are generally found in geographically limited regions and are classified by topotype. The FMDVs show high genetic and antigenic variation, so antibodies induced by one serotype cannot neutralize other serotypes, so there is no cross-protection upon vaccination. Nevertheless, vaccination is widely used to prevent and control the disease in countries prone to foot-and-mouth disease.

B cell activation pathways are broadly divided into three categories: 1) T cell-dependent pathway, 2) T cell-independent pathway type I, and 3) T cell-independent pathway type II. Among these, the T cell-dependent pathway is a typical pathway in which B cells are activated through TCR/MHC and CD40L/CD40. The T cell-independent pathway type I is known to be a rare pathway in the host where pathogen-associated molecular patterns (PAMPs) stimulate pattern-recognition receptors (PRRs) to directly activate B cells. Lastly, the T cell-independent pathway type II is a pathway that activates B cells by stimulating the B cell receptors CD21, CD19, and CD81 with antigens or B cell epitopes such as C3d. When maternally-derived antibodies are present in the host, immune tolerance and tolerance mechanisms occur. As a result, presenting antigens to T cells, inducing cellular immune responses, and activating B cells through T cell-dependent pathways are difficult. Therefore, it is necessary to directly activate B cells through a T cell-independent pathway or continuously stimulate T cells by inducing a robust cellular immune response.

Therefore, the present disclosure seeks to overcome the interference phenomenon of the maternally-derived antibodies, which has been pointed out as a major limitation of foot-and-mouth disease vaccines currently available on the market. To overcome the interference of the maternally-derived antibodies by stimulating receptors on the surface of B cells through C3d, which is a B cell epitope, the active site of C3d was selected as a candidate substance and inserted into the O PA2 P1 backbone (VP1 site). Thus, a foot-and-mouth disease vaccine strain of FMDV type O for overcoming interference of the maternally-derived antibodies was developed. In addition, immune-boosting antigens isolated and purified from this vaccine strain and a foot-and-mouth disease vaccine composition including the same for overcoming interference of the maternally-derived antibodies were developed.

REFERENCES

Patent Document

Korean Registered Patent Gazette No. 10-2234754

Non-Patent Document

Lee, S. Y. et al. Rapid engineering of foot-and-mouth disease vaccine and challenge viruses. *J. Virol.* 91, e00155-00117 (2017).

Lee, M. J. et al. Advanced foot-and-mouth disease vaccine platform for stimulation of simultaneous cellular and humoral immune responses. *Vaccines* (*Basel*) 8, 254 (2020).

SUMMARY OF INVENTION

Technical Problem

Against the background, to overcome the interference phenomenon of maternally-derived antibodies, which is a limitation of the foot-and-mouth disease vaccines currently available on the market, the present disclosure is focused on directly stimulating receptors on the surface of B cells through C3d, which is a B cell epitope to overcome the interference of the maternally-derived antibodies.

To overcome the difficulty in inducing foot-and-mouth disease vaccine-mediated immune responses due to the interference phenomenon of the maternally-derived antibodies, which has been pointed out as a limitation of the foot-and-mouth disease vaccines currently available on the market, the objective of the present disclosure is to provide an immune-boosting recombinant foot-and-mouth disease virus with the 'C3d gene (B cell epitope)' inserted into the foot-and-mouth disease vaccine strain type A, a foot-and-mouth disease vaccine composition including antigens isolated and purified from the virus, and a method of producing the recombinant foot-and-mouth disease virus.

Technical Solution

To achieve the objective, the present disclosure is to provide recombinant foot-and-mouth disease viruses and a foot-and-mouth disease vaccine composition including antigens isolated and purified from the recombinant foot-and-mouth disease viruses.

In addition, the present disclosure is to provide a method of producing the recombinant foot-and-mouth disease viruses and a method of isolating and purifying antigens from the recombinant foot-and-mouth disease viruses.

According to the present disclosure, the recombinant foot-and-mouth disease viruses can be produced using a recombinant plasmid into which foot-and-mouth disease virus genes are inserted. The recombinant foot-and-mouth disease viruses may be but are not limited to, foot-and-mouth disease virus type O or type A.

The recombinant foot-and-mouth disease virus type O can be produced using a recombinant plasmid represented by SEQ ID NO: 8. The recombinant foot-and-mouth disease virus type A can be produced using a recombinant plasmid represented by SEQ ID NO: 11.

To produce the recombinant foot-and-mouth disease viruses, an active site (13 a.a) of C3d was selected as a candidate substance to be inserted into a backbone. The active site of C3d is represented by SEQ ID NO: 4 (the base sequence encoding the active site of C3d is represented by SEQ ID NO: 5).

By inserting the sequence of the active site of C3d into O PA2 or A22 P1 backbone (VP1 site), a foot-and-mouth disease vaccine composition such as O PA2-C3d of FMDV type O and A22-C3d of FMDV type A is provided to overcome the interference of maternally-derived antibodies.

In addition, the present disclosure is to provide immune-boosting antigens isolated and purified from the recombinant viruses and a foot-and-mouth disease vaccine composition including the antigens for overcoming the interference of maternally-derived antibodies.

In addition, the present disclosure is to provide a method of preventing or treating foot-and-mouth disease by using the vaccine composition including the recombinant foot-and-mouth disease viruses or antigens isolated and purified from the recombinant foot-and-mouth disease viruses.

In addition, the present disclosure is to provide a foot-and-mouth disease diagnostic kit or foot-and-mouth disease diagnostic kit composition including the recombinant foot-and-mouth disease viruses or the antigens of the recombinant foot-and-mouth disease viruses.

In addition, the present disclosure is to provide a method of diagnosing foot-and-mouth disease by using the foot-and-mouth disease diagnostic kit or foot-and-mouth disease diagnostic kit composition.

The recombinant foot-and-mouth disease viruses of the present disclosure are based on virus type O or virus type A.

The virus type O is not limited but may be 01-Manisa in one embodiment of the present disclosure.

The virus type A is not limited but may be subtype A22 in one embodiment of the present disclosure, and preferably may be A22/Iraq/24/64.

In the present disclosure, the term 'plasmid' refers to a DNA molecule containing a DNA sequence linked to be operable to suitable regulatory sequences capable of expressing the DNA in a suitable host. Once transformed into a suitable host, the plasmid can replicate and function independently of the host genome, or in some cases can be integrated into the genome itself. Since a plasmid is currently the most commonly used form of a vector, 'plasmid' and 'vector' are sometimes used interchangeably in the context of the present disclosure.

For the objective of the present disclosure, it is preferred to use a plasmid vector. Typical plasmid vectors that can be used for this objective have the following sites in their structures: (a) a replication origin that allows efficient replication to include hundreds of plasmid vectors per host cell, (b) a selection marker that allows host cells transformed with plasmid vectors to be selected, and (c) a restriction enzyme cutting site where foreign DNA fragments can be inserted. Even when an appropriate restriction enzyme cutting site does not exist, vectors and foreign DNAs can be easily ligated using synthetic oligonucleotide adapters or linkers according to conventional methods.

The recombinant vector and recombinant foot-and-mouth disease viruses of the present disclosure can be produced by conventional genetic manipulation and transformation methods. Appropriate amounts of viruses can be obtained by continuously subculturing viruses made in small quantities.

The cells may be derived from one or more types of cells selected from the group consisting of canines, felines, boars, bovines, deer, giraffes, peccaries, camelids, hippopotamuses, equines, tapirs, rhinoceroses, weasels, leporids, rodents, and primates. Preferably, the cells for use may be derived from one or more types selected from the group consisting of goat tongue cells (ZZ-R) and hamster kidney cells (BHK-21), black goat kidney cells (BGK), porcine kidney cells (IBRS-2), and bovine kidney cells (LFBK).

The foot-and-mouth disease vaccine composition of the present disclosure includes the recombinant foot-and-mouth disease viruses of the present disclosure or antigens isolated and purified from the recombinant viruses as an active ingredient.

The recombinant foot-and-mouth disease viruses included in the foot-and-mouth disease vaccine composition, foot-and-mouth disease diagnostic kit, and foot-and-mouth disease diagnostic kit composition of the present disclosure may be a recombinant foot-and-mouth disease virus type O or type A, respectively, or a combination thereof.

In addition, the antigens isolated and purified from the recombinant foot-and-mouth disease viruses included in the foot-and-mouth disease vaccine composition, foot-and-mouth disease diagnostic kit, and foot-and-mouth disease diagnostic kit composition of the present disclosure may be ones derived from a recombinant foot-and-mouth disease virus type O or type A, respectively, or a combination thereof.

A vaccine including the vaccine composition may be a live vaccine, an attenuated vaccine, or a killed vaccine.

The vaccine composition including the recombinant foot-and-mouth disease viruses or antigens isolated and purified from the recombinant viruses can be administered at a dose in a range of 1/640 to 1/10 dose, preferably 1/40 to 1/10 dose.

The vaccine composition can be administered to artiodactyls such as pigs, sheep, goats, deer, and wild ruminants, excluding humans.

In addition, the vaccine composition may additionally include diluents or excipients such as carriers, fillers, extenders, binders, wetting agents, disintegrants, and surfactants commonly acceptable in the art.

Additionally, the vaccine composition may be administered (or injected) to the individual in various forms. Administration may be performed by any one method selected from the group consisting of subcutaneous injection, intramuscular injection, subcutaneous injection, intraperitoneal injection, nasal administration, oral administration, transdermal administration, or oral administration.

Advantageous Effects

The present disclosure relates to recombinant foot-and-mouth disease viruses and a foot-and-mouth disease vaccine composition including antigens isolated and purified from the recombinant foot-and-mouth disease viruses. The present disclosure can provide a vaccine composition that overcomes the interference of MDAs and enables active immunity by simultaneously inducing a humoral immune response through the induction of a robust cellular immune response in the early stage of vaccination and stimulating B cell receptors in the presence of MDAs.

MODE FOR CARRYING OUT INVENTION

Figure 1A:
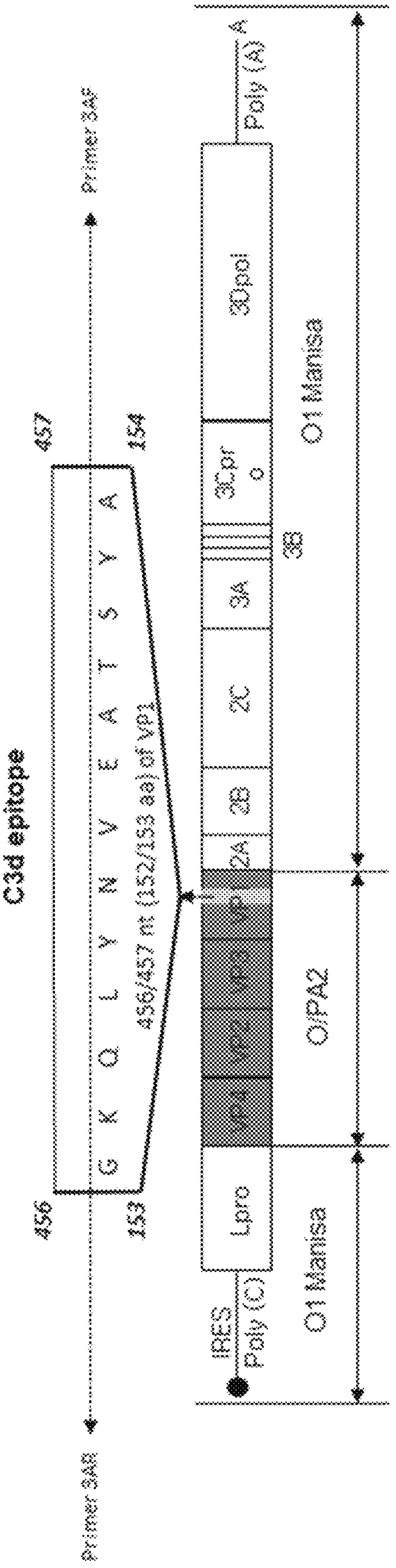
FIG. 1*a* shows a genetic schematic diagram of a recombinant immune-boosting foot-and-mouth disease virus type O according to the present disclosure.

Hereinafter, the present disclosure will be described in detail through examples and experimental examples.

However, the following examples and experimental examples only illustrate the present disclosure and the content of the present disclosure is not limited to the following examples and experimental examples.

Materials and Methods

1. Recombinant Plasmid Preparation

A recombinant plasmid was prepared as described by Lee et al. (Lee, S. Y. et al. Rapid engineering of foot-and-mouth disease vaccine and challenge viruses. *J. Virol.* 91, e00155-00117 (2017).) The entire FMD-01-Manisa virus genome (GenBank Accession No. AY593823.1) was amplified by PCR.

(1) Construction of Recombinant Plasmid for Manufacturing Recombinant Foot-and-Mouth Disease Virus Type O.

An amplified O1-Manisa genome (SEQ ID NO: 1) was inserted into a plasmid (pBluescript SK II) to prepare a pO1-Manisa (pO1 M) plasmid. In the prepared pO1 M, the gene encoding the P1 structural protein was replaced with the gene encoding the structural protein of O-serotype FMDV O PA2 (SEQ ID NO: 2) (GenBank Accession No. GU384682.1) to prepare pO1 M-O PA2 P1 (SEQ ID NO: 3) plasmid.

By using the plasmid (pO1 M-O PA2 P1) prepared as above, a B cell epitope sequence (C3d sequence (GGTAAGCAGCTCTACAACGTGGAGGCCACATCC-TATGCC, SEQ ID NO. 4) corresponding to an amino acid residue sequence (GKQLYNVEATSYA, SEQ ID NO: 5) was inserted into a VP1 sequence [PA2-C3d: base pair positions 456 and 457 (amino acid positions 152 and 153, i.e., bases 2025 and 2026 of the pO1 M-O PA2 P1 sequence)]. Afterward, 300 ng/μL of pO1 M-A22 P1 was used as the PCR template addition to the use of 1 μL of 10 pmole/μL primer C3d F (5'-GGAGGCCACATCC-TATGCCCGCGAGAGGCCCTA-GGTCGC-3', SEQ ID NO: 6) and 1 μL of 10 pmole/μL primer C3d R (5'-ACGTTGTAGAGCTGCTTACCGCGAGGGTCGCC-GCTCAGCT-3', SEQ ID NO: 7). The materials were used by the same self-ligating method used in previous studies to prepare a targeting plasmid. The finally prepared recombinant plasmid is the one represented by SEQ ID NO: 8.

(2) Construction of Recombinant Plasmid for Manufacturing Recombinant Foot-and-Mouth Disease Virus Type A An amplified O1-Manisa genome (SEQ ID NO: 1) was inserted into a plasmid (pBluescript SK II) to prepare a pO-Manisa (pO1 M) plasmid. In the prepared pO1 M, the gene encoding the structural protein was replaced with the gene encoding the structural protein of A-serotype FMDV A22/Iraq/24/64 (SEQ ID NO: 9) (GenBank Accession No. AY593764.1) to prepare O1 M-A22 P1 (SEQ ID NO: 10) plasmid.

By using the plasmid (O1 M-A22 P1) prepared as above, a B cell epitope sequence (C3d sequence (GGTAAGCAGCTCTACAACGTGGAGGCCACATCC-TATGCC, SEQ ID NO. 4) corresponding to an amino acid residue sequence (GKQLYNVEATSYA, SEQ ID NO: 5) was inserted into a VP1 sequence [PA2-C3d: base pair positions 453 and 454 (amino acid positions 151 and 152, i.e., bases 2025 and 2026 of the pO1 M-O PA2 P1 sequence)]. Afterward, 300 ng/μL of 01 M-A22 P1 was used as the PCR template in addition to the use of 1 μL of 10 pmole/μL primer C3d F (5'-GGAGGCCACATCC-TATGCCCGCGAGAGGCCCT-AGGTCGC-3', SEQ ID NO: 6), 1 μL of 10 pmole/μL primer C3d R (5'-ACGTTGTAGAGCTGCTTACCGCGAGGGTCGCC-GCTCAGCT-3', SEQ ID NO: 7). The materials were used by the same self-ligating method used in previous studies to prepare a targeting plasmid. The finally prepared recombinant plasmid is the one represented by SEQ ID NO: 11.

Figure 1B:
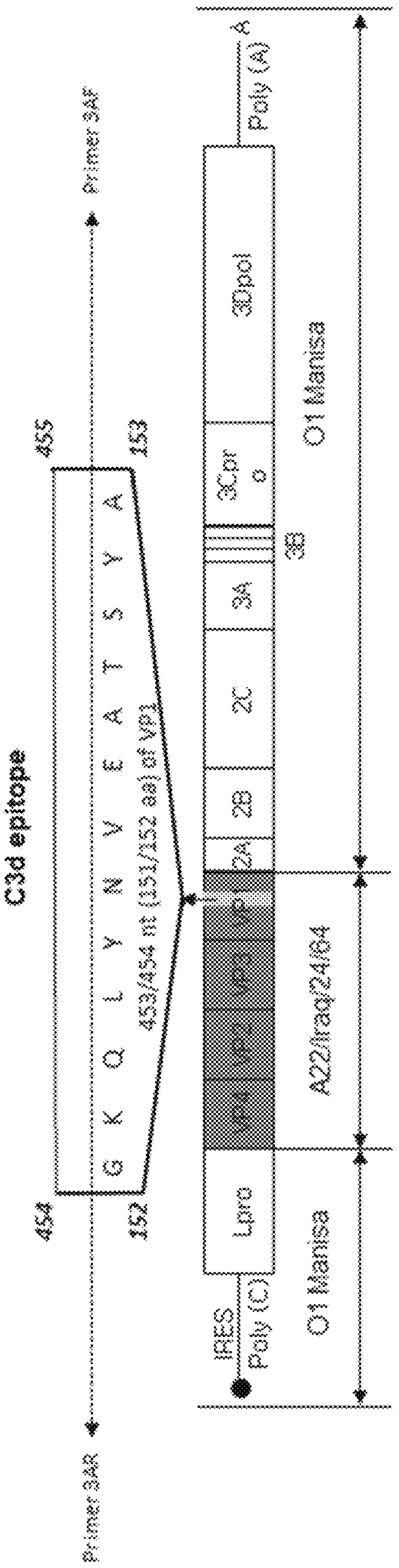
FIG. 1*b* shows a genetic schematic diagram of a recombinant immune-boosting foot-and-mouth disease virus type A according to the present disclosure.

FIGS. 1*a* and 1*b* show schematic diagrams of the final plasmids for O PA2-C3d and A22-C3d, respectively.

PCR conditions were as follows: 10 μL of 5× Phusion HF buffer (Thermo Scientific, Waltham, MA, USA), 1 μL of 10 mM dNTPs (Invitrogen, Carlsbad, CA, USA), 1 μL of 2 U/μL Phusion DNA polymerase (Thermo Scientific), and 35 μL of sterile distilled water were mixed. PCR amplification with the mixture was performed at a temperature of 98 °C for 30 seconds, 98 °C for 10 seconds, 65 °C for 20 seconds, and 72 °C for 2 minutes and 30 seconds, with a final cycle of amplification at 72 °C for 10 minutes. That way, a total of 25 cycles of PCR amplification were performed. Next, 1 μL of DpnI (Enzynomics, Daejeon, Korea) was added to 25 μL of PCR product, and the mixture was reacted in an incubator at a temperature of 37 °C for 1 hour. Then, 35 μL of sterile distilled water, 5 μL of Ligation High (TOYOBO, Osaka, Japan), and 1 μL of 5 U/μL T4 polynucleotide kinase (TOYOBO, Osaka, Japan) were added to 4 μL of DpnI-treated product. The mixture was ligated in a water bath at a temperature of 16 °C for 1 hour.

After ligation, the plasmid was transformed into 100 μL of DH5α cells (Yeast Biotech, Taipei, Taiwan) according to the manufacturer's protocol. The transformed cells were plated on agar plates containing ampicillin and cultured at a temperature of 37 °C overnight.

Colonies were picked from the plate with a pipette tip, and these colonies were mixed with 18 μL of sterile distilled water, 1 μL of 10 μmol forward universal primer VP1 (5'-AGNGCNGGNAARTTTGA-3') (SEQ ID NO: 12), and 1 μL of 10 μmol/μL reverse universal primer. Primer VP1 (5'-CATGTCNTCCATCTGGTT-3') (SEQ ID NO: 13) was added to the colony PCR tube, and PCR amplification was performed at a temperature of 94 °C for 5 minutes, 94 °C for 30 seconds, 55 °C for 30 seconds, 72 °C for 1 minute, with a final cycle of amplification at 72 °C for 5 minutes. That way, a total of 25 cycles of PCR amplification were performed. In the universal primer, N may represent any nucleotide. 5 μL of PCR sample was mixed with 1 μL of 6× loading buffer (DYNE BIO, Gyeonggi-do, Korea) and loaded on an agarose gel. Then, 5 μL of 100 bp marker (DYNE BIO) was also loaded onto the gel. After performing electrophoresis at a voltage of 100 V for 30 minutes, the bands were evaluated using Gel Doc. After the band evaluation, 5 μL of PCR product was mixed with 2 μL of ExoSAP (Thermo Scientific), and the mixture was amplified by PCR at a temperature of 37 °C for 15 minutes and at a temperature of 85 °C for 15 minutes. The insertion of the epitope into VP1 was confirmed by whole DNA sequencing. After confirming the base sequence, the colonies were placed in 200 mL of LB medium containing ampicillin and cultured with shaking at a temperature of 37 °C overnight. A plasmid was prepared using Midi prep (MACHEREYNAGEL, Duren, Germany).

2. Preparation of Immune-Boosting Recombinant Foot-and-Mouth Disease Viruses

The recombinant plasmids prepared above containing the recombinant foot-and-mouth disease viruses were transfected into BHKT7-9 (a cell line expressing T7 RNA polymerase) using Lipofectamine 3000 Reagent (Invitrogen, Carlsbad, CA, USA), and then the viruses were cultured for 2 to 3 days and recovered. The prepared viruses were then delivered to fetal goat tongue (ZZ-R) cells or baby hamster kidney-21 (BHK-21) cells for virus propagation.

3. Purification of Antigens from Recombinant Foot-and-Mouth Disease Viruses Type O and A (Inactivated Virus) Presenting C3d-Epitope on Surface Purified antigens were prepared in BHK-21 cells infected with recombinant immunostimulatory FMDV O PA2-C3d and A22-C3d, the FMDVs being made through recombination with a gene corresponding to the rapidly emerging P1 phenotype (referenced sequence) by reverse genetics according to the modified method described by Lee et al. (Non-patent Document 2).

For virus infection, the culture medium was replaced with Dulbecco's Modified Eagle's medium (DMEM; HyClone, Logan, UT, USA) which was serum-free, and the cells were cultured at a temperature of 37 °C for 1 hour under a 5% $CO_2$ atmosphere and inoculated with the viruses. Extracellular viruses were then removed. 24 hours after infection, the viruses were inactivated by treatment with 0.003 N binary ethyleneimine twice for 24 hours in a shaking incubator and then concentrated with polyethylene glycol (PEG) 6000 (Sigma-Aldrich, St. Louis, MO, USA). The virus concentrates were layered on sucrose with a 15% to 45% density gradient and centrifuged. After the ultracentrifugation, a hole was made in the bottom of the centrifuge tube, and 1 mL of fractions were collected. The presence of FMDV particles in samples of each fraction was confirmed by optical density using a lateral flow device (BioSign FMDV Ag; Princeton BioMeditech, Princeton, NJ, USA). Before the use of the cells in field experiments, the ZZ-R and BHK-21 cells were treated with the pre-PEG treated supernatant more than twice to confirm that cytopathic effect (CPE) did not occur, so it was confirmed that there was no live virus in the supernatant.

Figure 11:
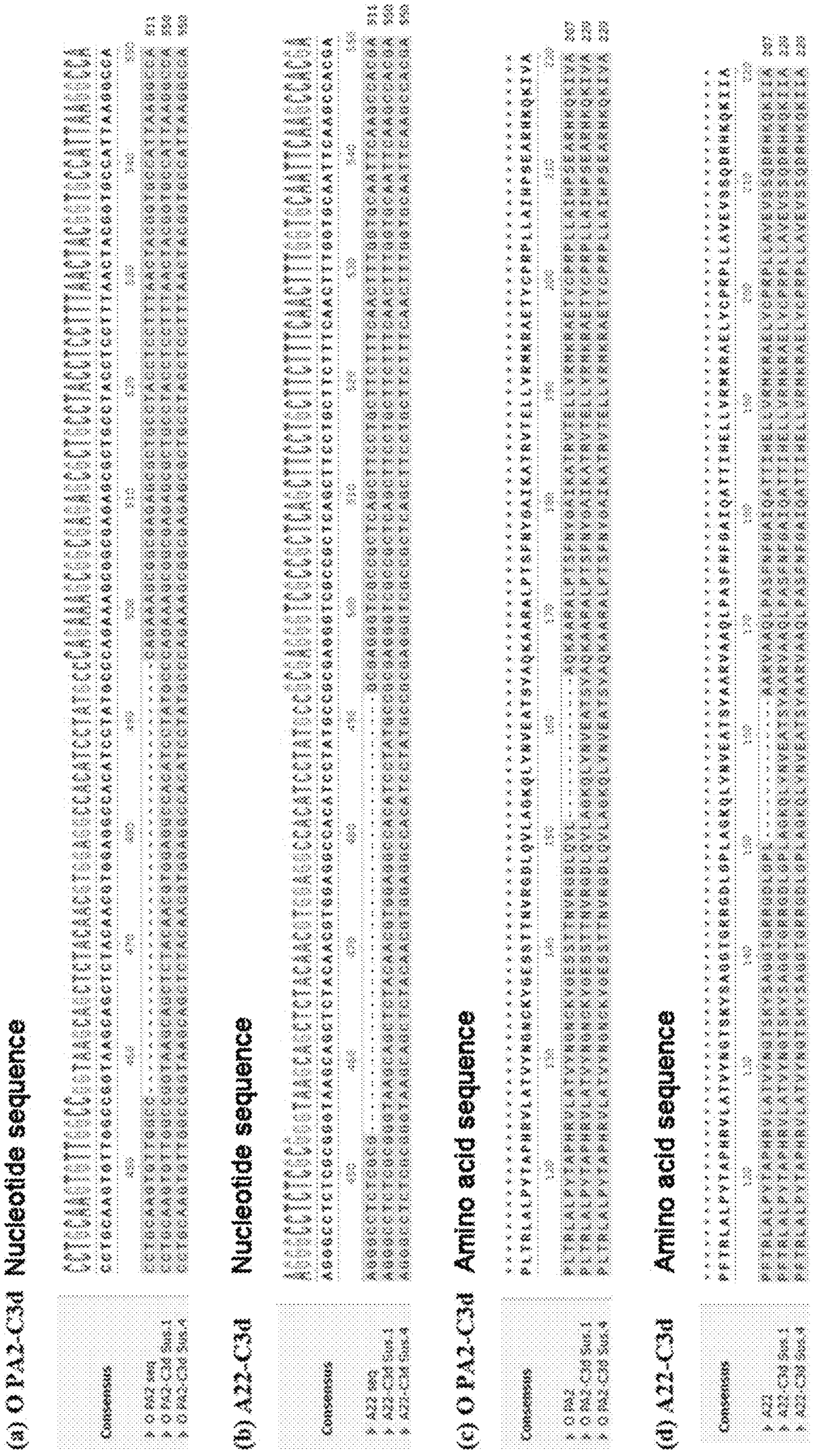
FIG. 11 shows the VP1 sequences of O PA2-C3d and A22-C3d of the present disclosure, during the first (Sus. 1) and fourth (Sus. 4) suspension cell (BHK) passages, in which the VP1 sequences of O PA2-C3d and A22-C3d were aligned using SnapGene; (a) O PA-C3d nucleotide sequence; (b) A22-C3d nucleotide sequence; (c) O PA2-C3d amino acid sequence; and (d) A22-C3d amino acid sequence.

4. Identification of Structural and Non-Structural Proteins Using Purified Antigens and Inspection of 146S Particles Using TEM Structural proteins (SPs) expressed using purified antigens from cells infected with immune-boosting recombinant FMDV O PA2-C3d and A22-C3d could be recognized by the formation of bands representing the SPs, and the bands were identified with a Rapid antigen kit (PBM kit, PBM Co Ltd., Princeton, NJ, USA). There was no band formation corresponding to the non-structural proteins (NSPs) of the FMDVs. The characteristics of the virus particles (146S) were confirmed by transmission electron microscopy (TEM) imaging. Additionally, when delivering the recombinant viruses, the sequence often changed. To prove that the sequence did not change during the first and fourth delivery, the FMDVs with the specific epitope of 'C3d' inserted were examined to see if the FMDVs maintained the genetic stability of the viruses even after the delivery thereof into cells, and it was confirmed that there was no change in sequence until the fourth passage (FIG. 11).

5. Immunogenicity Evaluation of O PA2-C3d and A22-C3d, Immune-Boosting Foot-and-Mouth Disease Vaccine Strains for Overcoming Interference of Maternally-Derived Antibodies in Test Animal (Mice)

(1) Mice

Mouse experiments were performed according to the method described by Lee et al. (Non-patent Document 2). Age-matched and gender-matched wild-type C57BL/6 mice (6-week-old to 7-week-old female) were purchased from KOSA BIO Inc. (Gyeonggi, Korea). All mice were housed in micro isolator cages with ad libitum access to food and water in an animal facility compliant with the Specific Pathogen-Free (SPF) Animal Biosafety Level 3 (ABSL3) of the Animal and Plant Quarantine Agency. All animals were allowed to acclimate for at least 1 week before being used in experiments. A breeding room was set up with a 12-hour light/dark cycle, a temperature of approximately 22 °C, and a relative humidity of approximately 50%. The test was conducted in accordance with institutional guidelines and approval from the Institutional Animal Care and Use Committee under the Animal and Plant Quarantine Agency (certification number IACUC-2021-584).

(2) Vaccination and FMDV Administration to Mice

To verify the immunogenicity and short-term immunity-inducing effect of antigens isolated and purified from highly immunogenic FMDV O PA2-C3d and A22-C3d and confirm potentials thereof as master seed viruses (MSVs) for developing a foot-and-mouth disease vaccine, animal experiments were conducted as follows.

The vaccine compositions used in the experiments were as follows: O PA2-C3d and A22-C3d (15 μg/dose/mL, 1/10 to 1/640 dose for pigs), ISA 206 (Seppic, Paris, France, 50%, w/w), 10% $Al(OH)_3$ and 15 μg/mouse Quil-A (InvivoGen, San Diego, CA, USA). FMDV (100 LD 50 ME-SA topotype from O/VET/2013 or 100 $LD_{50}$ A/Malay/97, SEA topotype) was injected intramuscularly (IM) into the thigh muscles of mice at 0 days post vaccination (0 dpv) and injected intraperitoneally (IP) to the same mice at 7 dpv. Mice in the negative control group were administered with the same volume of phosphate-buffered saline (PBS, pH 7.0) through the same routes. Survival rates and body weight changes were monitored for up to 7 days post-challenge (dpc) after the administration to assess short-term immunogenicity.

As a preliminary experiment for the experiments in the target animal (pigs), a PD 50 test was conducted to confirm the immunogenicity of the bivalent test vaccine including antigens of O PA2-C3d antigen+A22-C3d. The target animal group was compared with a group administered with a test vaccine including antigens of O PA2 antigen+A22, which was used as the backbone of the immune-boosting vaccine strains. The vaccine compositions used in the experiments were as follows; O PA2-C3d antigen+A22-C3d antigens (15 μg+15 μg/dose/ml, 1/10 to 1/640 dose) or O PA2 antigen+A22 antigens (15 μg+15 μg/dose/ml, 1/10 to 1/640 dose), ISA 206 (50%, w/w), 10% $Al(OH)_3$, 15 μg Quil-A/mouse. The negative control group was administered with the same volume of PBS through the same routes.

After the mice were vaccinated at 0 dpv via an I.M. injection, the mice were intraperitoneally administered with FMDVs (100 $LD_{50}$, O/VET/2013, ME-SA topotype or 100 $LD_{50}$ A/Malay/97, SEA topotype) at 7 days post vaccination (7 dpv), and then survival rates and body weight changes were monitored until 7 days post challenge (dpc).

6. Immunogenicity Evaluation of O PA2-C3d and A22-C3d, Immune-Boosting Foot-and-Mouth Disease Vaccine Strains for Overcoming Interference of Maternally-Derived Antibodies in Target Animal (Pigs)

(1) Pigs

Pigs (8 to 9 weeks old, total n=32) were screened using SP O ELISA and SP A ELISA for antibody titers (PI value: 50%) and VN titers (based on 1.6 Log 10), and then divided into MDA(+) and MDA(−) groups (n=16 for each group).

The pigs in each group of the MDA(+) and MDA(−) groups were randomly divided into three groups (n=4 or 6/group): a negative control (NC) group, a O PA2+A22 (positive control, PC)-treated group, and a O PA2-C3d+A22-C3d-treated group.

The animals were isolated in a closed isolation room (ABSL3) during the experiments. After arrival at ABSL, all animals were housed in cages with ad libitum access to food and water and used in experiments after at least 1 week of acclimatization. A breeding room was set up with a 12-hour light/dark cycle, a temperature of approximately 22 °C, and a relative humidity of approximately 50%. This disclosure was conducted in accordance with institutional guidelines and approval from the Institutional Animal Care and Use Committee under the Animal and Plant Quarantine Agency (certification number IACUC-2021-584).

(2) Induction of Immune Response and Sampling Through Vaccination

To evaluate the immunogenicity of antigens isolated and purified from O PA2-C3d and A22-C3d, the immune-boosting foot-and-mouth disease vaccine strains manufactured to overcome interference of maternally-derived antibodies in the target animal, which were pigs, and to observe the avoidance effect of overcoming the interference of the maternally-derived antibodies, the experiments were performed using MDA(+) (FMD-seropositive)-wild pigs and MDA(−) (FMD-seronegative)-wild pigs, which were positive and negative for maternally-derived antibodies, respectively, and the vaccine compositions were as follows; A total of 1 ml of vaccine was taken as 1 dose, and the vaccine was prepared by including 15 μg O PA2 antigen+15 μg A22 antigen (positive control group, PC group) or 15 μg O PA2-C3d antigen+15 μg A22-C3d antigen (experimental group), ISA 206 (50%, w/w), 10% $Al(OH)_3$, and 150 μg Quil-A. The negative control group (NC group) was administered with the same volume of PBS through the same routes.

The pigs at the ages of 8 to 9 weeks, which were positive or negative for maternally-derived antibodies, were screened and divided into two groups: MDA(+) group (n=16) and MDA(−) group (n=16). The individuals in the MDA(+) group and MDA(−) group were divided into three groups: an NC group (PBS-administered group, n=4/group), a PC group (O PA2+A22-administered group, n=6/group), and an experimental group (O PA2-C3d+A22-C3d administration group, n=6/group). Each group was administered with 1 mL vaccine through an I.M. route twice at 28-day intervals (0 dpv and 28 dpv). Blood samples from vaccinated pigs were collected at 0, 7, 14, 28, 42, 56, 70, and 84 dpv and subjected to serological analysis for such as SP O ELISA and SP A ELISA, and VN titer confirmation. In the case of SP O ELISA and SP A ELISA, considering the antibody positivity rate depending on the characteristics of the antigens, FMDV types O and A were compared using the PrioCHECK™ kit and VDPro® kit, respectively. In addition, peripheral blood mononuclear cells (PBMCs) were isolated from the blood samples collected at all sampling schedules, and changes in gene expression related to test vaccine-mediated cellular and humoral immune responses were analyzed.

(3) Serological Analysis

To detect SP antibodies in serum, PrioCHECK™ FMDV type O or FMDV type A (Prionics AG, Switzerland) and VDPro® FMDV type O or FMDV type A (Median Diagnostics, Gangwon-do, Korea) were used. The absorbance of the ELISA plates was converted to percent inhibition (PI) values. Animals were considered positive for antibodies when the PI value was greater than or equal to 50% for the PrioCHECK™ FMDV kit or greater than or equal to 40% for the VDPro® FMDV kit.

A virus neutralization test (VNT) was performed in accordance with the manual of the World Organization for Animal Health (OIE). The serum was heat-inactivated at a temperature of 56 °C for 30 minutes in a water bath. Cell density was adjusted to form a 70% monolayer, and two-fold serial dilutions (1:8-1:1024) of serum samples were prepared. The diluted serum samples were then incubated with homologous viruses of 100-tissue culture infectious dose $(TCID)_{50}$/0.5 mL at a temperature of 37 °C for 1 hour. After 1 hour, LF-BK (bovine kidney) cell suspension was added to all wells. After 2 to 3 days, CPE was assessed to determine a titer, which was calculated as the inverse of antibody dilution in the form of a Log 10 value required to neutralize the 100 $TCID_{50}$ viruses. FMDV O/PA2 and FMDV A22/IRAQ were used for the VNT.

(4) PECs Isolation and Cell Culture

Naïve mice were anesthetized using $CO_2$ and sacrificed. The abdominal cavity was washed with 5 mL of balanced salt solution (HBSS, Gibco, Waltham, MA, USA) buffer of Hank, which was cooled without $Ca^{2+}$, $Mg^{2+}$, and phenol-red. A peritoneal lavage fluid was centrifuged at 300×g at a temperature of 4 °C for 10 minutes. The pelletized PECs were resuspended and counted using a Bio-Rad TC20 automated cell counter (Bio-Rad). All cells were freshly isolated before use. Cryopreserved cells were not used in any of the experiments. Then, the purified PECs were incubated in a complete medium. The medium was made from 10% fetal calf serum (HyClone), 3 mM L-glutamine (Sigma-Aldrich), 10 mM HEPES (Sigma-Aldrich), 100 U/mL of penicillin/streptomycin (Sigma-Aldrich), and Roswell Park Memorial Institute (RPMI) 1640 (Gibco, Carlsbad, CA, USA) supplemented with 0.05 mM 2-beta-mercaptoethanol (Sigma-Aldrich). The incubation was performed at a temperature of 37 °C and under a 5% $CO_2$ atmosphere.

(5) PBMCs Isolation and Cell Culture

Porcine PBMCs were isolated from the whole blood of pigs vaccinated at the previously mentioned specific time points (n=4 or 6/group) in accordance with the method described by Lee et al. (Non-patent Document 2). The whole blood (20 mL/individual) was collected independently in BD Vacutainer heparin tubes (BD, Becton, Dickinson and Company, Franklin Lakes, NJ, USA). The PBMCs were isolated using Ficoll-Paque™ PLUS (GE Healthcare Bio-Sciences Corp., Piscataway, NJ, USA) gradient centrifugation. Residual red blood cells were lysed by treatment with ammonium-potassium chloride (ACK) lysis buffer (Gibco, Carlsbad, CA, USA).

The PBMCs were suspended in Dulbecco's PBS (Gibco) without $Ca^{2+}$ and $Mg^{2+}$. The PBMCs were then supplemented with 2% fetal bovine serum (FBS) (Gibco) and counted using a volumetric flow cytometer (Miltenyi Biotec, Bergisch Gladbach, Germany). All cells were freshly isolated before use. Cryopreserved cells were not used in any of the experiments. Afterward, the purified PBMCs were resuspended in RPMI1640 (Gibco) medium supplemented with 10% FBS (HyClone, Logan, UT, USA), 3 mM L-glutamine (Sigma-Aldrich, St. Louis, MO, USA), and 100 U/mL of penicillin-streptomycin (Sigma-Aldrich).

(6) Antigen-Induced IFNγ ELISpot Assay for PECs and PBMCs In Vitro

PA2-C3d antigen-mediated and A22-C3d antigen-mediated IFNγ secretions were analyzed using a commercial ELISpot assay kit (Catalog numbers EL485 and EL985 for mice and pigs, R&D Systems, Minneapolis, MN, USA) in accordance with the manufacturer's instructions. Isolated murine PEC or porcine PBMC ($5\times10^5$ cells/well) were cultured in 96-well PVDF-supported microplates containing monoclonal capture antibodies specific for mouse or porcine IFNγ. Inactivated FMDV (O PA2, O PA2-C3d, A22, and A22-C3d) antigens were stimulated at each concentration of 4 μg/mL (final concentration) for 18 hours in a humidified incubator at a temperature of 37 °C and under a 5% $CO_2$ atmosphere. PBS and 5 μg/mL of phorbol myristate acetate (PMA, Sigma-Aldrich) were used as negative and positive controls, respectively. The plates were washed with wash buffer and incubated with biotinylated anti-mouse IFNγ antibodies (1:119) or anti-porcine antibodies (1:119) at a temperature of 4 °C overnight. Afterward, the plates were incubated with streptavidin (1:119) AP-conjugated at RT for 2 hours. The plates were washed and developed with 5-bromo-4-chloro-3'indoliphosphate p-toluidine salt (BCIP)/nitro blue tetrazolium chloride (NBT). The cells were counted using an ImmunoSpot ELISpot reader (AID iSpot reader system; Autoimmune Diagnostika GmbH, Strassberg, Germany). Results were expressed as spot forming units (SFU).

(7) RNA Isolation, cDNA Synthesis, and Quantitative Real-Time PCR

Total RNAs were extracted from purified porcine PBMCs using a TRIzol reagent (Invitrogen) and RNeasy Mini Kits (QIAGEN, Valencia, CA, USA). cDNAs were prepared by reverse transcription using a GoScript reverse transcription system (Promega, Madison, WI, USA) in accordance with the manufacturer's instructions. The synthesized cDNAs were amplified by quantitative real-time PCR (qRT-PCR) on a Bio-Rad iCycler using iQ SYBR Green Supermix (Bio-Rad, Hercules, CA, USA).

Gene expression levels were normalized to hprt levels and presented as relative ratios compared to controls. The list of primers used in this disclosure is listed in Table 1.

TABLE 1

List of primer sequences for qRT-PCR

| Target | Forward/ Reverse | Sequence (5'-3') | Length (mer) | Sequence number |
|---|---|---|---|---|
| IFNα | IFNα F | CATCTGCTCTCTGGGCTGTG | 20 | 14 |
| | IFNα R | TGAGGGGATCCAAAGTCCCT | 20 | 15 |
| IFNβ | IFNβ F | TGCAACCACCACAATTCCAGA | 21 | 16 |
| | IFNβ R | GGTTTCATTCCAGCCAGTGC | 20 | 17 |
| IFNγ | IFNγ F | GCCATTCAAAGGAGCATGGAT | 21 | 18 |
| | IFNγ R | CTGATGGCTTTGCGCTGGAT | 20 | 19 |
| IL-1β | IL-1β F | AGCCAGTCTTCATTGTTCAGGT | 22 | 20 |
| | IL-1β R | TCATCTCTTTGGGGCCATCAG | 21 | 21 |
| IL-17A | IL-17AF | CTCGTGAAGGCGGGAATCAT | 20 | 22 |
| | IL-17A R | GGTGTGCTCCGGTTCAAGAT | 20 | 23 |
| IL-23p19 | IL-23p19 F | CCATATCCAGTGCGGGGATG | 20 | 24 |
| | IL-23p19 R | AGGCCTTGGTGGATCCTTTG | 20 | 25 |
| IL-23R | IL-23R F | TCCCTCATTGCAAAGCACAA | 20 | 26 |
| | IL-23R R | GCATCTCCTCTTGCAAGCAAAT | 22 | 27 |
| IL-2 | IL-2 F | AAGCTCTGGAGGGAGTGCTA | 20 | 28 |
| | IL-2 R | CAACAGCAGTTACTGTCTCATCA | 23 | 29 |
| IL-10 | IL-10 F | CGGCCCAGTGAAGAGTTTCT | 20 | 30 |
| | IL-10 R | TGCCTTCGGCATTACGTCTT | 20 | 31 |
| TGFβ | TGFβ F | GGCTGTCCTTTGATGTCACC | 20 | 32 |
| | TGFβ R | GGCCAGAATTGAACCCGT | 18 | 33 |
| IL-4 | IL-4 F | CTCACCTCCCAACTGATCCC | 20 | 34 |
| | IL-4 R | TGTGTCCGTGGACGAAGTTG | 20 | 35 |
| IL-6 | IL-6 F | CTGCAGTCACAGAACGAGTG | 20 | 36 |
| | IL-6 R | CGGCATCAATCTCAGGTGCC | 20 | 37 |
| CD40 | CD40 F | GTCATCAGCACAAATACTGC | 20 | 38 |
| | CD40 R | CACAAGTGGTGTCTGTTTTC | 20 | 39 |
| CD80 | CD80 F | TCAGGCATCGTTCAGGTGAC | 20 | 40 |
| | CD80 R | TGACAGCCAGCACCATTTCA | 20 | 41 |
| CD86 | CD86 F | TGGGACTGAGTAACATTCTCTTTGT | 25 | 42 |
| | CD86 R | CCAGCTCATCCAGGCTTAGG | 20 | 43 |

TABLE 1-continued

List of primer sequences for qRT-PCR

| Target | Forward/ Reverse | Sequence (5'-3') | Length (mer) | Sequence number |
|---|---|---|---|---|
| MHC Class I | MHC Class I F | TGAGCTATTTCTACACCGCCG | 21 | 44 |
| | MHC Class I R | TCGTCCACGTAGCCGACTT | 19 | 45 |
| MHC Class II | MHC Class II F | CTCCAGTGATGCTGGGTCAG | 20 | 46 |
| | MHC Class II R | TGACAGAGTGCCCGTTCTTC | 20 | 47 |
| CD21 | CD21 F | TGCCATGCCTACAAAGCTGA | 20 | 48 |
| | CD21 R | GTAGTAACCAGGGCGGCATT | 20 | 49 |
| CD28 | CD28 F | TCAAAGGAGTTCCGGGCATC | 20 | 50 |
| | CD28 R | CTGAAGCAGGCGGGAGTAAT | 20 | 51 |
| ICOS | ICOS F | GGATGTGCAGCCTTTGTTGT | 20 | 52 |
| | ICOS R | CAGAGCGTACCAAATTGCGG | 20 | 53 |
| CTLA4 | CTLA4 F | GAGTATGGGTCTGCAGGCAA | 20 | 54 |
| | CTLA4 R | ATATGTCGCGGCACAGACTT | 20 | 55 |
| AHNAK | AHNAK F | CACCATCACCGTGACTCGAA | 20 | 56 |
| | AHNAK R | AGTTCGTGCCGTGGAATCTT | 20 | 57 |
| HPRT | HPRT F | CCCAGCGTCGTGATTAGTGA | 20 | 58 |
| | HPRT R | GCCGTTCAGTCCTGTCCATA | 20 | 59 |

7. Statistics

All quantitative data were expressed as mean±standard error of the mean (SEM) unless otherwise specified. Statistical significance between groups was assessed using two-way ANOVA followed by Tukey's post hoc test or one-way ANOVA followed by Tukey's post hoc test. $^*p<0.05$; $^{}p<0.01$; $^{*}p<0.001$; and $^{****}p<0.0001$. Parametric tests were used to compare different groups. Survival curves were created using the Kaplan-Meier method, and differences were analyzed using the log-rank sum test. GraphPad Prism 9.1.2 (GraphPad, San Diego, CA, USA) software and IBM SPSS software (IBM Corp., Armonk, NY, USA) were used for all statistical analyses.

<Example> Manufacturing of Immune-Boosting Foot-and-Mouth Disease Vaccine Strains for Overcoming Interference of Maternally-Derived Antibody and Preparation and Purification of Inactivated Antigens Using O PA2-C3d and A22-C3d To develop a foot-and-mouth disease vaccine for overcoming the interference of maternally-derived antibodies, the PI backbones of the O1 Manisa-O PA2 (O1 M-O PA2) and O1 Manisa-A22/Iraq/24/64 (O1 M-A22) strains, which were previously developed using reverse genetics, were used. In the case of type O, based on the results of previous studies that confirmed the vaccine matching rate for surrounding outbreak situations and the proliferation of the viruses in floating cells, especially based on the results of previous studies that confirmed antigen-mediated immunogenicity in the test animal (mice) and target animal (pigs), O PA2 was determined to be the strongest candidate vaccine strain. In the case of type A, when looking at the global outbreak situation, the matching rate generally tends to be low, but A22 was also classified as a suitable vaccine strain.

In the present disclosure, a strategy to prepare foot-and-mouth disease vaccine strains for overcoming the interference of maternally-derived antibodies against FMDV type O and FMDV type A by inserting the active site of C3d, which was a B cell epitope into the O PA2 and A22 P1 backbone was the same as shown in FIGS. 1*a* and 1*b*, and detailed methods are described in the Materials and methods part.

Figure 2A:
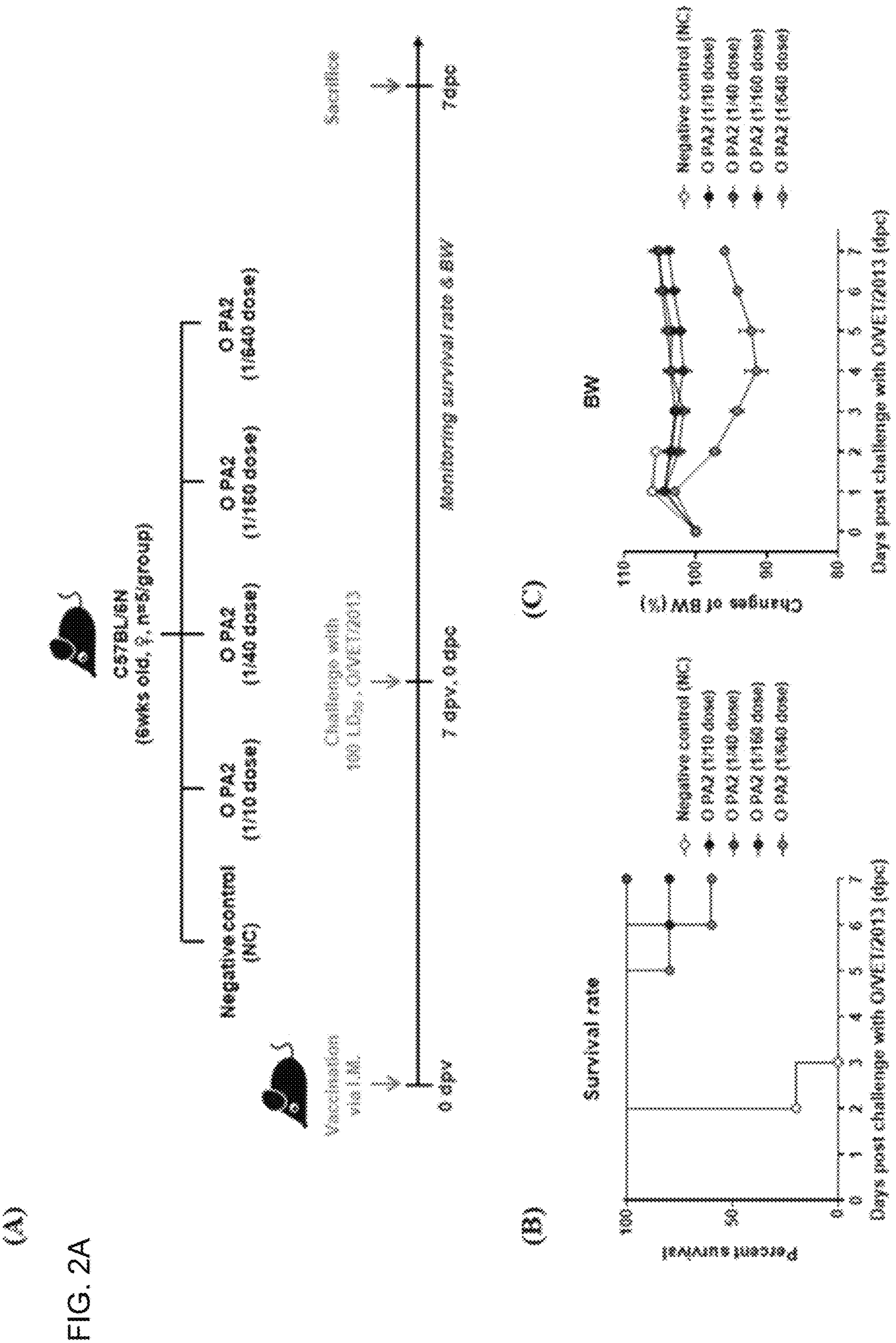
FIGS. 2*a* and 2*b* show an immunogenicity evaluation strategy and results of antigens isolated and purified from O PA2 and A22, respectively.
Figure 2B:
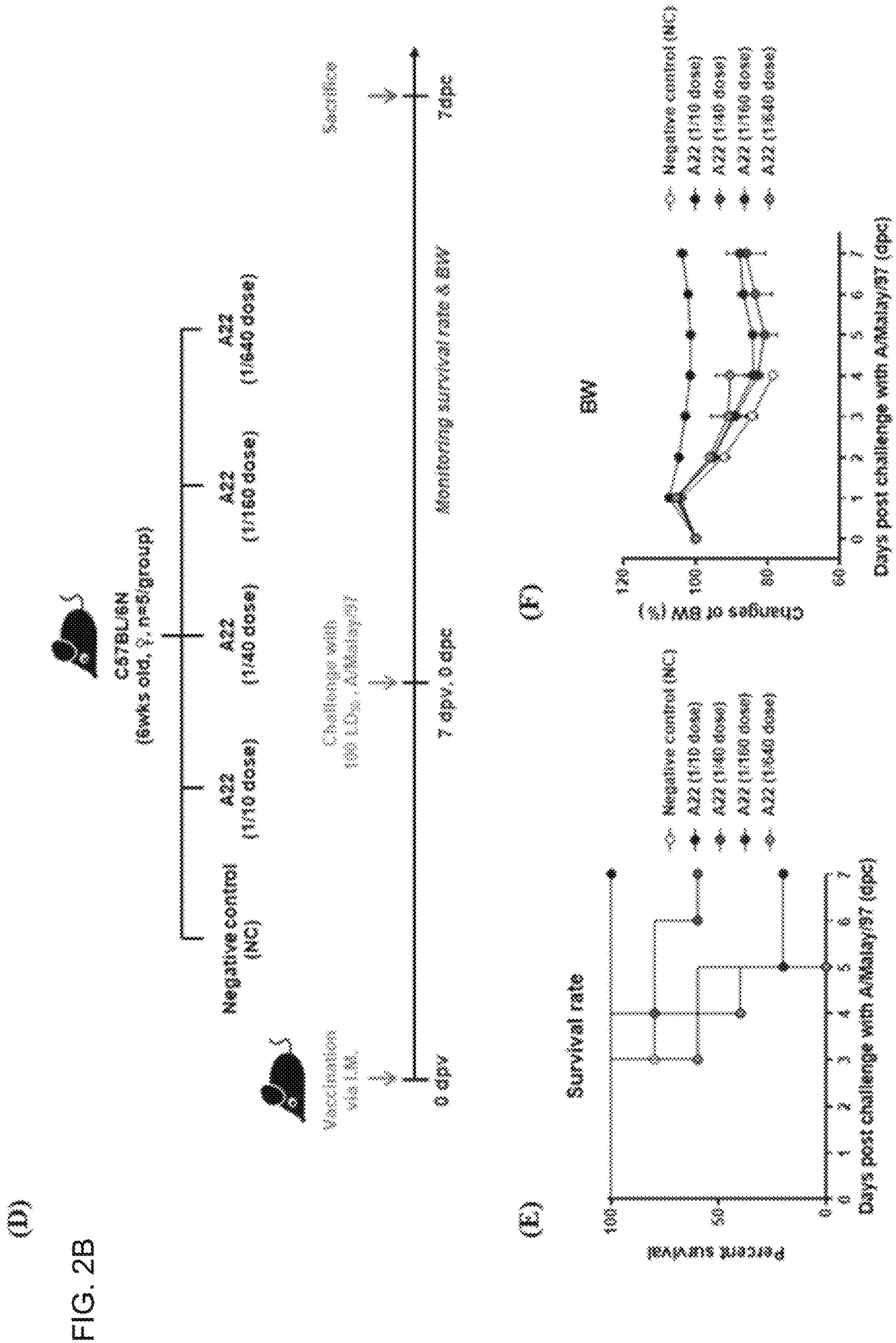
Figure 4A:
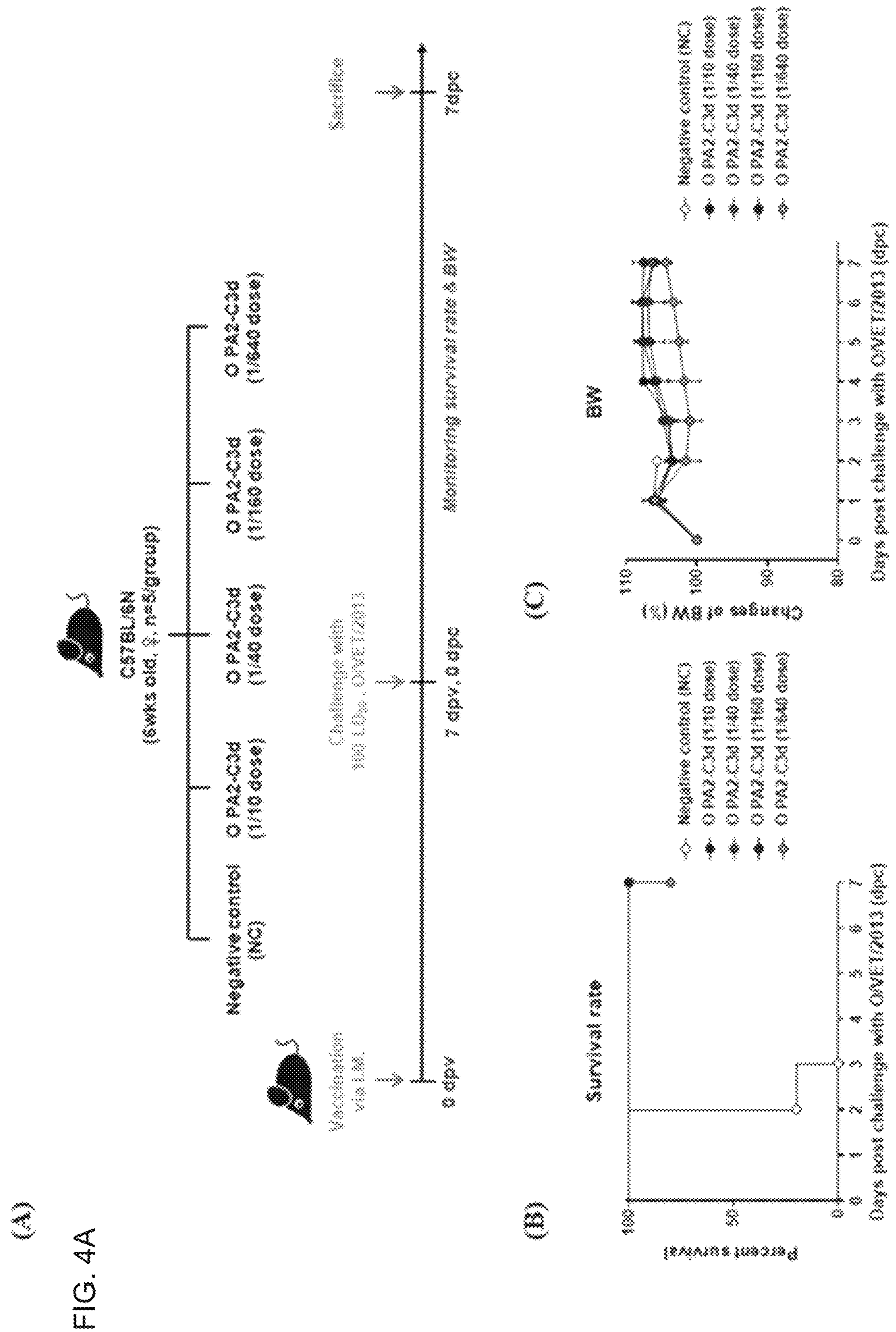
FIG. 4*a* shows an experimental strategy (A), survival rate (B), and body weight change (C) for the recombinant foot-and-mouth disease virus type O according to the present disclosure.
Figure 4B:
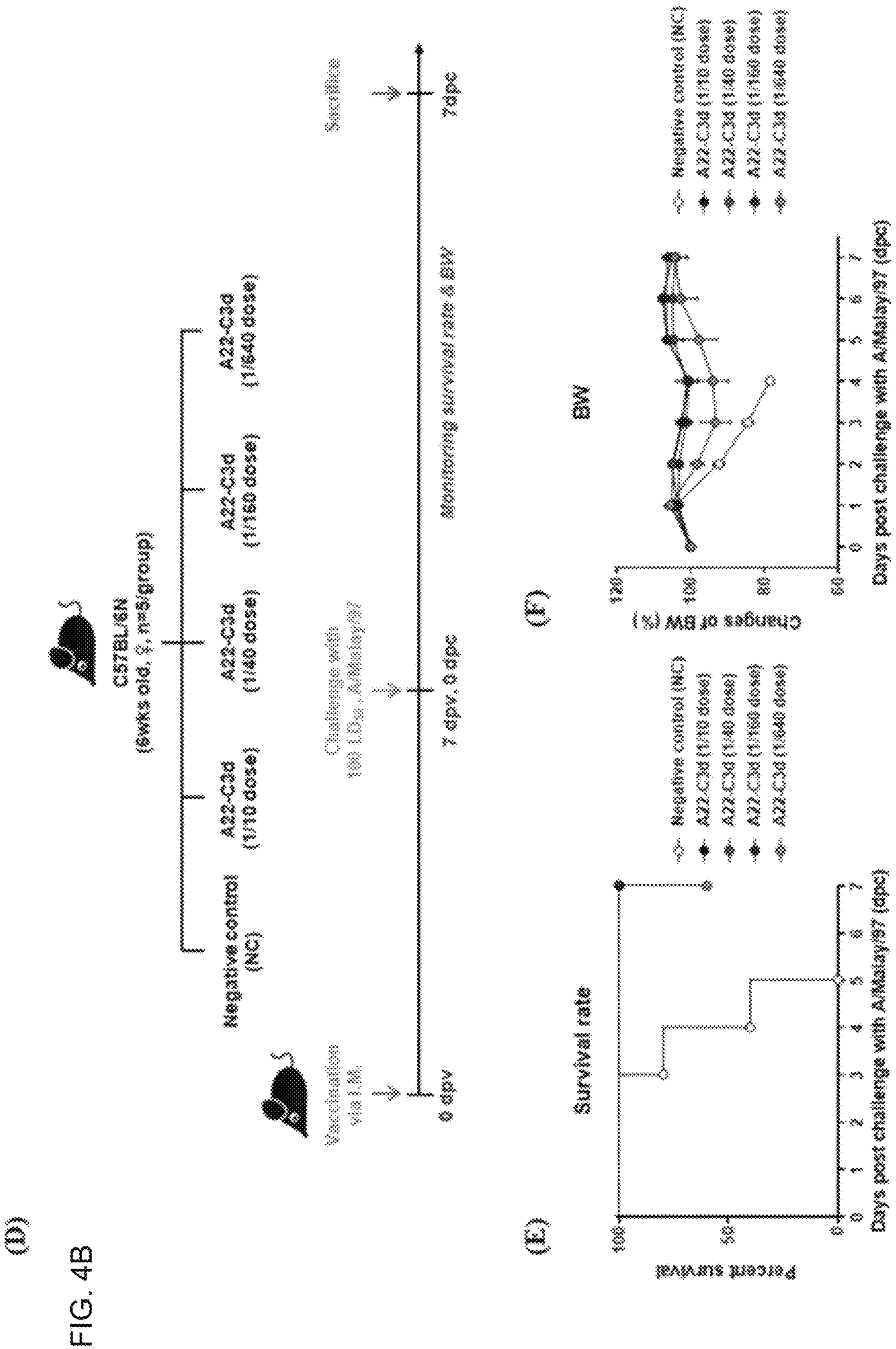
FIG. 4*b* shows an experimental strategy (D), survival rate (E), and body weight change (F) for the recombinant foot-and-mouth disease virus type A according to the present disclosure.

<Experiment Example 1> Evaluation of Immunogenicity in Mice of FMD Vaccine Including Antigens of O PA2-C3d and A22-C3d, Immune-Boosting Foot-and-Mouth Disease Vaccine Strains for Overcoming Interference of Maternally-Derived Antibodies To confirm the immunogenicity of antigens isolated and purified from O PA2-C3d and A22-C3d, which had B cell epitope C3d inserted for activation of B cells, to confirm the immunogenicity of antigens isolated and purified from O PA2 and A22 in mice, to evaluate the potential as a master seed virus (MSV) of vaccines for foot-and-mouth disease, and to evaluate the protective effect against FMDV infection, experiments involving O PA2-C3d and A22-C3d were performed with the same strategy as shown in (A) in FIG. 4*a* and (D) in FIG. 4*b*, respectively, and experiments involving O PA2 and A22 were performed with the same strategy as shown in (A) in FIG. 2*a* and (D) in FIG. 2*b*. The vaccine compositions used in the experiments were as follows; O PA2-C3d or A22-C3d antigens, O PA2 or A22 antigens (15 μg/dose/mL, 1/10 to 1/640 dose), ISA 206 (50%, w/w), 10% $Al(OH)_3$, 15 μg Quil-A/mouse.

After the mice were vaccinated at 0 days post vaccination (0 dpv) via an intramuscular (I.M.) injection, the mice were intraperitoneally injected with FMDVs (100 $LD_{50}$, O/VET/2013, ME-SA topotype or 100 $LD_{50}$ A/Malay/97, SEA topotype) at 7 dpv, and then survival rates ((B) and (C) in FIG. 4*a*) and body weight changes ((E) and (F) in FIG. 4*b*) were monitored until 7 days post challenge (dpc).

As a result of the experiments, the test vaccine containing the antigens of O PA2-C3d showed 97.01 $PD_{50}$ (Log 4) with survival rates of 100% at 1/10, 1/40, and 1/160 doses and 80% at 1/640 dose in mice, and little weight loss was observed at the 1/10, 1/40, and 1/160 doses ((B) and (C) in FIG. 4*a*). In addition, when the test vaccine using the antigens isolated and purified from A22-C3d was inoculated into mice, the test vaccine showed 73.52 $PD_{50}$ ($Log_4$) with survival rates of 100% at 1/10, 1/40, and 1/160 doses and 60% at 1/640 dose. In terms of weight loss, almost no change in body weight was observed at 1/10, 1/40, and 1/160 doses ((E) and (F) in FIG. 4*b*).

However, the vaccine including the antigens of O PA2 showed 55.72 $PD_{50}$ ($Log_4$) ((B) of FIG. 2*a*). The body weight change of O PA2 was reduced to a lower level compared to O PA2-C3d ((C) in FIG. 2*a*).

The vaccine including the antigens of A22-C3d showed 73.52 $PD_{50}$ ($Log_4$) with survival rates of 100% at 1/10, 1/40, and 1/160 doses and 60% at 1/640 doses. No change in body weight was observed at 1/10, 1/40, and 1/160 doses.

However, the vaccine including the antigens of A22 showed 6.06 $PD_{50}$ ($Log_4$) ((E) of FIG. 2B). The body weight change of A22 was reduced to a lower level compared to A22-C3d ((F) in FIG. 2*b*).

A $PD_{50}$ test was performed to determine the immunogenicity of the investigational bivalent vaccine (including O PA2-C3d+A22-C3d antigens and via a combined administration of O PA2-C3d and A22-C3d) in pigs. Results were compared with those of the group that received the test vaccine (including the antigens of PA2+A22 and via a combined administration of O PA2 and A22) used as the backbone of the immune-boosting vaccine strain (FIGS. 5 and 3).

Figure 3:
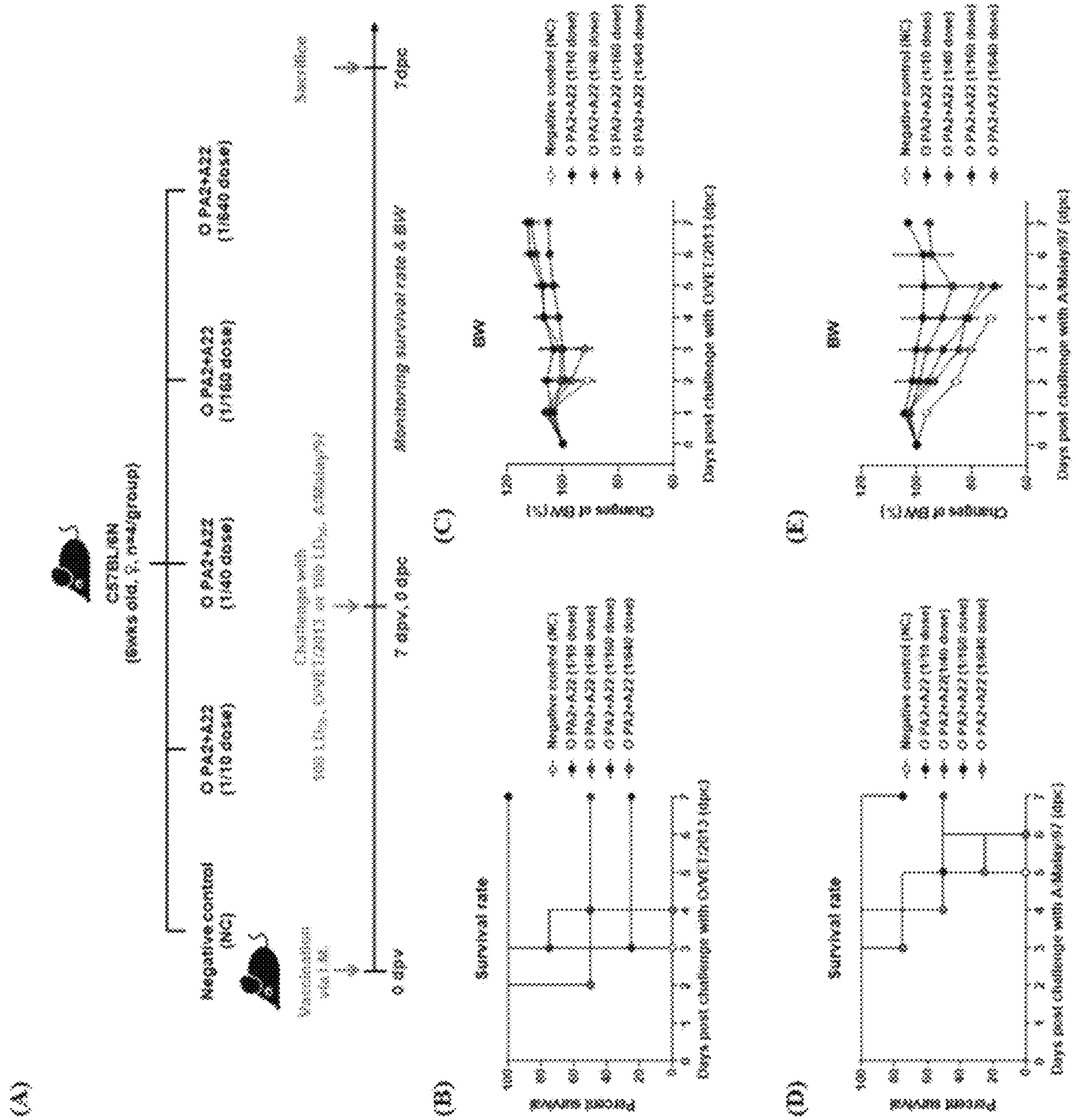
FIG. 3 shows an immunogenicity evaluation strategy and results when the antigens isolated and purified from O PA2 and A22 are administered in combination.
Figure 5:
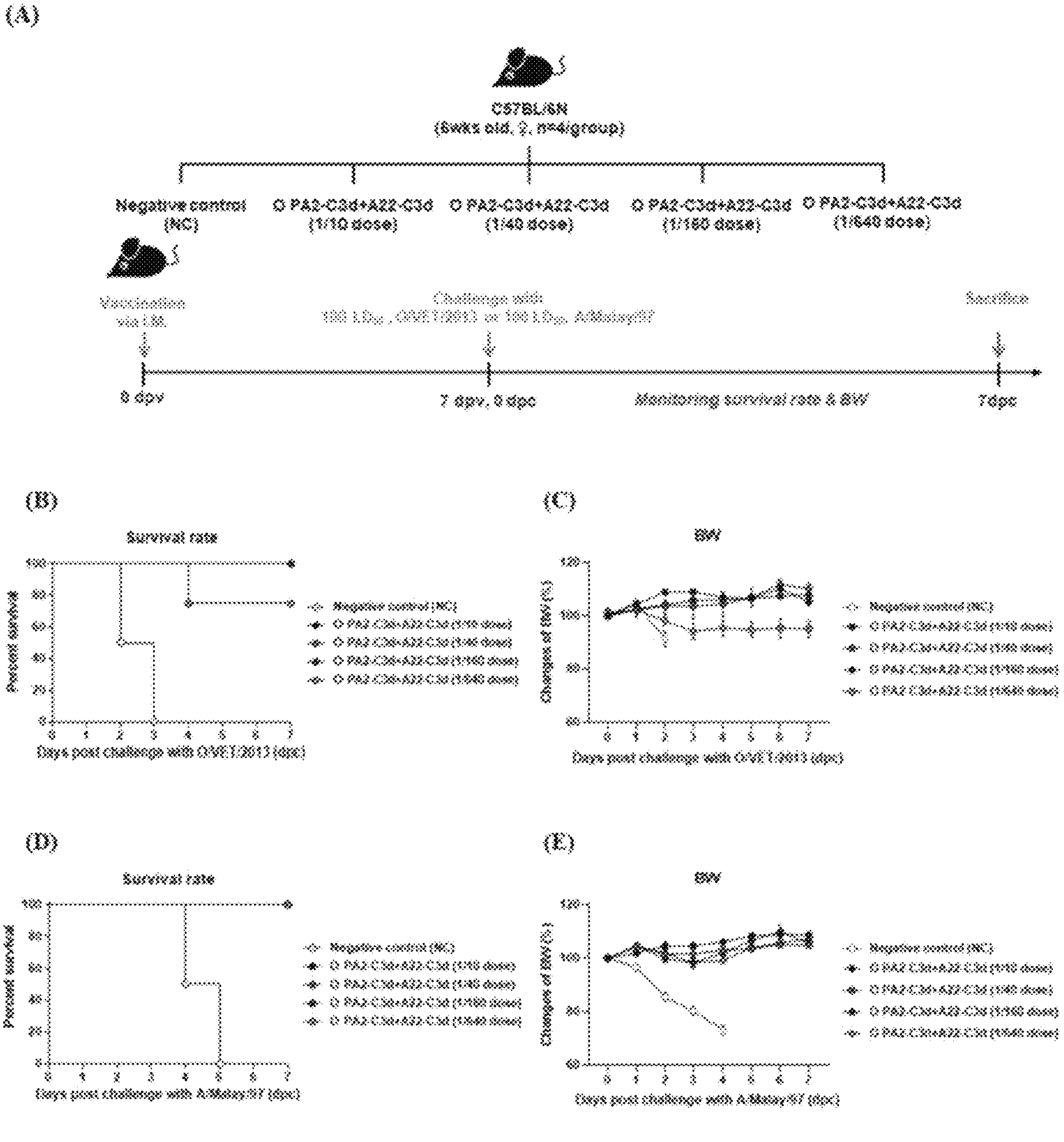
FIG. 5 shows the results of an evaluation on vaccination and immune response induction when vaccines include the antigens isolated and purified from the recombinant immune-boosting foot-and-mouth disease viruses type O and type A are administered to mice according to the present disclosure.

With the same experimental strategies as shown (A) in FIG. 5 and (A) in FIG. 3, mice were vaccinated via an I.M. injection at 0 dpv, and the mice were challenged with FMDVs (100 $LD_{50}$ from O/VET/2013, ME-SA topotype or 100 $LD_{50}$ from A/Malay/97, SEA topotype) administered via an I.P. Injection thereto at 7 dpv. Survival rates and body weight changes were monitored from 0 days post challenge (0 dpc) to 7 dpc.

The bivalent vaccine including the antigens of O PA2+A22 showed $PD_{50}$ ($Log_4$) values of 5.66 and 4 when the mice were challenged with O/VET/2013 and A/Malay/97, respectively ((B) and (D) in FIG. 3).

The bivalent vaccine including the antigens of O PA2-C3d+A22-C3d showed $PD_{50}$ ($Log_4$) values of 90.5 and >128 when the mice were challenged with O/VET/2013 and A/Malay/97, respectively ((B) and (D) in FIG. 5).

Figure 6A:
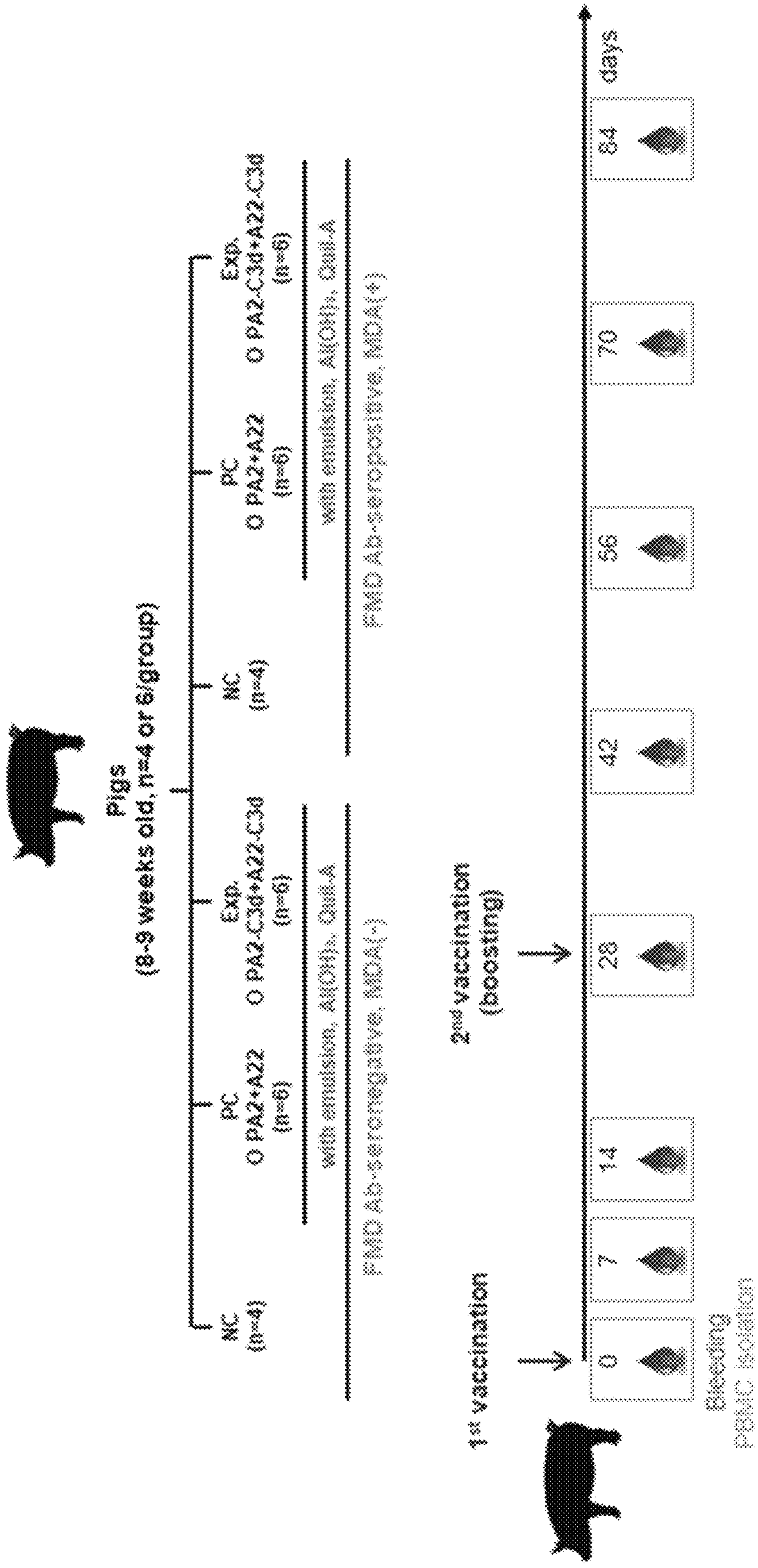
FIG. 6*a* shows a vaccination strategy when vaccines include the antigens isolated and purified from the recombinant immune-boosting foot-and-mouth disease viruses type O and type A are administered to pigs according to the present disclosure.

<Experiment Example 2> Evaluation of Immune Effect (Early, Mid-Term, Long-Term) in Target Animal (Pigs) of FMD Vaccine Including Antigens of PA2-C3d and A22-C3d, Immune-Boosting Foot-and-Mouth Disease Vaccine Strains for Overcoming Interference of Maternally-Derived Antibodies To evaluate the immunogenicity of antigens isolated and purified from O PA2-C3d and A22-C3d, the immune-boosting foot-and-mouth disease vaccine strains manufactured to overcome the interference of maternally-derived antibodies in the target animal, which was pigs and to observe the avoidance effect of overcoming the interference of maternally-derived antibodies, the experiments were performed using MDA(+) (FMD-seropositive)-wild pigs and MDA(−) (FMD-seronegative)-wild pigs, which were positive and negative for maternally-derived antibodies, respectively (FIG. 6*a*).

Figure 6B:
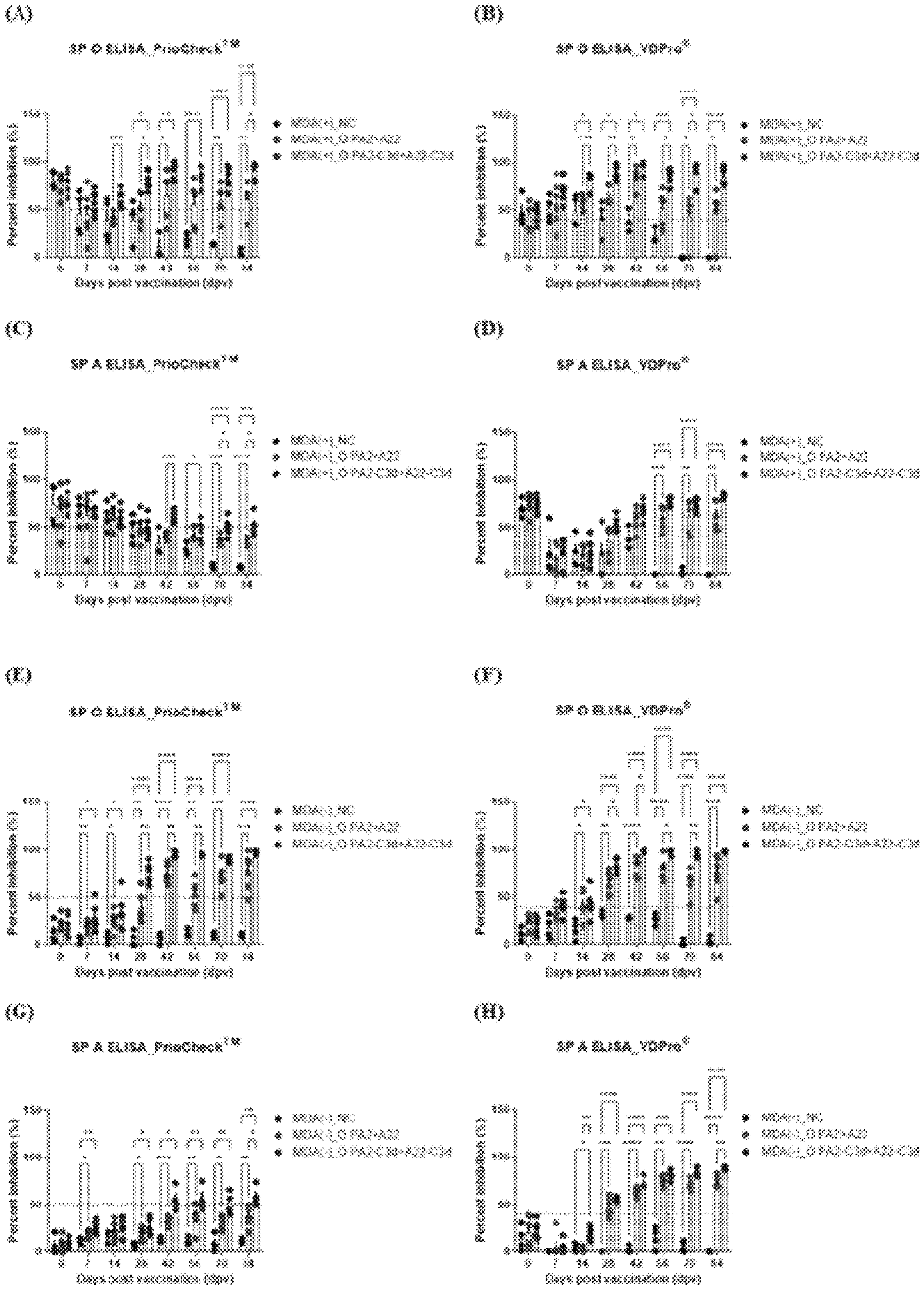
FIG. 6*b* shows the results of evaluation on early, mid-term, and long-term immunity (antibody titer induction by SP O ELISA and SP A ELISA) in pigs depending on vaccination when vaccines include the antigens isolated and purified from the recombinant immune-boosting foot-and-mouth disease viruses type O and type A according to the present disclosure.

As a result, when administering a test vaccine using the antigens of O PA2-C3d+A22-C3d to pigs in the MDA(+) group to confirm the effect of overcoming the interference of maternally-derived antibodies, from 14 dpv, the antibody titer by SP O ELISA in the MDA(+) group significantly increased compared to the PC group vaccinated with the test vaccine including the antigens of O PA2+A22 ($p<0.001$, PrioCheck™ kit, VDPro® kit), and even at 28 dpv, the antibody titer of the MDA(+) group showed significance of $p<0.05$ (PrioCheck™ kit) and $p<0.01$ (VDPro® kit) ((A) and (B) in FIG. 6*b*). In particular, after the second vaccination (boosting) of the test vaccine at 28 dpv, the antibody titer was very high in the experimental group. Meanwhile, in the NC group, maternally-derived antibodies continued to decrease. At 56, 70, and 84 dpv, the antibody titers of the experimental group and the NC group had a difference of $p<0.0001$ or $p<0.001$. Additionally, in the case of SP A ELISA in the MDA(+) group, at 42 dpv, the antibody titer of the experimental group was higher than the antibody titer of the PC group ($p<0.001$, PrioCheck IM kit). At 56, 70, and 84 dpv, significant differences between the experimental group and the NC group were observed at the $p<0.5$, $p<0.0001$, $p<0.001$ (PrioCheck™ kit), and $p<0.0001$ (VDPro® kit) levels, respectively ((C) and (D) in FIG. 6*b*).

Meanwhile, when administering the test vaccine to the MDA(−) group to confirm the immunogenicity and induction of early, mid-term, and long-term immunity in the target animal (pigs) of the test vaccine including the antigens of O PA2-C3d+A22-C3d, the antibody titer by SP O ELISA in the experimental group significantly increased compared to the NC group at the $p<0.05$ level at 7 dpv (PrioCheck™ kit) and 14 dpv (VDPro® kit), and from 28 dpv to 84 dpv, the antibody titer of the experimental group showed significance compared to the NC group ($p<0.0001$) ((E) and (F) in FIG. 6*b*). Looking at the antibody titers by SP A ELISA for each group in the MDA(−) group, the results were the same as the results shown by SP O ELISA. There was a significant difference in the antibody titers between the experimental group and the NC group at 7 dpv (PrioCheck™ kit) and 14 dpv (VDPro® kit) ($p<0.01$ and $p<0.05$), and from 28 dpv to 84 dpv, the experimental group showed a higher antibody titer than the NC group ($p<0.0001$, $p<0.001$, $p<0.01$, and $p<0.05$). In addition, the antibody titer of the experimental group was consistently higher than that of the PC group. The antibody titers of difference of the two groups had a significant difference observed at $p<0.01$ and $p<0.05$ (VDPro® kit) at 14 and 84 dpv ((G) and (H) in FIG. 6*b*).

Figure 7:
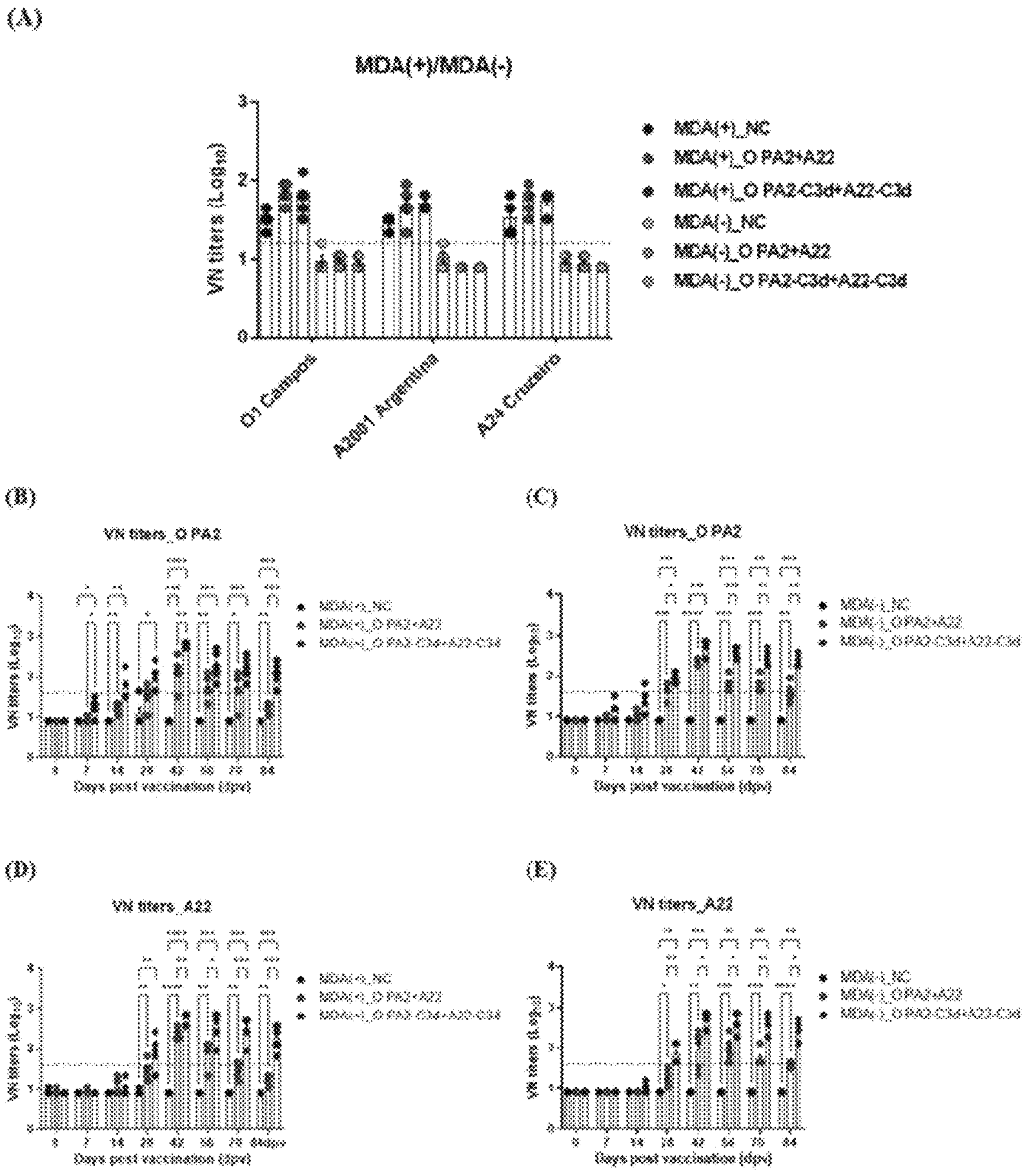
FIG. 7 shows the results of evaluation on early, mid-term, and long-term immunity (neutralizing antibody titer induction) in pigs depending on vaccination when vaccines include the antigens isolated and purified from the recombinant immune-boosting foot-and-mouth disease viruses type O and type A according to the present disclosure.

Before vaccination (0 dpv), neutralizing antibody titers against 01 Campos, A2001 Argentina, and A24 Cruzeiro in the MDA(+)/MDA(−) groups are shown (A) in FIG. 7. In the MDA(+) group, the neutralizing antibody titer was measured to be >1.6 $Log_{10}$, and in the MDA(−) group, the neutralizing antibody titer was measured to be <1.2 $Log_{10}$. The neutralizing antibody titers were confirmed using homologous viruses for O PA2 and A22, which were the backbone viruses used as antigens in the PC group ((B) and (C) in FIG. 7). In the case of the MDA(+) group, the antibody titers by SP O ELISA and SP A ELISA at 0 dpv were high, but the neutralizing antibody titers against O PA2 and A22 were low below the protective level ((B) in FIG. 7). This is believed to be due to the fact that the mother pigs of the piglets with high maternally-derived antibodies (MDA (+)) received the vaccine from Company B, showing low antibody titers against heterologous viruses such as O PA2 and A22.

In the case of the MDA(−) group, the neutralizing antibody titer against O PA2 ((C) in FIG. 7) was significantly higher in the experimental group, which was administered with the test vaccine including the antigens of O PA2-C3d+A22-C3d from 7 dpv, than in the NC and PC groups ($p<0.05$). Afterward, the neutralizing antibody titer of the experimental group continued to increase until 14 and 28 dpv (p<0.01 and p<0.05), and after boosting at 28 dpv, the neutralizing antibody titer increased higher compared to the NC group from 42 dpv to 84 dpv (p<0.0001, p<0.001, p<0.01, and p<0.05). In addition, even after boosting, the neutralizing antibody titer of the experimental group was higher than that of the PC group, and the antibody titers between the two groups had a significant difference observed at 42 dpv and 84 dpv (p<0.001 and p<0.01).

Looking at the neutralizing antibody titers against A22 in the MDA(+) and MDA(−) groups ((D) and (E) in FIG. 7), the neutralizing antibody titers in the experimental group at 28 dpv were higher than in the NC and PC groups (p<0.01), and after boosting, from 42 dpv to 84 dpv, the neutralizing antibody titers of the experimental group increased to a higher level than those of the NC group (p<0.0001 and p<0.001). The neutralizing antibody titers of the experimental group and the PC group had a significant difference from 42 dpv to 84 dpv (p<0.0001 and p<0.001).

Figure 8A:
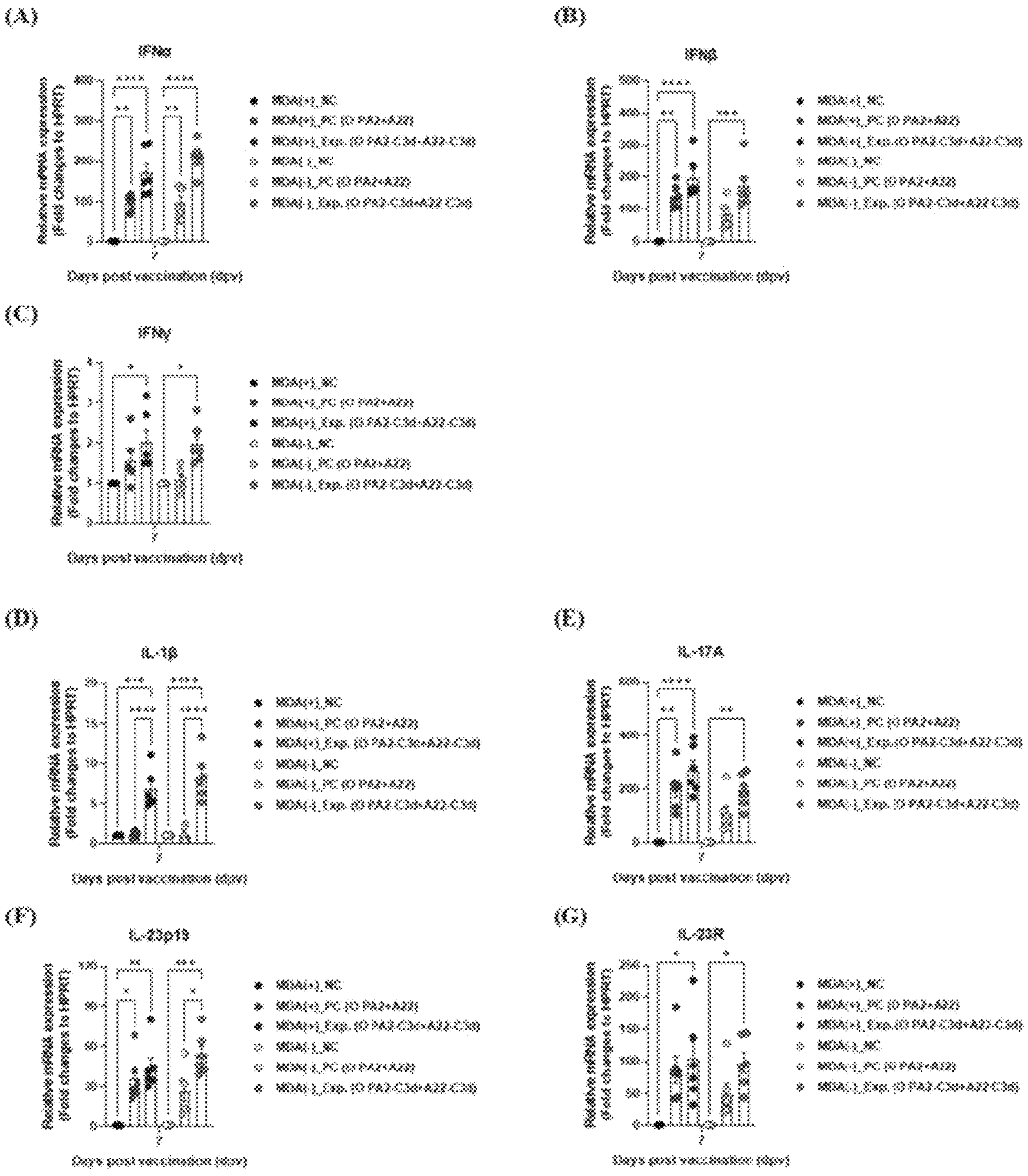
FIGS. 8*a* to 8*c* show the results of evaluation on the expression of cellular immune response genes (cytokines and costimulatory molecules) in pigs depending on vaccination when vaccines include the antigens isolated and purified from the recombinant immune-boosting foot-and-mouth disease viruses type O and type A according to the present disclosure.
Figure 8B:
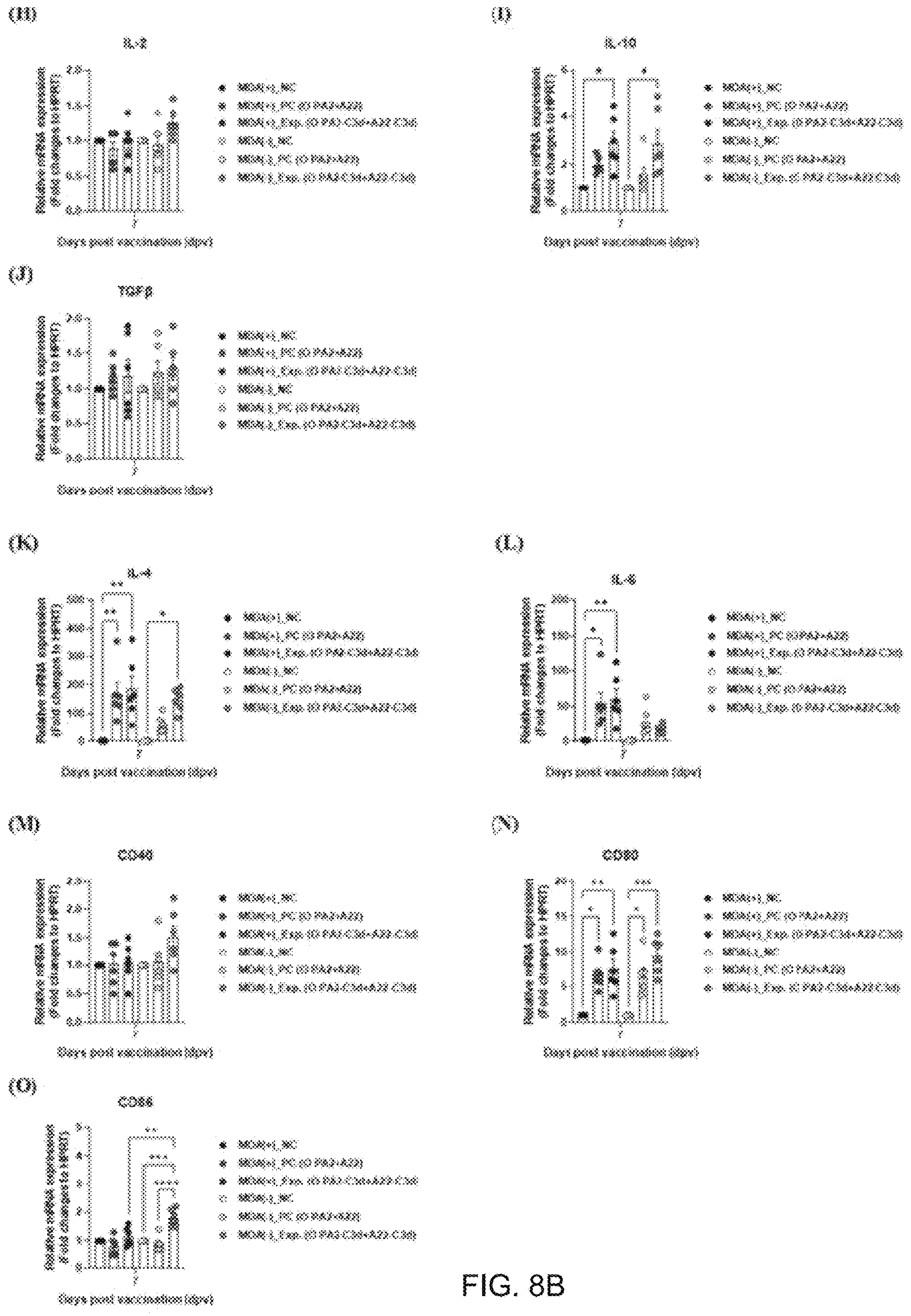
Figure 8C:
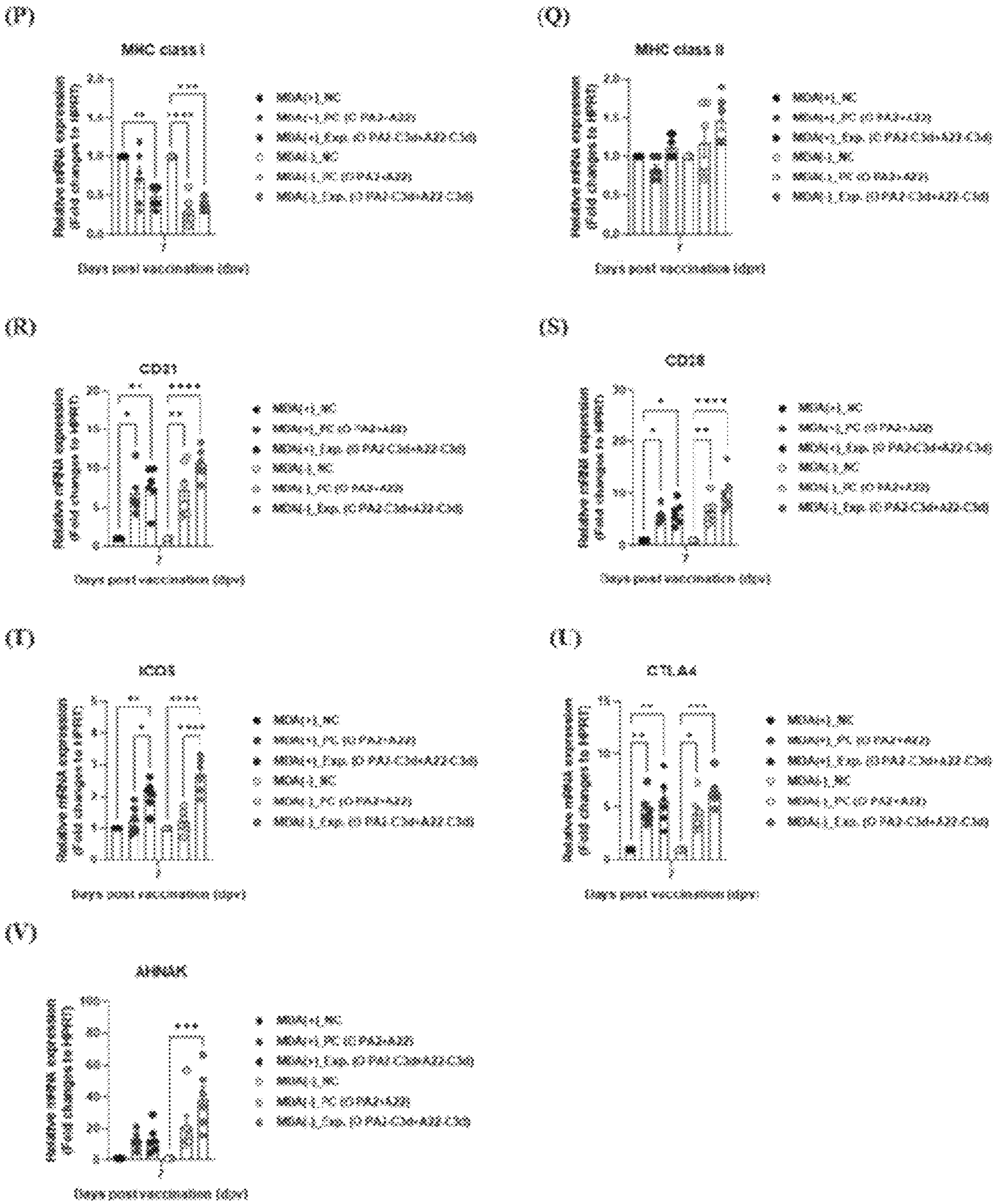

<Experiment Example 3> Evaluation of Induction of Cellular Immune Responses in Pigs by FMD Vaccine Including Antigens of O PA2-C3d and A22-C3d, Immune-Boosting Foot-and-Mouth Disease Vaccine Strains for Overcoming Interference of Maternally-Derived Antibodies 3-1. As shown in FIG. 6*a*, after vaccinating the target animal, which was pigs, with a test vaccine including the antigens of O PA2-C3d and A22-C3d, at each sampling time, PBMCs were isolated from the whole blood of the pigs, and qRT-PCR was performed. Afterward, observed were changes in the expression of genes for cytokines (IFNα, IFNβ, IFNγ, IL-1β, IL-17A, IL-23p19, IL-23R, IL-2, IL-10, TGFβ, IL-4, and IL-6) and co-stimulatory molecules (CD40, CD80, CD86, MHC class I, MHC class II, CD21, CD28, CTLA4, ICOS, and AHNAK), both of which were related to the induction of cellular immune responses (FIGS. 8*a* to 8*c*).

As a result, overall, the expression of proinflammatory cytokine genes was observed to be very high. In particular, when experimenting with individuals in the MDA(+)/MDA(−) conditions, the expressions of type I IFNs, IFNα, and IFNß had a very high increase of the p<0.0001 and p<0.001 levels in the experimental group compared to the NC group at 7 dpv. Meanwhile, looking at the difference between the PC group and the NC group, the expression of IFN was higher in the PC group than in the NC group in both MDA(+)/MDA(−) conditions (p<0.01). However, the expression of IFNβ in the PC group had a significant increase compared to the NC group only in the MDA(+) condition (p<0.01). The expression of IFNγ was somewhat lower than the expressions of IFNα and IFNβ, but a significantly higher expression was observed in the experimental group compared to the NC group in both MDA(+)/MDA(−) conditions (p<0.05).

The expression of IL-1β was significantly higher in the experimental group than in the NC group in MDA(+)/MDA(−) conditions (p<0.0001 and p<0.001), in particular, compared to the PC group, the expression of IL-1β in the experimental group showed a significant difference at the p<0.0001 level. The expression of IL-17A was much higher in the experimental group than in the NC group in MDA(+)/MDA(−) conditions (p<0.0001 and p<0.01), and the significance in the expression of IL-17A was observed between the PC and NC groups in the MDA(+) condition (p<0.01). The expression of IL-23p19 was also significantly higher in the experimental group than in the NC group in MDA(+)/MDA(−) conditions (p<0.01 and p<0.001), in particular, the expression of IL-23p19 between the experimental group and PC group was significantly different in the MDA(−) condition (p<0.05). The expression of IL-23R was also very high, as were the expressions of other cytokines. In both MDA(+)/MDA(−) conditions, the expression of IL-23R showed a significant difference between the experimental group and the NC group (p<0.05). The expression levels of IL-4 and IL-6 were higher in the MDA(+) condition than in the MDA(−) condition. In the MDA(+) condition, the significance in the expression of IL-4 and IL-6 was at p<0.01 between the experimental group and the NC group. The significance in the expression of IL-4 and IL-6 was at p<0.01 and p<0.01, respectively, between the PC group and the NC group. In the MDA(−) condition, the expression level of IL-4 between the experimental group and the NC group had a significant difference observed at p<0.05. Meanwhile, the expression of IL-10, which was an anti-inflammatory cytokine, was found to be higher in the experimental group than in the NC group in MDA(+)/MDA(−) conditions (p<0.05). The expression levels of IL-2 and TGFβ were higher in the order of the experimental group>the PC group>the NC group, but no significance was observed between each group.

The expression levels of co-stimulatory molecules were overall somewhat lower than the expression levels of cytokines, but it was confirmed that the expression levels of co-stimulatory molecules were significantly increased in the experimental group compared to the PC group or NC group. The expression of CD80, CD21, CD28, CTLA4, and ICOS tended to increase upon vaccine administration in the MDA(−) condition compared to the MDA(+) condition. The expression of CD80, CD21, CD28, CTLA4, and ICOS showed significance between the experimental group and the NC group in MDA(+)/MDA(−) conditions (p<0.0001, p<0.001, p<0.01, and p<0.05). The expressions of the remaining genes except ICOS between the PC group and the NC group showed significance observed at the p<0.01 and p<0.05 levels. Among the gene expressions, the expressions of CD80, CD21, and CD28 showed very high changes due to test vaccine administration. The expression of ICOS between the experimental group and the PC group showed significance at p<0.01 in the MDA(+) condition and p<0.0001 in the MDA(−) condition, which means the expression of ICOS was higher in the C3d-inserted strain compared to the backbone strain.

The expressions of CD86 and AHNAK between the experimental group and NC group in the MDA(−) condition showed significance (p<0.0001 and p<0.001), in particular, the expression of CD86 between the experimental group and the PC group showed a significant difference (p<0.0001). Meanwhile, the expression level of MHC class I was found to be reduced in the MDA(−) condition compared to the MDA(+) condition. The expression of CD40 and MHC class II between each group showed no significance.

3-2. Humoral immune responses mediated by the immune-boosting foot-and-mouth disease virus types O and A (O PA2-C3d and A22-C3d) according to the present disclosure, as measured by immunoglobulin subtypes such as IgG, IgM, and IgA in pigs are as follows.

Pigs (8 to 9 weeks old) that were FMD antibody-negative (MDA(+), n=16) or FMD antibody-negative (MDA(−), n=16) were divided into three groups each. A negative control group (NC, n=4/group), a positive control group (PC, n=6/group), and an experimental group (Exp., n=6/group).

The experimental group was administered with a test vaccine including 15 μg (1 dose for cattle and pigs) of O PA2-C3d+A22-C3d antigen plus ISA 206 (oil-based emulsion, 50%, w/w), 10% $Al(OH)_3$, and 150 μg Quil-A. The positive control (PC) group was administered with a test vaccine including 15 μg (1 dose for cattle and pigs) of O PA2-C3d+A22-C3d antigen plus ISA 206 (oil-based emulsion, 50%, w/w), 10% $Al(OH)_3$, and 150 μg Quil-A. The negative control (NC) group was administered with the same volume of PBS as a test vaccine. Vaccination was performed twice at a 28-day interval. 1 mL vaccine (1 dose) was injected into the test animal's neck via a deep intramuscular route. For serological assays, blood samples were collected from the pigs at 0, 7, 14, 28, 42, 56, 70, and 84 days after vaccination, and the experimental results are shown in FIG. 8*d*.

Figure 8D:
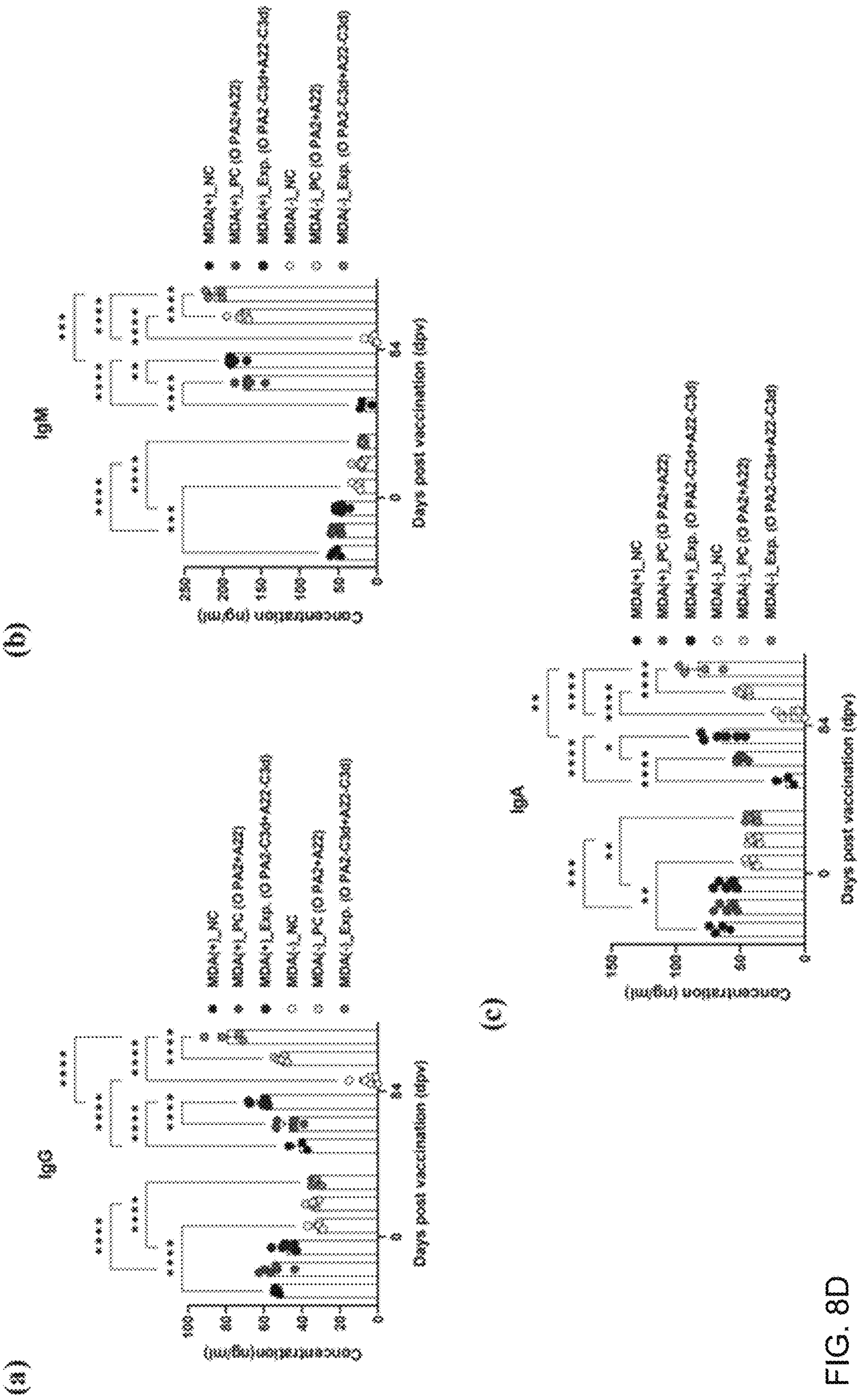
FIG. 8*d* shows the results of evaluation on the induction of humoral immune responses (immunoglobulin subtypes such as IgG, IgM, and IgA) mediated by vaccination in pigs when vaccines include the antigens isolated and purified from the recombinant immune-boosting foot-and-mouth disease viruses type O and type A according to the present disclosure.

In FIG. 8*d*, (A) shows IgG concentration; (B) shows IgM concentration; and (C) Shows IgA concentration. Data represent mean±SEM of triplicate measurements (n=4 or 6/group). Statistical analysis was performed using two-way ANOVA followed by Tukey's test. *$p<0.05$; $p<0.01$; *$p<0.001$; and ****$p<0.0001$.

As a result of the experiments, O PA2-C3d and A22-C3d were effectively induced in MDA(+)/MDA(−) animals when with not only SP-specific antibody titers (via SP ELISA) but also SP-non-specific antibodies including IgG (indicator of neutralizing antibodies), IgM (first natural antibody induced during pathogen infection or vaccination), and IgA (core element inducing mucosal immunity) levels. Maternal IgG and IgA may attenuate mucosal helper cell responses in early infancy, and maternal IgG regulatory T cell epitopes induce immune tolerance rather than immunogenicity. Based on the results, the recombinant immune-boosting foot-and-mouth disease vaccine strains O PA2-C3d and A22-C3d can effectively induce active immunity in the host by overcoming MDA interference-mediated immune tolerance in MDA(+) animals. In addition, the vaccine strains may induce robust cellular and humoral immune responses when vaccinated into MDA(−) animals or animals at the ages of 2 to 3 months (period of lower MDA titers depending on the current vaccination program). These results suggest that C3d spikes on antigens directly activate B cells by persistently stimulating B cell surface receptors and that the highly immunogenic O PA2-C3d and A22-C3d antigens provide a robust T cell-mediated immune response, generating more efficient high titers and neutralizing antibodies (FIG. 8*d*).

From the results, it was determined that O PA2-C3d and A22-C3d, as immune-boosting foot-and-mouth disease vaccine strains, have excellent immunogenicity of the antigens themselves and play an important role in inducing short-term immunity and initial host defense. In addition, it is expected that the O Bivalent test vaccine including the antigens of PA2-C3d antigen+A22-C3d will be more effective in overcoming the interference of maternally-derived antibodies by simultaneously inducing a robust cellular immune response and humoral immune response in the early stage when vaccinating the target animal.

<Experiment Example 4> Evaluation of Effectiveness in Pigs of Overcoming Interference of Maternally-Derived Antibodies and Simultaneously Inducing Cellular and Humoral Immune Responses To evaluate the effectiveness of overcoming the interference of maternally-derived antibodies and simultaneously inducing cellular and humoral immune responses in pigs, experiments involving MDA(+)- or MDA(−)-pigs were performed (FIG. 6*a*). In the MDA(+)-individuals, O PA2-C3d+A22-C3d especially showed a strong effect of overcoming maternally-derived antibodies through antibody titer induction by SP O ELISA. In the case of antibody titer by SP A ELISA, the antibody titer itself decreased somewhat at the beginning of vaccination and then tended to increase after boosting. This is determined that due to the nature of the FMDV type A antigens, the FMDV type A antigens have a different SP region from the antigen coated on the SP A ELISA plate, so the detection itself appeared low, affecting the percent inhibition (PI) value. For a more accurate evaluation, it was deemed necessary to review whether it was possible to overcome the interference of maternally-derived antibodies through VN titers.

Meanwhile, in the MDA(−)-individuals, O PA2-C3d+A22-C3d induced a strong increase in antibody titers by SP O ELISA and SP A ELISA, and the ability to induce antibody titers was significant compared to O PA2+A22 used as backbone (FIG. 8*b*).

Additionally, to confirm the actual virus neutralization effect, VN titers for O PA2 and A22 were confirmed. Since the individuals in question were vaccinated with a vaccine from Company B (the source of the commercialized vaccine is not listed to protect the company's rights and interests and prevent disputes), to confirm the presence of maternally-derived antibodies, VN titers for 01 Campos, A2001 Argentina, and A24 Cruzeiro were confirmed using a serum at 0 dpv before vaccination. As a result, the VN titers for the MDA(+) group and MDA(−) group were accurately classified as positive and negative, respectively, and vaccination was performed for each group using these animals.

As a result of confirming the VN titers for O PA2 and A22 using the serum from 0 to 84 dpv at each blood collection time, the antigens of the vaccine strains in the vaccines inoculated into mother pigs were different from the antigens in the vaccines inoculated in the present disclosure, and thus regardless of the MDA(+)/MDA(−) groups, VN titers for O PA2 and A22 were <1.2 $Log_{10}$, which is below the defense level in the initial stage (0 dpv). In both maternally-derived antibody positive/negative groups, the administration of the O PA2-C3d+A22-C3d bivalent test vaccine showed significantly high VN titers compared to the administration of the O PA2+A22 bivalent test vaccine (FIG. 7).

From the results, O PA2-C3d and A22-C3d, the immune-boosting foot-and-mouth disease vaccine strains developed to overcome the interference of maternal-derived antibodies, are expected to effectively induce active immunity in the host by overcoming interference phenomena such as immune tolerance even in the presence of maternally-derived antibodies. In addition, depending on the antivirus program currently in use, the vaccine strains are believed to induce a robust humoral immune response even when inoculated into the target animal (pigs) at the ages of 8 to 12 weeks, when maternally-derived antibodies are decreasing. This is determined that since C3d spiked on the antigen continuously stimulates B cell surface receptors to directly activate B cells, while the highly immunogenic O PA2-C3d antigens and A22-C3d antigens induce a strong T cell-mediated cellular immune response, more efficient production of high titer antibodies and neutralizing antibody titers is possible.

To prove this, a bivalent test vaccine including the antigens of O PA2-C3d+A22-C3d was used to confirm the O PA2-C3d+A22-C3d antigen-mediated cellular immune response in MDA(+)/MDA(−) pigs. The positive control (PC) group received a bivalent test vaccine including the antigens of the backbone strain O PA2+A22, and the negative control (NC) group received PBS. In both MDA(+)/

MDA(−) conditions, the test vaccine including the antigens of O PA2-C3d+A22-C3d induced a very high level of expression of type I IFN, which had an antiviral effect at the beginning of vaccination (7 dpv). Thus, the test vaccine was expected to be able to effectively protect the host in the early stages of vaccination against FMDV infection. In the case of IFNγ, a T helper (Th) 1 cell-related cytokine, the expression level thereof was lower than the expression levels of IFNα and IFNß, but a significant expression of >2 fold-change ($p<0.05$) was shown, so it was determined that IFNγ effectively induced T cell-mediated cellular immune responses. It was found that the expression of IL-1β, which is involved in the activity of inflammasomes, the expression of Th17 cells, and the expression of IL-17A derived from unconventional T cells (γδ T cells) were also very high in the experimental group inoculated with the antigens isolated and purified from the C3d-inserted vaccine strains. Through previous research by the current inventors, the expressions of IL-23p19 and IL-23R were found to be very important in the host's initial defense. In such a situation, in the present disclosure, the IL-23p19 and IL-23R were initially expressed at the level of a 'cytokine storm' and then the expressions appeared to normalize.

When IL-23A is secreted through stimulation of pathogen recognition receptors (PRRs) in innate immune cells such as dendritic cells (DCs) and macrophages (M$^{\Phi}$S), IL-23A binds to IL-23R on the surface of non-traditional T cells, which are innate-like immune cells, and stimulates the cells to produce IL-17A. The produced IL-17A plays a critical role in the host's initial defense by recruiting neutrophils to the site of pathogen infection, forming a neutrophil extracellular trap (NET), and causing NETosis of the pathogen.

In addition, the IL-23/IL-17A axis is known to link innate immunity and adaptive immunity. It is believed that the test vaccine including the antigens of O PA2-C3d+A22-C3d simultaneously induces innate and adaptive immune responses through the secretion of these pro-inflammatory cytokines.

TGFβ, which is known to play a central role in the differentiation and survival of $CD4^{+}$ Th subsets and $CD4^{+}$ T regulatory cells ($T_{regs}$) and to be involved in the development of $T_{regs}$ and the induction of immunological tolerance in DCs with IL-2, a T cell growth factor essential for the generation of memory cells, had a slight high expression in the experimental group, but no significance was observed between each group. The expression of IL-10, an anti-inflammatory cytokine, was also significantly increased in the experimental group ($p<0.05$), which is presumed to be due to host homeostasis to control the 'cytokine storm' of inflammatory cytokines. The expressions of Th2 cell-derived cytokines, IL-4 and IL-6, were higher in the MDA(+) group than in the MDA(−) group, and the expressions of these cytokines increased in the presence of passive immunity by maternally-derived antibodies.

It is determined that CD80 and CD86 co-stimulatory signaling, which cooperates with T cell receptor (TCR) signaling to promote activation of T cells, increased in the O PA2-C3d+A22-C3d administration group, thereby the immune-boosting foot-and-mouth disease vaccine strains can effectively stimulate T cells by effectively presenting antigens to T cells.

In the case of MHC class I, gene expression was higher in the MDA(+) group than in the MDA(−) group and lower in the vaccinated group than in the NC group. It is determined that in the presence of passive immunity, MHC class I gene expression appeared to be low, thereby inhibiting antigen recognition by cytotoxic CD8+ T cells in the early stages of vaccination. Meanwhile, MHC class II had a higher expression thereof in the MDA(−) group compared to the MDA(+) group, and although no significance between groups was shown, the expression of MHC class II tended to increase in the experimental group. From this, it is determined that the antigens of the C3d inserted immune-boosting vaccine strains activate CD4+ T cells, which induce cooperation and regulation of effector cells through the presentation of MHC class II by APC (DCs, M$^{\Phi}$s, and B cells). It is determined that the antigens of the C3d-inserted immune-boosting vaccine strains may induce the formation of continuous cell-cell contact and activation of T cells through interaction with the MHC complex.

Meanwhile, the expression of CD21, a direct C3d receptor, was significantly increased in both MDA(+)/(MDA(−) conditions by vaccination with a test vaccine containing the antigens of C3d-inserted foot-and-mouth disease vaccines ($p<0.01$ and $p<0.0001$), thereby activation of B cells appeared to be possible through stimulation of C3d on the surface of FMDVs and binding to CD21.

The expressions of CD28 and ICOS, co-stimulatory signals that are co-stimulated upon T cell activation and play an important role in the induction of memory T cells, increased significantly in MDA(+)/MDA(−) conditions by vaccination with the test vaccine containing the antigens of O PA2-C3d+A22-C3d (CD28: $p<0.0001$; $p<0.05$; ICOS: $p<0.01$; $p<0.00001$). In particular, the expression of ICOS induced a significant difference between the experimental group and the PC group (MDA(+): $p<0.05$; MDA(−): $p<0.0001$). It appears that the antigens of C3d-inserted foot-and-mouth disease vaccine strains increased co-stimulation of T cells and lymphocytes and induced significant expression of IFNγ. Additionally, ICOS is known to affect the intestinal immune relationship for IgA production as an immunoglobulin domain, thereby ICOS is expected to be used for a foot-and-mouth disease vaccine in the future to simultaneously induce systemic immunity and mucosal immunity. The expression of CTLA4 also showed a similar trend to the expression of ICOS. The CTLA pathway is thought to be induced by the expression of ICOS, meanwhile, when administering foot-and-mouth disease vaccines to overcome the interference of maternally-derived antibodies in the cytoplasmic domain, the induced CTLA4 causes the conversion of regulatory T cells to suppress autoimmunity by expressing pro-inflammatory cytokines at the level of a 'cytokine storm'.

Meanwhile, in the present disclosure, the expression of AHNAK was significantly increased in the O PA2-C3d+A22-C3d administration group in the MDA(−) condition ($p<0.001$) and was somewhat higher in the experimental group in the MDA(+) condition. However, no significance was observed between each group. AHNAK is a large 700 kDa protein previously identified as a structural scaffold protein. AHNAK has been involved in various cellular processes such as cell structure, intracellular trafficking, cell membrane regeneration, regulated exocytosis, T cell differentiation, and calcium signaling pathways during T cell activation.

Cytolytic $CD8^{+}$ T cells (CTLs) kill virus-infected cells in a calcium-dependent manner. AHNAK is expressed in mature CTLs, but not in naïve $CD8^{+}$ T cells. It has been reported that calcium introduction is very important for proper function to induce an immune response. In fact, ANHAK-deficient (Ahnak1$^{-/-}$) CTL caused a significant decrease in Granzyme B production, cytolytic activity, and IFNγ secretion after TCR stimulation.

Thus, it is thought that the test vaccine including the antigens of O PA2-C3d+A22-C3d can induce T cell activation and CTL response through the expression of AHNAK.

In addition, to verify that the antigens of immune-boosting foot-and-mouth disease viruses according to the present disclosure induce secretion of IFNγ, an indicator of cellular immune response and to verify a specific cellular immune response to be induced by the C3d-inserted FMDV antigens, Ag-mediated secretion of IFNγ by 'C3d' inserted FMDVs was confirmed through in vitro ELISpot analysis using peritoneal exudate cells (PECs) isolated from mouse peritoneal lavage fluid and peripheral blood mononuclear cells (PBMCs) isolated from pig whole blood.

Figure 8E:
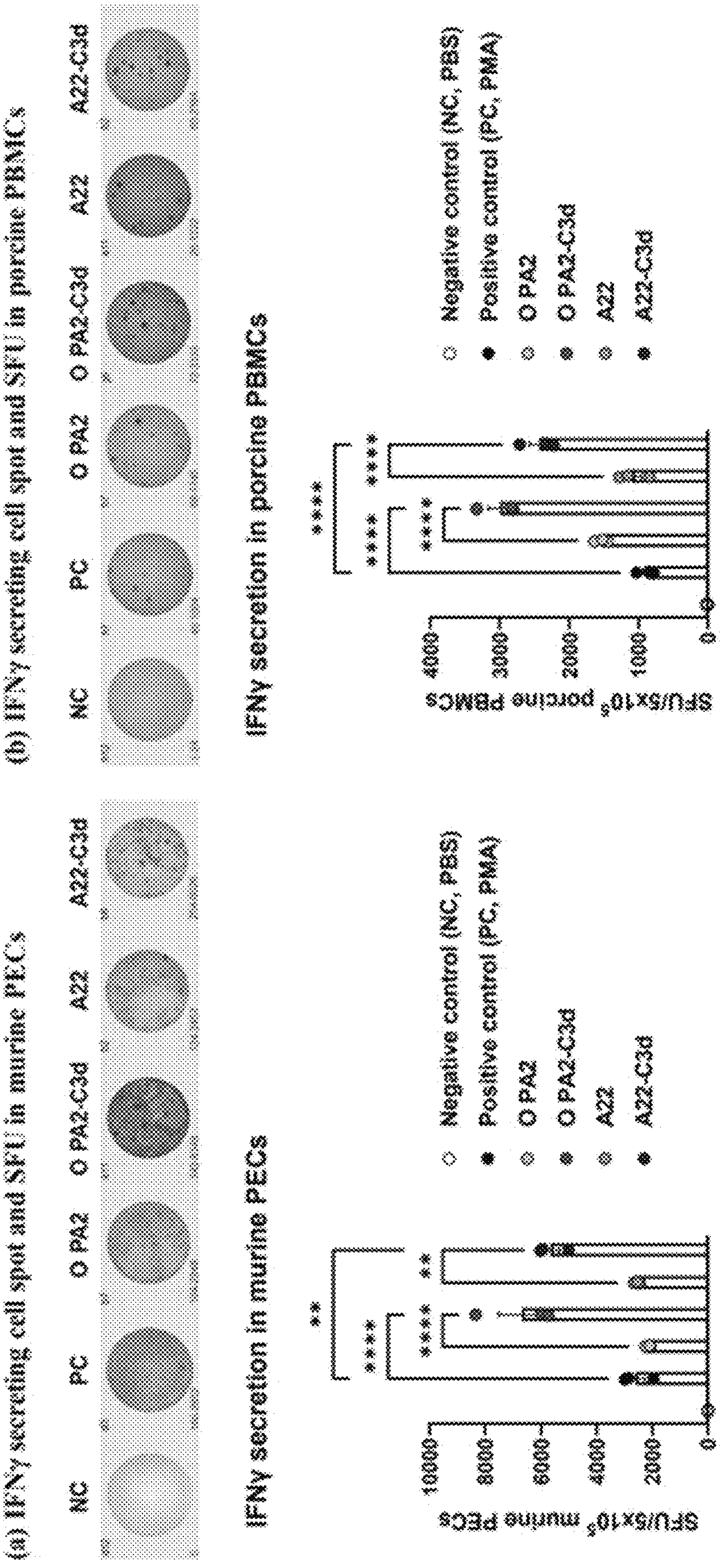
FIG. 8*e* shows the results of cellular immune responses in murine peritoneal exudate cells (PECs) and porcine peripheral blood mononuclear cells (PBMCs) induced by treatment of the antigens isolated and purified from the recombinant immune-boosting foot-and-mouth disease viruses type O and type A according to the present disclosure.

As a result, the antigens of the inactivated FMDVs from O PA2-C3d and A22-C3d induced significantly higher levels of IFNγ secretion than control groups on mouse PEC and porcine PBMC (FIG. 8*e*). All in all, these results demonstrate that O PA2-C3d and A22-C3d may induce a Th1-type immune response.

Figure 9:
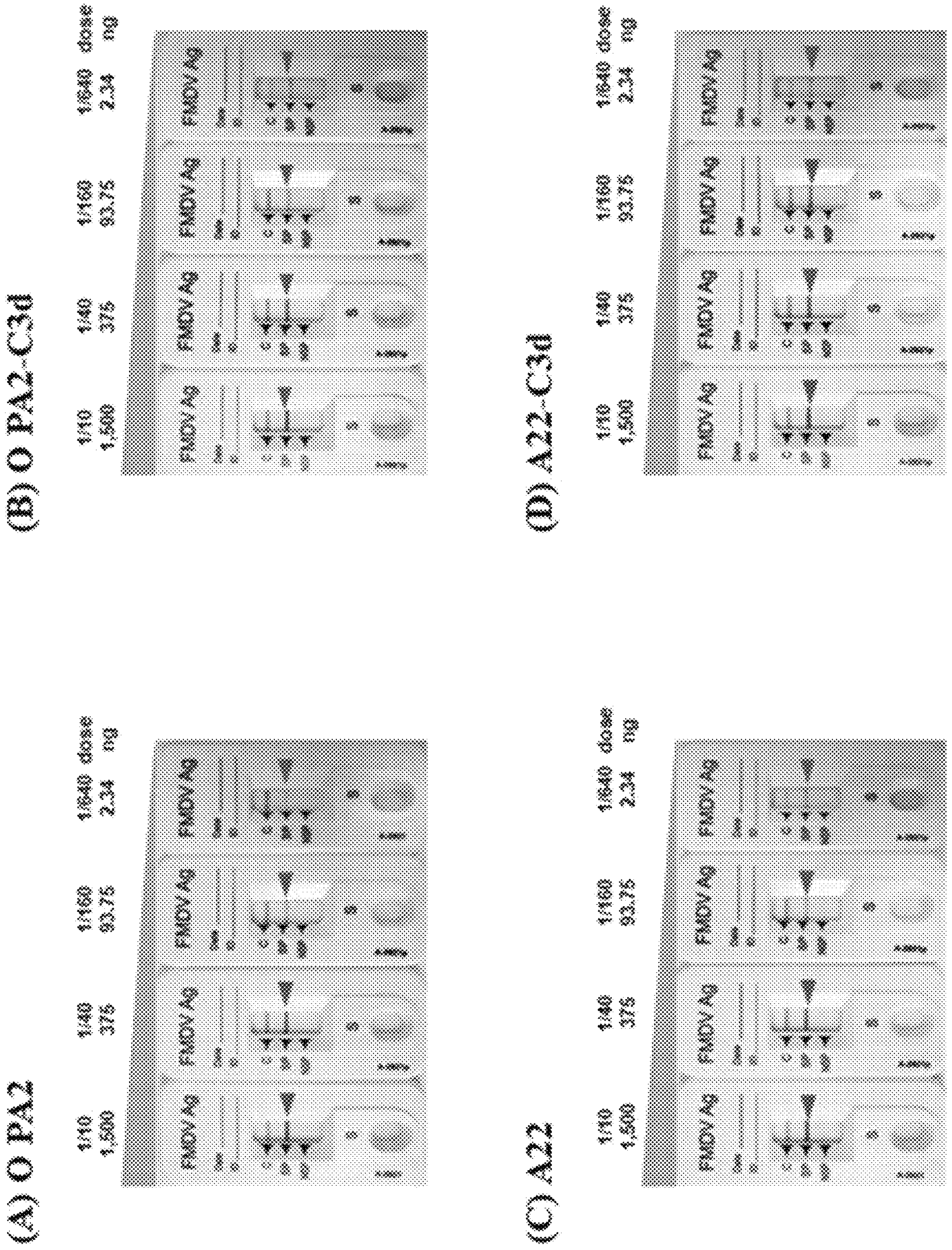
FIG. 9 shows the results of measuring an antigen amount in a simple kit including the antigens isolated and purified from the recombinant foot-and-mouth disease viruses according to the present disclosure and of differentiating vaccine strains of the present disclosure from wild strains.
Figure 10:
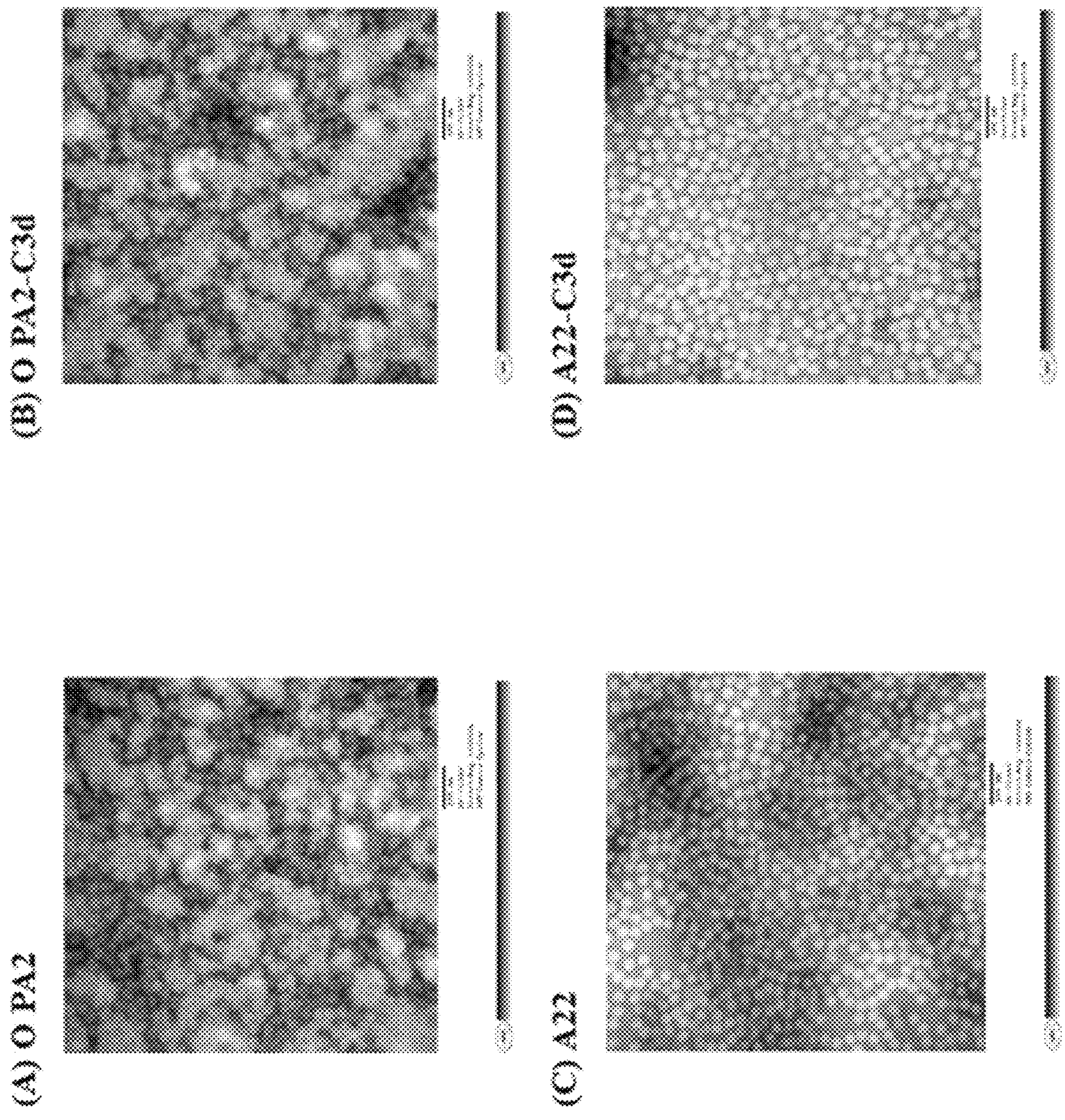
FIG. 10 shows the results of electron microscopy (TEM) observation of the antigens (146s particle) purified using the recombinant foot-and-mouth disease viruses according to the present disclosure.

<Experiment Example 5> Evaluation of Possibility of Measuring Antigen Content in a Simple Kit and Differentiating Vaccine Strains from Wild Strains Inactivated antigens were produced and purified using two types of recombinant foot-and-mouth disease viruses, O PA2-C3d and A22-C3d, prepared according to the present disclosure and using two types of backbone viruses, O PA2 and A22, for positive control (PC) group. As a result of measuring the antigen content using a simple kit and performing a differentiation test from wild strains using these virus strains, a positive SP band was confirmed even with a small amount of 2.34 ng (1/640 dose), and it was found that it was possible to differentiate the virus strains from wild strains through the absence of an NSP band (FIG. 9). As a result of electron microscopy (TEM) observation of the antigens (146s particles) purified through a sucrose density gradient, it was confirmed that there was no problem in the formation of 146s particles, thereby the antigens were used as antigens for a foot-and-mouth disease test vaccine (FIG. 10).

The invention claimed is:

1. A recombinant plasmid comprising a sequence represented by SEQ ID NO: 11.

2. A recombinant immune-boosting foot-and-mouth disease virus type A prepared from the recombinant plasmid of claim 1.

3. An antigen of a recombinant immune-boosting foot-and-mouth disease virus type A, wherein the antigen is obtained by purifying and isolating the recombinant immune-boosting foot-and-mouth disease virus of claim 2.

4. A foot-and-mouth disease vaccine composition comprising the recombinant immune-boosting foot-and-mouth disease virus of claim 2 or the antigen of the recombinant immune-boosting foot-and-mouth disease virus of claim 3.

5. A foot-and-mouth disease diagnostic kit comprising the recombinant immune- boosting foot-and-mouth disease virus of claim 2 or the antigen of the recombinant immune-boosting foot-and-mouth disease virus of claim 3.

* * * * *

SEQUENCE LISTING

```
Sequence total quantity: 59
SEQ ID NO: 1           moltype = DNA  length = 11097
FEATURE                Location/Qualifiers
source                 1..11097
                       mol_type = genomic DNA
                       organism = Foot-and-mouth disease virus
SEQUENCE: 1
ctaaattgta agcgttaata ttttgttaaa attcgcgtta aatttttgtt aaatcagctc  60
atttttaac caataggccg aaatcggcaa aatcccttat aaatcaaaag aatagaccga  120
gatagggttg agtgttgttc cagtttggaa caagagtcca ctattaaaga acgtggactc  180
caacgtcaaa gggcgaaaaa ccgtctatca gggcgatggc ccactacgtg aaccatcacc  240
ctaatcaagt tttttggggt cgaggtgccg taaagcacta aatcggaacc ctaaagggag  300
cccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac  420
cacacccgcc gcgcttaatg cgccgctaca gggcgcgtcc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc atatgtaata cgactcacta tagggttgaa agggggcgct  660
agggtctcac ccctagcatg ccaacgacag ctcctacgtc gcactccaca ctaacgtttg  720
tgtgcgcgcg ggaaccgatg gacttttgtt cacccaccta cagttggact cacggcaccg  780
cgtggccatt ttagctgggt tgtgcggacg aacactgctt gcgcatctcg cgtgaccggt  840
tagtactctt accactatcc gcctacttgg tcgttagcgc tgtcctgggc actcttgttg  900
ggggctgttc aacgctctac ggtctcccct gcgtaacaga ctacggtgtt ggggccgctt  960
cgtgcgagcc gatcgcttgg tgtgcctcgg ctgtcgcccg aagcccgcct ttcacccccc  1020
cccccccccc cccccctaggt tttaccgtcg ttcccgacgt taatggggaa acaaccacaa  1080
gcttaacacc gtcttgcccg acgtaaaagg gctgcaacca aaaagcttgt gccgcctttc  1140
ccggcgttaa tgggaggtaa ccacaagaca aaccttcacc cggaagtaaa acggcaactt  1200
cacacagttt tgcccgtttt cgtgagaaat gggccgtcaa cgcacgaaac gcgccgtcgc  1260
ttgaggagga cttgtacaaa cacgatctat gcaggtttcc acaactgaca caaaccgtgc  1320
aacttgaaac cccgcctggt ctttccaggt ctagaggggc gacattttgt actgtgcttg  1380
actccacgct cggtccacta gcgagtgtta gtagtagcac tgttgcttcg tagcggagca  1440
tgatggccgt gggagcttcc ccttggtaac aaggacccac ggggccaaaa gccacgtcct  1500
accggaccca tcatgtgtgc aaacccagca cggcaacttt actgcgaaaa ccactttaag  1560
gtgacactga tactggtact caatcactgg tgacaggcta aggatgccct tcaggtaccc  1620
cgaggtaaca cgcgacactc gggatctgag aaggggactg ggcttcttt aaaagtgccc  1680
agtttaaaaa gcttctatgc ctgaataggc gaccggaggc cggcgccttt tcactgtttt  1740
actactgttt tcatgaatac aactgactgt ttcaccgccc tgttacacgc tctcagagag  1800
atcaaaacac tgtttctttt acggacacaa ggaaagatgg aattcacact ttacaacggt  1860
gagaagaaaa ccttctactc cagacccaac aaccacgaca actgctggct taacaccatt  1920
ctccagttgt tcaggtatgt tgatgagcct ttctttgact gggtctacga ctcgcctgaa  1980
aacctcactc ttgaggcaat caaacagttg gaagagacaa ccggtcttga gctgcacgag  2040
ggtggaccac ccgctctcgt catctggaac atcaaacact tgcttcacac cggaatcggc  2100
actgcctcac gccctagcga ggtgtgtatg gtggacggaa cggacatgtg tttagctgat  2160
tttcatgctg gcattttcct gaaaggacag gaacatgctg tgttcgcctg tgtcacctcc  2220
aacgggtggt acgcgattga tgacgaggac ttttaccctt ggacaccgga cccgtccgac  2280
gttctggtgt ttgtcccgta cgatcaagaa ccgcttaacg gagagtggaa aacaaaggtc  2340
cagaaaaggc tcaagggagc cgggcaatcc agcccggcaa ccgggtcaca gaaccaatca  2400
ggcaacactg ggagcatcat caacaattac tacatgcagc agtaccaaaa ctccatggac  2460
acacaacttg gtgacaacgc tacaagcgga ggctcaaacg aggggtccac ggacacaacc  2520
tccacccaca caaccaacac tcagaacaac gactggttct cgaagctggc cagttccgct  2580
ttcagcggtc ttttcggcgc tcttctcgcc gacaagaaaa ccgaggagac cactcttctc  2640
gaggaccgca tcctcactac tcgtaacgga cacaccacct cgacaaccca gtcgagcgtt  2700
```

-continued

```
ggagtcacgt acgggtatgc aacagctgag gatttcgtga gcgggccaaa cacctctggt  2760
ctcgagacca gggttgccca ggcagagcgg ttctttaaaa cccacctgtt cgactgggtc  2820
accagtgacc cattcggacg gtgccacctg ctggaacttc caactgacca caaaggtgtc  2880
tacggcagcc tgaccgactc gtatgcttat atgaggaacg gctgggatgt tgaagtcact  2940
gcagtgggaa accagttcaa tggaggatgc ctgttggtgg ccatggtgcc agaactttgc  3000
tccatacaga agagggagct gtaccagctc acgctctttc ctcaccagtt catcaaccct  3060
cggacgaaca tgacagcaca catcactgtg ccctttgttg gcgtcaaccg ttatgaccag  3120
tacaaggtac acaaaccttg gaccctcgtg gttatggttg tagccccct gactgtcaac  3180
agtgaaggtg ccccgcaaat caaggtgtat gccaacatcg cacctaccaa cgtacacgtc  3240
gcgggtgagt tcccttccaa agaggggatc ttccctgtgg cttgcagcga tggttatggc  3300
ggtctggtga ccactgaccc gaaaacggct gaccccgctt acgggaaagt gtttaacccc  3360
ccccgcaaca tgttgccggg gcggttcacc aattttcttg acgtggctga ggcgtgcccc  3420
acgtttctcc acttcgaggg tgacgtgcca tacgtgacca cgaagacgga ttcagacagg  3480
gtgctcgctc agttcgactt gtctttggca gcaaagcaca tgtcgaacac cttccttgca  3540
ggtctcgccc agtactacac acagtacagc ggcaccatca acctgcactt catgttcaca  3600
gggcctactg acgcgaaggc gcgttacatg attgcgtatg ctcctcctgg catggaacca  3660
cctaaaacgc cagaggcggc tgcccactgc attcatgctg aatgggacac agggttgaac  3720
tcaaaattca cattttcaat cccttacctt tcggcggctg attacgctta cacagcgtct  3780
gacactgctg agaccacaaa tgtacaggga tgggtttgcc tgtttcaaat aacacacggg  3840
aaagctgacg gcgacgcact ggtcgttttg gctagcgccg gaaaggactt tgagctgcgc  3900
ctgccggtgg atgctcgcac acagactacc tccgcgggcg agtcagctga ccccgtgacc  3960
gccaccgttg agaattacgg tggcgagaca caggtccaga ggcgccaaca cacggacgtc  4020
tcatttatat tagacagatt tgtgacagtg acaccaaaag accaaattaa tgtattggac  4080
ctgatgcaaa cccctgctca cactttggtg ggagcactcc ttcgtactgc cacttactat  4140
ttcgctgact tagaggtggc agtgaagcac aagggaaacc tcacctgggt cccgaacggg  4200
gcgcctgaag cggcgttgga caacaccacc aacccaacag cttaccacaa ggcaccactc  4260
acccgacttg cactgcctta cacggcgcca caccgcgtgt tggctactgt ttacaacggg  4320
aactgcaagt atggtgacgg cacggtggcc aatgtgagag gtgacctgca agtgttggcc  4380
cagaaggcgg cgagagcgct gcctacctcc ttcaactacg gtgccattaa agctactcgg  4440
gtgactgaac tgctttaccg catgaagagg gctgagacat actgccccg gcctcttttg  4500
gccattcacc cggaccaggc tagacacaag cagaagattg tggcaccggt ggaacagctt  4560
ctaaattttg acctgctcaa attggcggga gatgtggagt ccaaccctgg gcccttcttc  4620
ttctccgacg tcaggtcaaa tttctcaaaa ctggtagaaa ccatcaatca gatgcaggag  4680
gacatgtcaa caaaacacgg gcctgacttt aaccggttgg tgtccgcatt tgaggaattg  4740
gccactggag tgaaggctat cagggccggt ctcgacgagg ccaaaccctg gtacaaactc  4800
atcaagctcc tgagccgctt gtcgtgcatg gccgctgtag cagcacggtc aaaggaccca  4860
gtccttgtgg ccatcatgct ggctgacacc ggtcttgaga ttctggacag cacctttgtc  4920
gtgaagaaga tctccgactc gctctccagt ctctttcacg tgccggcccc cgtcttcagt  4980
ttcggagccc cgattctgtt ggccgggttg gtcaaagtcg cctcgagttt cttccggtcc  5040
acacccgaag accttgagag agcagaaaaa cagctcaaag cacgtgacat taacgacata  5100
ttcgccattc tcaagaacgg cgagtggctg gtcaagctga tccttgccat ccgcgactgg  5160
atcaaagcgt ggatcgcctc agaagaaaag tttgtcacca tgacggactt ggtgcctggt  5220
atccttgaaa agcagcggga tctcaacgac ccgagtaagt acaaggaagc caaggagtgg  5280
ctcgacaacg cgcgccaggc gtgtttgaag agcgggaacg ttcacattgc caatttgtgc  5340
aaagtggtcg ccccggcacc cagcaagtcg agacccgaac ccgtggtcgt ttgcctccgc  5400
ggcaaatccg gccaggggaa gagtttcctt gcgaacgtgc tcgcgcaagc aatctccacc  5460
cacttcaccg gcagaactga ttcggtttgg tactgcccgc ctgaccctga ccacttcgac  5520
ggttacaacc agcagaccgt tgtcgtgatg gacgatttgg gccagaaccc cgatggcaag  5580
gacttcaagt acttcgccca gatggtttcg accacggggt tcatcccgcc catggcctcg  5640
cttgaggaca aaggcaagcc tttcaacagc aaagtcatca ttgctaccac caacctgtac  5700
tcgggtttca ccccgagaac aatggtgtgt cctgacgcgc tgaaccggag gttccacttt  5760
gacatcgacg tgagtgccaa ggacgggtac aaagttaaca acaaattgga cataatcaaa  5820
gctcttgaag acacccacac caacccagtg gcgatgttcc aatacgactg tgcccttcta  5880
aacggtatgg cagttgaaat gaagagaatg caacaggata tgttcaagcc tcaaccaccc  5940
ctccagaacg tgtaccaact cgttcacgag gtgattgaac gggtcgagct ccacgagaag  6000
gtgtcgagcc acccgatttt caaacagata tcaattcctt cccaaaagtc tgtgttgtac  6060
ttcctcattg agaaaggcca acacgaagca gcaattgaat tctttgaggg aatggtgcat  6120
gactccatca aggaagagct ccggcccctc atccaacaga cctcatttgt gaaacgcgct  6180
tttaagcgcc tgaaggaaaa ctttgagact gttgccctgt gtttgactct tttggcaaac  6240
atagtgatca tgatccgcga gactcgcaag agacaacaga tggtggacga tgcagtgaat  6300
gactacattg agaaggcaaa catcaccaca gatgacaaga ctcttgacga ggcggaaaag  6360
aaccctctag agaccagcgg tgccagcact attggtttca gagagagaac tctcccgggg  6420
cacaaggcga gcgatgacgt gagctccgag cccgccaaac ccgtggagga ccgaccacaa  6480
gctgaagggc cctacgccgg accacttgag cgtcagaaac ctctgagagt gaaaaccaag  6540
ttgccacaac aggagggacc ctacgctggc ccgatggata gacagaaacc gttgaaagtg  6600
agagcaagag ccccggtcgt gaaggaggga ccctacgagg gaccggtgaa gaagcctgtc  6660
gctttgaaag tgaaagccaa gaacttgatt gtcactgaga gtggtgcccc accgaccgac  6720
ttgcagaaga tggtcatggg caacactaag cctgttgagc tcatcctcga cgggaagacg  6780
gtagccatct gctgtgctac cggagtgttt ggcactgcct acctcgtacc tcgtcacctc  6840
ttcgcggaga agtacgacaa gataatgttg gacggtagag ccatgacaga cagtgactac  6900
agagtgtttg agtttgagat taaagtaaaa ggacaggaca tgctctcaga cgctgcactc  6960
atggtgcttc accgtgggaa ccgcgtgaga gacatcacga aacattttcg tgacacagca  7020
agaatgaaga aaggcacccc cgttgtcggt gtgatcaaca acgccgacgt tgggagactg  7080
attttctctg gagaggccct tacctacaaa gacattgtag tgtgcatgga tggagacacc  7140
atgccgggcc tgtttgccta cagagccgcc accaaggctg gttactgcgg gggagccgtt  7200
ctcgccaagg acggagccga cacattcatc gttggcaccc actccgcagg tggtaacgga  7260
gttggatact gctcgtgcgt gtccaggtcc atgctcctga aaatgaaggc acacattgac  7320
cctgaaccac accacgaggg gttgattgtt gataccagag atgtggaaga gcgcgtgcat  7380
gtcatgcgta aaaccaagct tgcacccacc gtggcacacg gtgtgtttaa ccctgaattt  7440
```

```
ggtcccgctg ccttgtccaa caaggacccg cggctgaacg aaggggttgt cctcgatgaa  7500
gtcatcttct ccaaacacaa gggagacacg aaaatgtctg aggaggacaa agcgctgttc  7560
cgccgctgcg ctgccgacta cgcgtcgcac ttgcacagcg tgctggggac ggcaaatgcc  7620
ccattgagca tctatgaggc catcaaaggc gtcgacgggc tcgatgccat ggagccggac  7680
accgcgcccg gcctcccctg ggccctccag ggaaacgcc gtggtgcgtt gattgacttc  7740
gagaacggca cggtcggacc cgaagtcgag gctgccctaa agctcatgga gaaaagagag  7800
tacaaatttg cttgccagac cttcctgaaa gacgagattc gtccgatgga aaaagtacgt  7860
gctggcaaga ctcgcattgt cgacgttttg cccgtggaac acattcttta caccaggatg  7920
atgattggca gattctgtgc tcaaatgcac acaaacaatg gaccgcagat tggctcagcg  7980
gtcggttgca atcctgatgt tgattggcaa agatttggca cacattttgc tcagtacaga  8040
aacgtgtggg atgtggacta ttcggccttt gatgctaacc actgcagtga cgcaatgaac  8100
atcatgtttg aggaggtatt tcgcacagac ttcggtttcc acccaaatgc tgagtggatt  8160
ctgaagactc ttgtgaacac ggagcacgcc tatgagaaca aacgtatcac tgttgagggc  8220
gggatgccgt ctggctgttc cgcgacaagc atcatcaaca caattttgaa caacatttat  8280
gtgctctacg ctcttcgtag acactatgag ggagttgagc tggacaccta caccatgatc  8340
tcctacggag atgacatcgt ggttgcaagt gactacgatc tggattttga ggctctcaaa  8400
ccccacttca aatctcttgg tcaaaccatc actccagctg acaaaagcga caaaggtttt  8460
gttcttggtc actccattac cgatgtcact ttcctcaaaa gacacttcca catggactat  8520
ggaactgggt tttacaaacc tgtgatggcc tcaaagaccc tcgaggccat tctctccttt  8580
gcacgccgtg ggaccataca ggagaagttg atctccgtgg caggactcgc cgtccactca  8640
ggacctgacg agtaccggcg tctctttgag cccttccagg gtctcttcga gattccaagc  8700
tacagatcac tttacctgcg ttgggtgaac gccgtgtgcg gtgacgcata atccctcaga  8760
tgtcacaatt ggcagaaaga ctctgaggcg agcgacgccg taggagtgaa aagcccgaaa  8820
gggcttttcc cgcttcctat tccaaaaaaa aaaaaaaaaa actagttcta gagcggccgc  8880
caccgcggtg gagctccagc ttttgttccc tttagtgagg gttaattgcg cgcttggcgt  8940
aatcatggtc atagctgttt cctgtgtgaa attgttatcc gctcacaatt ccacacaaca  9000
tacgagccgg aagcataaag tgtaaagcct ggggtgccta atgagtgagc taactcacat  9060
taattgcgtt gcgctcactg cccgctttcc agtcgggaaa cctgtcgtgc cagctgcatt  9120
aatgaatcgg ccaacgcgcg gggagaggcg gtttgcgtat tgggcgctct tccgcttcct  9180
cgctcactga ctcgctgcgc tcggtcgttc ggctgcggcg agcggtatca gctcactcaa  9240
aggcggtaat acggttatcc acagaatcag gggataacgc aggaaagaac atgtgagcaa  9300
aaggccagca aaaggccagg aaccgtaaaa aggccgcgtt gctggcgttt ttccataggc  9360
tccgcccccc tgacgagcat cacaaaaatc gacgctcaag tcagaggtgg cgaaacccga  9420
caggactata aagataccag gcgtttcccc ctggaagctc cctcgtgcgc tctcctgttc  9480
cgaccctgcc gcttaccgga tacctgtccg cctttctccc ttcgggaagc gtggcgcttt  9540
ctcatagctc acgctgtagg tatctcagtt cggtgtaggt cgttcgctcc aagctgggct  9600
gtgtgcacga accccccgtt cagcccgacc gctgcgcctt atccggtaac tatcgtcttg  9660
agtccaaccc ggtaagacac gacttatcgc cactggcagc agccactggt aacaggatta  9720
gcagagcgag gtatgtaggc ggtgctacag agttcttgaa gtggtggcct aactacggct  9780
acactagaag gacagtattt ggtatctgcg ctctgctgaa gccagttacc ttcggaaaaa  9840
gagttggtag ctcttgatcc ggcaaacaaa ccaccgctgg tagcggtggt ttttttgttt  9900
gcaagcagca gattacgcgc agaaaaaaag gatctcaaga agatcctttg atcttttcta  9960
cggggtctga cgctcagtgg aacgaaaact cacgttaagg gattttggtc atgagattat  10020
caaaaaggat cttcacctag atccttttaa attaaaaatg aagttttaaa tcaatctaaa  10080
gtatatatga gtaaacttgg tctgacagtt accaatgctt aatcagtgag gcacctatct  10140
cagcgatctg tctatttcgt tcatccatag ttgcctgact ccccgtcgtg tagataacta  10200
cgatacggga gggcttacca tctggcccca gtgctgcaat gataccgcga gacccacgct  10260
caccggctcc agatttatca gcaataaacc agccagccgg aagggccgag cgcagaagtg  10320
gtcctgcaac tttatccgcc tccatccagt ctattaattg ttgccgggaa gctagagtaa  10380
gtagttcgcc agttaatagt ttgcgcaacg ttgttgccat tgctacaggc atcgtggtgt  10440
cacgctcgtc gtttggtatg gcttcattca gctccggttc ccaacgatca aggcgagtta  10500
catgatcccc catgttgtgc aaaaaagcgg ttagctcctt cggtcctccg atcgttgtca  10560
gaagtaagtt ggccgcagtg ttatcactca tggttatggc agcactgcat aattctctta  10620
ctgtcatgcc atccgtaaga tgcttttctg tgactggtga gtactcaacc aagtcattct  10680
gagaatagtg tatgcggcga ccgagttgct cttgcccggc gtcaatacgg gataataccg  10740
cgccacatag cagaacttta aaagtgctca tcattggaaa acgttcttcg gggcgaaaac  10800
tctcaaggat cttaccgctg ttgagatcca gttcgatgta acccactcgt gcacccaact  10860
gatcttcagc atcttttact ttcaccagcg tttctgggtg agcaaaaaca ggaaggcaaa  10920
atgccgcaaa aaagggaata agggcgacac ggaaatgttg aatactcata ctcttccttt  10980
ttcaatatta ttgaagcatt tatcagggtt attgtctcat gagcggatac atatttgaat  11040
gtatttagaa aaataaacaa ataggggttc cgcgcacatt tccccgaaaa gtgccac     11097
```

```
SEQ ID NO: 2            moltype = DNA  length = 2202
FEATURE                 Location/Qualifiers
source                  1..2202
                        mol_type = genomic DNA
                        organism = Foot-and-mouth disease virus
SEQUENCE: 2
ggcgccgggc aatccagccc ggcgactggg tcacagaacc agtcaggcaa cactggaagc  60
atcatcaaca actactacat gcagcagtac cagaactcca tggacacaca acttggtgac  120
aacgctatca gcggaggctc caacgagggg tccacggaca ccacttccac ccacacaacc  180
aacactcaga acaacgactg gttttcaaag ctggccagtt ccgcttttag cggccttttc  240
ggcgctcttc tcgccgacaa gaaaaccgag gagaccactc ttctcgagga ccgcatcctc  300
actacccgca acggacatac aacctcgaca acccagtcga gcgttggagt cacttacggg  360
tacgcaacag ctgaggactt tgtgagcggg ccaaacacat ccggtcttga gaccagggtt  420
gtgcaagcag agcggttctt caaaacccac ttgttcgact gggtcactag cgacccgttc  480
ggacggtgcc acctgctgga acttccaact gaccacaaag gtgtctacgg cagcctgacc  540
gattcttatg cttacatgag aaacggttgg gatgttgagg tcactgcagt gggaaaccag  600
ttcaacggag gatgcctgtt ggtagccatg gtgccagaac tttgctctat tgacaaaaga  660
```

```
gagctgtacc agctcacgct ctttccccac caattcatca acccccggac gaacatgacg  720
gcgcacatca ccgtgccctt tgttggcgtc aatcgctacg accagtacaa ggtacacaag  780
ccttggaccc tcgtggtcat ggtcgtggcc ccgctgactg tcaacactga aggtgctcca  840
cagatcaagg tttatgccaa catcgcccct accaacgtgc acgtcgcggg tgagttccct  900
tccaaggaag ggatcttccc cgtggcatgt agcgacggtt atggcggtct tgtgaccact  960
gacccaaaga cggctgaccc cgcctacggg aaagttttca atcccctcg caacatgttg  1020
ccagggcggt tcaccaactt ccttgacgtg gctgaggcgt gccctacgtt tctgcacttt  1080
gagggtgacg tgccatacgt gaccacaaag acggattcgg acagggttct tgctcagttt  1140
gacttgtctt tggcagcgaa gcacatgtcg aacacctttc tggcaggtct cgcccagtac  1200
tacacacagt acagcggcac catcaacctg cacttcatgt tcacagggcc cactgacgcg  1260
aaagcgcgtt acatgattgc atacgccccc cctggcatgg aaccgcccag aacacctgag  1320
gcggccgctc actgcattca tgcggagtgg gacactgggt tgaattcaaa attcacattt  1380
tcaatccctt acctttcggc ggctgactac gcgtacaccg cgtctgacac tgctgagacc  1440
acaaatgtac agggatgggt ttgcctgttt cagatcacac acgggaaggc tgacggtgac  1500
gcacttgtcg ttctggctag cgccggtaag gacttcgagc tgcggttgcc agttgacgct  1560
cgcacgcaga ccacctccac aggtgagtca gctgaccccg tgactgccac tgttgagaac  1620
tacggtggcg agacgcaggt ccagagacgc cagcacacgg acgtctcgtt catactggac  1680
agatttgtga aagtgacacc aaaagaccaa attaatgtgt tggacctgat gcagaccccc  1740
gcccacactt tggtaggtgc gcttctccgc accgccacct actacttcgc agacctagag  1800
gtggcagtga aacacgaggg gaaccttacc tgggtcccga atggggcgcc cgagacagcg  1860
ttggataaca ccaccaatcc aacggcttac cacaaggcac ctctcacccg gcttgcgctg  1920
ccttacacgg caccacaccg tgtcttggct actgtttaca acgggaactg caagtatggc  1980
gagagctcca caaccaacgt gagaggtgac ctgcaagtgt tggcccagaa agcggcgaga  2040
gcgctgccta cctcctttaa ctacggtgcc attaaggcca ctcgggtgac tgaactgctt  2100
taccgcatga agagggctga aacatactgc cccggcctc ttttggctat tcacccgagc  2160
gaagcaagac acaaacaaaa gatagtggca cctgtgaaac ag                  2202

SEQ ID NO: 3            moltype = DNA  length = 11100
FEATURE                 Location/Qualifiers
source                  1..11100
                        mol_type = other DNA
                        organism = synthetic construct
SEQUENCE: 3
ctaaattgta agcgttaata ttttgttaaa attcgcgtta aatttttgtt aaatcagctc  60
atttttaac caataggccg aaatcggcaa aatcccttat aaatcaaaag aatagaccga  120
gatagggttg agtgttgttc cagtttggaa caagagtcca ctattaaaga acgtggactc  180
caacgtcaaa gggcgaaaaa ccgtctatca gggcgatggc ccactacgtg aaccatcacc  240
ctaatcaagt tttttggggt cgaggtgccg taaagcacta aatcggaacc ctaaagggag  300
cccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac  420
cacacccgcc gcgcttaatg cgccgctaca gggcgcgtcc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc atatgtaata cgactcacta tagggttgaa agggggcgct  660
agggtctcac ccctagcatg ccaacgacag ctcctacgtc gcactccaca ctaacgtttg  720
tgtgcgcgcg ggaaccgatg gacttttgtt cacccaccta cagttggact cacggcaccg  780
cgtggccatt ttagctgggt tgtgcggacg aacactgctt gcgcatctcg cgtgaccggt  840
tagtactctt accactatcc gcctacttgg tcgttagcgc tgtcctgggc actcttgttg  900
ggggctgttc aacgctctac ggtctcccct gcgtaacaga ctacggtgtt ggggccgctt  960
cgtgcgagcc gatcgcttgg tgtgcctcgg ctgtcgcccg aagcccgcct ttcacccccc  1020
cccccccccc cccccctaggt tttaccgtcg ttcccgacgt taatggggaa acaaccacaa  1080
gcttaacacc gtcttgcccg acgtaaaagg gctgcaacca aaaagcttgt gccgcctttc  1140
ccggcgttaa tgggaggtaa ccacaagaca aaccttcacc cggaagtaaa acggcaactt  1200
cacacagttt tgcccgtttt cgtgagaaat gggccgtcaa cgcacgaaac gcgccgtcgc  1260
ttgaggagga cttgtacaaa cacgatctat gcaggtttcc acaactgaca caaaccgtgc  1320
aacttgaaac cccgcctggt ctttccaggt ctagaggggc gacattttgt actgtgcttg  1380
actccacgct cggtccacta gcgagtgtta gtagtagcac tgttgcttcg tagcggagca  1440
tgatggccgt gggagcttcc ccttggtaac aaggacccac ggggccaaaa gccacgtcct  1500
accggaccca tcatgtgtgc aaacccagca cggcaacttt actgcgaaaa ccactttaag  1560
gtgacactga tactggtact caatcactgg tgacaggcta aggatgccct tcaggtaccc  1620
cgaggtaaca cgcgacactc gggatctgag aaggggactg gggcttcttt aaaagtgccc  1680
agtttaaaaa gcttctatgc ctgaataggc gaccggaggc cggcgccttt tcactgtttt  1740
actactgttt tcatgaatac aactgactgt ttcaccgccc tgttacacgc tctcagagag  1800
atcaaaacac tgtttctttt acggacacaa ggaaagatgg aattcacact ttacaacggt  1860
gagaagaaaa ccttctactc cagacccaac aaccacgaca actgctggct taacaccatt  1920
ctccagttgt tcaggtatgt tgatgagcct ttctttgact gggtctacga ctcgcctgaa  1980
aacctcactc ttgaggcaat caaacagttg gaagagacaa ccggtcttga gctgcacgag  2040
ggtggaccac ccgctctcgt catctggaac atcaaacact tgcttcacac cggaatcggc  2100
actgcctcac gccctagcga ggtgtgtatg gtggacggaa cggacatgtg tttagctgat  2160
tttcatgctg gcattttcct gaaaggacag gaacatgctg tgttcgcctg tgtcacctcc  2220
aacgggtggt acgcgattga tgacgaggac ttttaccctt ggacaccgga cccgtccgac  2280
gttctggtgt ttgtcccgta cgatcaagaa ccgcttaacg gagagtggaa aacaaaggtc  2340
cagaaaaggc tcaagggcgc cgggcaatcc agcccggcga ctgggtcaca gaaccagtca  2400
ggcaacactg gaagcatcat caacaactac tacatgcagc agtaccagaa ctccatggac  2460
acacaacttg gtgacaacgc tatcagcgga ggctccaacg aggggtccac ggacaccact  2520
tccacccaca caaccaacac tcagaacaac gactggtttt caaagctggc cagttccgct  2580
tttagcggcc ttttcggcgc tcttctcgcc gacaagaaaa ccgaggagac cactcttctc  2640
gaggaccgca tcctcactac ccgcaacgga catacaacct cgacaaccca gtcgagcgtt  2700
ggagtcactt acgggtacgc aacagctgag gactttgtga gcgggccaaa cacatccggt  2760
```

-continued

```
cttgagacca gggttgtgca agcagagcgg ttcttcaaaa cccacttgtt cgactgggtc  2820
actagcgacc cgttcggacg gtgccacctg ctggaacttc caactgacca caaaggtgtc  2880
tacggcagcc tgaccgattc ttatgcttac atgagaaacg gttgggatgt tgaggtcact  2940
gcagtgggaa accagttcaa cggaggatgc ctgttggtag ccatggtgcc agaactttgc  3000
tctattgaca aaagagagct gtaccagctc acgctctttc cccaccaatt catcaacccc  3060
cggacgaaca tgacggcgca catcaccgtg ccctttgttg gcgtcaatcg ctacgaccag  3120
tacaaggtac acaagccttg gaccctcgtg gtcatggtcg tggccccgct gactgtcaac  3180
actgaaggtg ctccacagat caaggtttat gccaacatcg cccctaccaa cgtgcacgtc  3240
gcgggtgagt tcccttccaa ggaagggatc ttccccgtgg catgtagcga cggttatggc  3300
ggtcttgtga ccactgaccc aaagacggct gaccccgcct acgggaaagt tttcaatccc  3360
cctcgcaaca tgttgccagg gcggttcacc aacttccttg acgtggctga ggcgtgccct  3420
acgtttctgc actttgaggg tgacgtgcca tacgtgacca caaagacgga ttcggacagg  3480
gttcttgctc agtttgactt gtctttggca gcgaagcaca tgtcgaacac ctttctggca  3540
ggtctcgccc agtactacac acagtacagc ggcaccatca acctgcactt catgttcaca  3600
gggcccactg acgcgaaagc gcgttacatg attgcatacg ccccccctgg catggaaccg  3660
cccagaacac ctgaggcggc cgctcactgc attcatgcgg agtgggacac tgggttgaat  3720
tcaaaattca cattttcaat cccttacctt tcggcggctg actacgcgta caccgcgtct  3780
gacactgctg agaccacaaa tgtacaggga tgggtttgcc tgtttcagat cacacacggg  3840
aaggctgacg gtgacgcact tgtcgttctg gctagcgccg gtaaggactt cgagctgcgg  3900
ttgccagttg acgctcgcac gcagaccacc tccacaggtg agtcagctga ccccgtgact  3960
gccactgttg agaactacgg tggcgagacg caggtccaga gacgccagca cacggacgtc  4020
tcgttcatac tggacagatt tgtgaaagtg acaccaaaag accaaattaa tgtgttggac  4080
ctgatgcaga cccccgccca cactttggta ggtgcgcttc tccgcaccgc cacctactac  4140
ttcgcagacc tagaggtggc agtgaaacac gaggggaacc ttacctgggt cccgaatggg  4200
gcgcccgaga cagcgttgga taacaccacc aatccaacgg cttaccacaa ggcacctctc  4260
acccggcttg cgctgcctta cacggcacca caccgtgtct tggctactgt ttacaacggg  4320
aactgcaagt atggcgagag ctccacaacc aacgtgagag gtgacctgca agtgttggcc  4380
cagaaagcgg cgagagcgct gcctacctcc tttaactacg gtgccattaa ggccactcgg  4440
gtgactgaac tgctttaccg catgaagagg gctgaaacat actgccccg gcctcttttg  4500
gctattcacc cgagcgaagc aagacacaaa caaaagatag tggcacctgt gaaacagctt  4560
ctaaattttg acctgctcaa attggcggga gatgtggagt ccaaccctgg gcccttcttc  4620
ttctccgacg tcaggtcaaa tttctcaaaa ctggtagaaa ccatcaatca gatgcaggag  4680
gacatgtcaa caaaacacgg gcctgacttt aaccggttgg tgtccgcatt tgaggaattg  4740
gccactggag tgaaggctat cagggccggt ctcgacgagg ccaaaccctg gtacaaactc  4800
atcaagctcc tgagccgctt gtcgtgcatg gccgctgtag cagcacggtc aaaggaccca  4860
gtccttgtgg ccatcatgct ggctgacacc ggtcttgaga ttctggacag cacctttgtc  4920
gtgaagaaga tctccgactc gctctccagt ctctttcacg tgccggcccc cgtcttcagt  4980
ttcggagccc cgattctgtt ggccgggttg gtcaaagtcg cctcgagttt cttccggtcc  5040
acacccgaag accttgagag agcagaaaaa cagctcaaag cacgtgacat taacgacata  5100
ttcgccattc tcaagaacgg cgagtggctg gtcaagctga tccttgccat ccgcgactgg  5160
atcaaagcgt ggatcgcctc agaagaaaag tttgtcacca tgacggactt ggtgcctggt  5220
atccttgaaa agcagcggga tctcaacgac ccgagtaagt acaaggaagc caaggagtgg  5280
ctcgacaacg cgcgccaggc gtgtttgaag agcgggaacg ttcacattgc caatttgtgc  5340
aaagtggtcg ccccggcacc cagcaagtcg agacccgaac ccgtggtcgt ttgcctccgc  5400
ggcaaatccg gccaggggaa gagtttcctt gcgaacgtgc tcgcgcaagc aatctccacc  5460
cacttcaccg gcagaactga ttcggtttgg tactgcccgc ctgaccctga ccacttcgac  5520
ggttacaacc agcagaccgt tgtcgtgatg gacgatttgg gccagaaccc cgatggcaag  5580
gacttcaagt acttcgccca gatggtttcg accacggggt tcatcccgcc catggcctcg  5640
cttgaggaca aaggcaagcc tttcaacagc aaagtcatca ttgctaccac caacctgtac  5700
tcgggtttca ccccgagaac aatggtgtgt cctgacgcgc tgaaccggag gttccacttt  5760
gacatcgacg tgagtgccaa ggacgggtac aaagttaaca acaaattgga cataatcaaa  5820
gctcttgaag acacccacac caacccagtg gcgatgttcc aatacgactg tgcccttcta  5880
aacggtatgg cagttgaaat gaagagaatg caacaggata tgttcaagcc tcaaccaccc  5940
ctccagaacg tgtaccaact cgttcacgag gtgattgaac gggtcgagct ccacgagaag  6000
gtgtcgagcc accccgattt caaacagata tcaattcctt cccaaaagtc tgtgttgtac  6060
ttcctcattg agaaaggcca acacgaagca gcaattgaat tctttgaggg aatggtgcat  6120
gactccatca aggaagagct ccggcccctc atccaacaga cctcatttgt gaaacgcgct  6180
tttaagcgcc tgaaggaaaa ctttgagact gttgccctgt gtttgactct tttggcaaac  6240
atagtgatca tgatccgcga gactcgcaag agacaacaga tggtggacga tgcagtgaat  6300
gactacattg agaaggcaaa catcaccaca gatgacaaga ctcttgacga ggcggaaaag  6360
aaccctctag agaccagcgg tgccagcact attggtttca gagagagaac tctcccgggg  6420
cacaaggcga gcgatgacgt gagctccgag cccgccaaac ccgtggagga ccgaccacaa  6480
gctgaaggac cttacgaggg accggtgaag aagcctgtcg ctttgaaagt gaaagctaag  6540
aacttgattg tcactgaggg gccatatgaa ggaccagtga agaaacctgt cgctttgaaa  6600
gtgaaagcaa aagccccgat tgtcactgaa ggaccctacg agggaccggt gaagaagcct  6660
gtcgctttga aagtgaaagc caagaacttg attgtcactg agagtggtgc ccccaccgacc  6720
gacttgcaga agatggtcat gggcaacact aagcctgttg agctcatcct cgacgggaag  6780
acggtagcca tctgctgtgc taccggagtg tttggcactg cctacctcgt acctcgtcac  6840
ctcttcgcgg agaagtacga caagataatg ttggacggta gagccatgac agacagtgac  6900
tacagagtgt ttgagtttga gattaaagta aaaggacagg acatgctctc agacgctgca  6960
ctcatggtgc ttcaccgtgg gaaccgcgtg agagacatca cgaaacattt tcgtgacaca  7020
gcaagaatga agaaaggcac ccccgttgtc ggtgtgatca acaacgccga cgttgggaga  7080
ctgattttct ctggagaggc ccttacctac aaagacattg tagtgaccat ggatggagac  7140
accatgccgg gcctgtttgc ctacagagcc gccaccaagg ctggttactg cgggggagcc  7200
gttctcgcca aggacggagc cgacacattc atcgttggca cccactccgc aggtggtaac  7260
ggagttggat actgctcgtg cgtgtccagg tccatgctcc tgaaaatgaa ggcacacatt  7320
gaccctgaac cacaccacga ggggttgatt gttgatacca gagatgtgga agagcgcgtg  7380
catgtcatgc gtaaaaccaa gcttgcaccc accgtggcac acggtgtgtt taaccctgaa  7440
tttggtcccg ctgccttgtc caacaaggac ccgcggctga acgaaggggt tgtcctcgat  7500
```

```
gaagtcatct tctccaaaca caagggagac acgaaaatgt ctgaggagga caaagcgctg  7560
ttccgccgct gcgctgccga ctacgcgtcg cacttgcaca gcgtgctggg gacggcaaat  7620
gccccattga gcatctatga ggccatcaaa ggcgtcgacg ggctcgatgc catggagccg  7680
gacaccgcgc ccggcctccc ctgggccctc caggggaaac gccgtggtgc gttgattgac  7740
ttcgagaacg gcacggtcgg acccgaagtc gaggctgccc taaagctcat ggagaaaaga  7800
gagtacaaat ttgcttgcca gaccttcctg aaagacgaga ttcgtccgat ggaaaaagta  7860
cgtgctggca agactcgcat tgtcgacgtt ttgcccgtgg aacacattct ttacaccagg  7920
atgatgattg gcagattctg tgctcaaatg cacacaaaca atggaccgca gattggctca  7980
gcggtcggtt gcaatcctga tgttgattgg caaagatttg gcacacattt tgctcagtac  8040
agaaacgtgt gggatgtgga ctattcggcc tttgatgcta accactgcag tgacgcaatg  8100
aacatcatgt ttgaggaggt atttcgcaca gacttcggtt tccacccaaa tgctgagtgg  8160
attctgaaga ctcttgtgaa cacggagcac gcctatgaga acaaacgtat cactgttgag  8220
ggcgggatgc cgtctggctg ttccgcgaca agcatcatca acacaatttt gaacaacatt  8280
tatgtgctct acgctcttcg tagacactat gagggagttg agctggacac ctacaccatg  8340
atctcctacg gagatgacat cgtggttgca agtgactacg atctggattt tgaggctctc  8400
aaaccccact tcaaatctct tggtcaaacc atcactccag ctgacaaaag cgacaaaggt  8460
tttgttcttg gtcactccat taccgatgtc actttcctca aaagacactt ccacatggac  8520
tatggaactg ggttttacaa acctgtgatg gcctcaaaga ccctcgaggc cattctctcc  8580
tttgcacgcc gtgggaccat acaggagaag ttgatctccg tggcaggact cgccgtccac  8640
tcaggacctg acgagtaccg gcgtctcttt gagcccttcc agggtctctt cgagattcca  8700
agctacagat cactttacct gcgttgggtg aacgccgtgt gcggtgacgc ataatccctc  8760
agatgtcaca attggcagaa agactctgag gcgagcgacg ccgtaggagt gaaaagcccg  8820
aaagggcttt tcccgcttcc tattccaaaa aaaaaaaaaa aaaactagtt ctagagcggc  8880
cgccaccgcg gtggagctcc agcttttgtt ccctttagtg agggttaatt gcgcgcttgg  8940
cgtaatcatg gtcatagctg tttcctgtgt gaaattgtta tccgctcaca attccacaca  9000
acatacgagc cggaagcata aagtgtaaag cctggggtgc ctaatgagtg agctaactca  9060
cattaattgc gttgcgctca ctgcccgctt tccagtcggg aaacctgtcg tgccagctgc  9120
attaatgaat cggccaacgc gcggggagag gcggtttgcg tattgggcgc tcttccgctt  9180
cctcgctcac tgactcgctg cgctcggtcg ttcggctgcg gcgagcggta tcagctcact  9240
caaaggcggt aatacggtta tccacagaat caggggataa cgcaggaaag aacatgtgag  9300
caaaaggcca gcaaaaggcc aggaaccgta aaaaggccgc gttgctggcg tttttccata  9360
ggctccgccc ccctgacgag catcacaaaa atcgacgctc aagtcagagg tggcgaaacc  9420
cgacaggact ataaagatac caggcgtttc cccctggaag ctccctcgtg cgctctcctg  9480
ttccgaccct gccgcttacc ggatacctgt ccgcctttct cccttcggga agcgtggcgc  9540
tttctcatag ctcacgctgt aggtatctca gttcggtgta ggtcgttcgc tccaagctgg  9600
gctgtgtgca cgaacccccc gttcagcccg accgctgcgc cttatccggt aactatcgtc  9660
ttgagtccaa cccggtaaga cacgacttat cgccactggc agcagccact ggtaacagga  9720
ttagcagagc gaggtatgta ggcggtgcta cagagttctt gaagtggtgg cctaactacg  9780
gctacactag aaggacagta tttggtatct gcgctctgct gaagccagtt accttcggaa  9840
aaagagttgg tagctcttga tccggcaaac aaaccaccgc tggtagcggt ggtttttttg  9900
tttgcaagca gcagattacg cgcagaaaaa aaggatctca agaagatcct ttgatctttt  9960
ctacggggtc tgacgctcag tggaacgaaa actcacgtta agggattttg gtcatgagat  10020
tatcaaaaag gatcttcacc tagatccttt taaattaaaa atgaagtttt aaatcaatct  10080
aaagtatata tgagtaaact tggtctgaca gttaccaatg cttaatcagt gaggcaccta  10140
tctcagcgat ctgtctattt cgttcatcca tagttgcctg actccccgtc gtgtagataa  10200
ctacgatacg ggagggctta ccatctggcc ccagtgctgc aatgataccg cgagacccac  10260
gctcaccggc tccagattta tcagcaataa accagccagc cggaagggcc gagcgcagaa  10320
gtggtcctgc aactttatcc gcctccatcc agtctattaa ttgttgccgg gaagctagag  10380
taagtagttc gccagttaat agtttgcgca acgttgttgc cattgctaca ggcatcgtgg  10440
tgtcacgctc gtcgtttggt atggcttcat tcagctccgg ttcccaacga tcaaggcgag  10500
ttacatgatc ccccatgttg tgcaaaaaag cggttagctc cttcggtcct ccgatcgttg  10560
tcagaagtaa gttggccgca gtgttatcac tcatggttat ggcagcactg cataattctc  10620
ttactgtcat gccatccgta agatgctttt ctgtgactgg tgagtactca accaagtcat  10680
tctgagaata gtgtatgcgg cgaccgagtt gctcttgccc ggcgtcaata cgggataata  10740
ccgcgccaca tagcagaact ttaaaagtgc tcatcattgg aaaacgttct tcggggcgaa  10800
aactctcaag gatcttaccg ctgttgagat ccagttcgat gtaacccact cgtgcaccca  10860
actgatcttc agcatctttt actttcacca gcgtttctgg gtgagcaaaa acaggaaggc  10920
aaaatgccgc aaaaaaggga ataagggcga cacggaaatg ttgaatactc atactcttcc  10980
tttttcaata ttattgaagc atttatcagg gttattgtct catgagcgga tacatatttg  11040
aatgtattta gaaaaataaa caaatagggg ttccgcgcac atttccccga aaagtgccac  11100

SEQ ID NO: 4           moltype = DNA  length = 39
FEATURE                Location/Qualifiers
source                 1..39
                       mol_type = genomic DNA
                       organism = unidentified
SEQUENCE: 4
ggtaagcagc tctacaacgt ggaggccaca tcctatgcc                        39

SEQ ID NO: 5           moltype = AA  length = 13
FEATURE                Location/Qualifiers
source                 1..13
                       mol_type = protein
                       organism = unidentified
SEQUENCE: 5
GKQLYNVEAT SYA                                                    13

SEQ ID NO: 6           moltype = DNA  length = 39
FEATURE                Location/Qualifiers
```

```
source                  1..39
                        mol_type = other DNA
                        organism = synthetic construct
SEQUENCE: 6
ggaggccaca tcctatgccc gcgagaggcc ctaggtcgc                        39

SEQ ID NO: 7            moltype = DNA  length = 40
FEATURE                 Location/Qualifiers
source                  1..40
                        mol_type = other DNA
                        organism = synthetic construct
SEQUENCE: 7
acgttgtaga gctgcttacc gcgagggtcg ccgctcagct                       40

SEQ ID NO: 8            moltype = DNA  length = 11139
FEATURE                 Location/Qualifiers
source                  1..11139
                        mol_type = other DNA
                        organism = synthetic construct
SEQUENCE: 8
ctaaattgta agcgttaata ttttgttaaa attcgcgtta aatttttgtt aaatcagctc  60
atttttaac caataggccg aaatcggcaa aatcccttat aaatcaaaag aatagaccga  120
gatagggttg agtgttgttc cagtttggaa caagagtcca ctattaaaga acgtggactc  180
caacgtcaaa gggcgaaaaa ccgtctatca gggcgatggc ccactacgtg aaccatcacc  240
ctaatcaagt tttttggggt cgaggtgccg taaagcacta aatcggaacc ctaaagggag  300
cccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac  420
cacacccgcc gcgcttaatg cgccgctaca gggcgcgtcc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc atatgtaata cgactcacta tagggttgaa agggggcgct  660
agggtctcac ccctagcatg ccaacgacag ctcctacgtc gcactccaca ctaacgtttg  720
tgtgcgcgcg ggaaccgatg gacttttgtt cacccaccta cagttggact cacggcaccg  780
cgtggccatt ttagctgggt tgtgcggacg aacactgctt gcgcatctcg cgtgaccggt  840
tagtactctt accactatcc gcctacttgg tcgttagcgc tgtcctgggc actcttgttg  900
ggggctgttc aacgctctac ggtctcccct gcgtaacaga ctacggtgtt ggggccgctt  960
cgtgcgagcc gatcgcttgg tgtgcctcgg ctgtcgcccg aagcccgcct ttcacccccc  1020
cccccccccc cccccctaggt tttaccgtcg ttcccgacgt taatggggaa acaaccacaa  1080
gcttaacacc gtcttgcccg acgtaaaagg gctgcaacca aaaagcttgt gccgcctttc  1140
ccggcgttaa tgggaggtaa ccacaagaca aaccttcacc cggaagtaaa acggcaactt  1200
cacacagttt tgcccgtttt cgtgagaaat gggccgtcaa cgcacgaaac gcgccgtcgc  1260
ttgaggagga cttgtacaaa cacgatctat gcaggtttcc acaactgaca caaaccgtgc  1320
aacttgaaac ccgcctggt ctttccaggt ctagaggggc gacattttgt actgtgcttg  1380
actccacgct cggtccacta gcgagtgtta gtagtagcac tgttgcttcg tagcggagca  1440
tgatggccgt gggagcttcc ccttggtaac aaggacccac ggggccaaaa gccacgtcct  1500
accggaccca tcatgtgtgc aaacccagca cggcaacttt actgcgaaaa ccactttaag  1560
gtgacactga tactggtact caatcactgg tgacaggcta aggatgccct tcaggtaccc  1620
cgaggtaaca cgcgacactc gggatctgag aaggggactg gggcttcttt aaaagtgccc  1680
agtttaaaaa gcttctatgc ctgaataggc gaccggaggc cggcgccttt tcactgtttt  1740
actactgttt tcatgaatac aactgactgt ttcaccgccc tgttacacgc tctcagagag  1800
atcaaaacac tgtttctttt acggacacaa ggaaagatgg aattcacact ttacaacggt  1860
gagaagaaaa ccttctactc cagacccaac aaccacgaca actgctggct taacaccatt  1920
ctccagttgt tcaggtatgt tgatgagcct ttctttgact gggtctacga ctcgcctgaa  1980
aacctcactc ttgaggcaat caaacagttg gaagagacaa ccggtcttga gctgcacgag  2040
ggtggaccac ccgctctcgt catctggaac atcaaacact tgcttcacac cggaatcggc  2100
actgcctcac gccctagcga ggtgtgtatg gtggacggaa cggacatgtg tttagctgat  2160
tttcatgctg gcattttcct gaaaggacag gaacatgctg tgttcgcctg tgtcacctcc  2220
aacgggtggt acgcgattga tgacgaggac ttttaccctt ggacaccgga cccgtccgac  2280
gttctggtgt ttgtcccgta cgatcaagaa ccgcttaacg gagagtggaa aacaaaggtc  2340
cagaaaaggc tcaagggcgc cgggcaatcc agcccggcga ctgggtcaca gaaccagtca  2400
ggcaacactg gaagcatcat caacaactac tacatgcagc agtaccagaa ctccatggac  2460
acacaacttg gtgacaacgc tatcagcgga ggctccaacg aggggtccac ggacaccact  2520
tccacccaca caaccaacac tcagaacaac gactggtttt caaagctggc cagttccgct  2580
tttagcggcc ttttcggcgc tcttctcgcc gacaagaaaa ccgaggagac cactcttctc  2640
gaggaccgca tcctcactac ccgcaacgga catacaacct cgacaaccca gtcgagcgtt  2700
ggagtcactt acgggtacgc aacagctgag gactttgtga gcgggccaaa cacatccggt  2760
cttgagacca gggttgtgca agcagagcgg ttcttcaaaa cccacttgtt cgactgggtc  2820
actagcgacc cgttcggacg gtgccacctg ctggaacttc caactgacca caaaggtgtc  2880
tacggcagcc tgaccgattc ttatgcttac atgagaaacg gttgggatgt tgaggtcact  2940
gcagtgggaa accagttcaa cggaggatgc ctgttggtag ccatggtgcc agaactttgc  3000
tctattgaca aaagagagct gtaccagctc acgctctttc cccaccaatt catcaacccc  3060
cggacgaaca tgacggcgca catcaccgtg ccctttgttg gcgtcaatcg ctacgaccag  3120
tacaaggtac acaagccttg gaccctcgtg gtcatggtcg tggccccgct gactgtcaac  3180
actgaaggtg ctccacagat caaggtttat gccaacatcg cccctaccaa cgtgcacgtc  3240
gcgggtgagt tcccttccaa ggaagggatc ttccccgtgg catgtagcga cggttatggc  3300
ggtcttgtga ccactgaccc aaagacggct gaccccgcct acgggaaagt tttcaatccc  3360
cctcgcaaca tgttgccagg gcggttcacc aacttccttg acgtggctga ggcgtgccct  3420
acgtttctgc actttgaggg tgacgtgcca tacgtgacca caaagacgga ttcggacagg  3480
gttcttgctc agtttgactt gtctttggca gcgaagcaca tgtcgaacac ctttctggca  3540
```

```
ggtctcgccc agtactacac acagtacagc ggcaccatca acctgcactt catgttcaca  3600
gggcccactg acgcgaaagc gcgttacatg attgcatacg cccccctgg catggaaccg  3660
cccagaacac ctgaggcggc cgctcactgc attcatgcgg agtgggacac tgggttgaat  3720
tcaaaattca cattttcaat cccttacctt tcggcggctg actacgcgta caccgcgtct  3780
gacactgctg agaccacaaa tgtacaggga tgggtttgcc tgtttcagat cacacacggg  3840
aaggctgacg gtgacgcact tgtcgttctg gctagcgccg gtaaggactt cgagctgcgg  3900
ttgccagttg acgctcgcac gcagaccacc tccacaggtg agtcagctga ccccgtgact  3960
gccactgttg agaactacgg tggcgagacg caggtccaga gacgccagca cacggacgtc  4020
tcgttcatac tggacagatt tgtgaaagtg acaccaaaag accaaattaa tgtgttggac  4080
ctgatgcaga cccccgccca cactttggta ggtgcgcttc tccgcaccgc cacctactac  4140
ttcgcagacc tagaggtggc agtgaaacac gaggggaacc ttacctgggt cccgaatggg  4200
gcgcccgaga cagcgttgga taacaccacc aatccaacgg cttaccacaa ggcacctctc  4260
acccggcttg cgctgcctta cacggcacca caccgtgtct tggctactgt ttacaacggg  4320
aactgcaagt atggcgagag ctccacaacc aacgtgagag gtgacctgca agtgttggcc  4380
ggtaagcagc tctacaacgt ggaggccaca tcctatgccc agaaagcggc gagagcgctg  4440
cctacctcct ttaactacgg tgccattaag gccactcggg tgactgaact gctttaccgc  4500
atgaagaggg ctgaaacata ctgcccccgg cctcttttgg ctattcaccc gagcgaagca  4560
agacacaaac aaaagatagt ggcacctgtg aaacagcttc taaattttga cctgctcaaa  4620
ttggcgggag atgtggagtc caaccctggg cccttcttct tctccgacgt caggtcaaat  4680
ttctcaaaac tggtagaaac catcaatcag atgcaggagg acatgtcaac aaaacacggg  4740
cctgacttta accggttggt gtccgcattt gaggaattgg ccactggagt gaaggctatc  4800
agggccggtc tcgacgaggc caaaccctgg tacaaactca tcaagctcct gagccgcttg  4860
tcgtgcatgg ccgctgtagc agcacggtca aaggacccag tccttgtggc catcatgctg  4920
gctgacaccg gtcttgagat tctggacagc acctttgtcg tgaagaagat ctccgactcg  4980
ctctccagtc tctttcacgt gccggccccc gtcttcagtt tcggagcccc gattctgttg  5040
gccgggttgg tcaaagtcgc ctcgagtttc ttccggtcca cacccgaaga ccttgagaga  5100
gcagaaaaac agctcaaagc acgtgacatt aacgacatat tcgccattct caagaacggc  5160
gagtggctgg tcaagctgat ccttgccatc cgcgactgga tcaaagcgtg gatcgcctca  5220
gaagaaaagt ttgtcaccat gacggacttg gtgcctggta tccttgaaaa gcagcgggat  5280
ctcaacgacc cgagtaagta caaggaagcc aaggagtggc tcgacaacgc gcgccaggcg  5340
tgtttgaaga gcgggaacgt tcacattgcc aatttgtgca aagtggtcgc cccggcaccc  5400
agcaagtcga gacccgaacc cgtggtcgtt tgcctccgcg gcaaatccgg ccaggggaag  5460
agtttccttg cgaacgtgct cgcgcaagca atctccaccc acttcaccgg cagaactgat  5520
tcggtttggt actgcccgcc tgaccctgac cacttcgacg gttacaacca gcagaccgtt  5580
gtcgtgatgg acgatttggg ccagaacccc gatggcaagg acttcaagta cttcgcccag  5640
atggtttcga ccacggggtt catcccgccc atggcctcgc ttgaggacaa aggcaagcct  5700
ttcaacagca aagtcatcat tgctaccacc aacctgtact cgggtttcac cccgagaaca  5760
atggtgtgtc ctgacgcgct gaaccggagg ttccactttg acatcgacgt gagtgccaag  5820
gacgggtaca aagttaacaa caaattggac ataatcaaag ctcttgaaga cacccacacc  5880
aacccagtgg cgatgttcca atacgactgt gcccttctaa acggtatggc agttgaaatg  5940
aagagaatgc aacaggatat gttcaagcct caaccacccc tccagaacgt gtaccaactc  6000
gttcacgagg tgattgaacg ggtcgagctc cacgagaagg tgtcgagcca cccgattttc  6060
aaacagatat caattccttc ccaaaagtct gtgttgtact tcctcattga gaaaggccaa  6120
cacgaagcag caattgaatt ctttgaggga atggtgcatg actccatcaa ggaagagctc  6180
cggcccctca tccaacagac ctcatttgtg aaacgcgctt ttaagcgcct gaaggaaaac  6240
tttgagactg ttgccctgtg tttgactctt ttggcaaaca tagtgatcat gatccgcgag  6300
actcgcaaga gacaacagat ggtggacgat gcagtgaatg actacattga gaaggcaaac  6360
atcaccacag atgacaagac tcttgacgag gcggaaaaga accctctaga gaccagcggt  6420
gccagcacta ttggtttcag agagagaact ctcccggggc acaaggcgag cgatgacgtg  6480
agctccgagc ccgccaaacc cgtggaggac cgaccacaag ctgaaggacc ttacgaggga  6540
ccggtgaaga agcctgtcgc tttgaaagtg aaagctaaga acttgattgt cactgagggg  6600
ccatatgaag gaccagtgaa gaaacctgtc gctttgaaag tgaaagcaaa agccccgatt  6660
gtcactgaag gaccctacga gggaccggtg aagaagcctg tcgctttgaa agtgaaagcc  6720
aagaacttga ttgtcactga gagtggtgcc ccaccgaccg acttgcagaa gatggtcatg  6780
ggcaacacta agcctgttga gctcatcctc gacgggaaga cggtagccat ctgctgtgct  6840
accggagtgt ttggcactgc ctacctcgta cctcgtcacc tcttcgcgga gaagtacgac  6900
aagataatgt tggacggtag agccatgaca gacagtgact acagagtgtt tgagtttgag  6960
attaaagtaa aaggacagga catgctctca gacgctgcac tcatggtgct tcaccgtggg  7020
aaccgcgtga gagacatcac gaaacatttt cgtgacacag caagaatgaa gaaaggcacc  7080
cccgttgtcg gtgtgatcaa caacgccgac gttgggagac tgattttctc tggagaggcc  7140
cttacctaca aagacattgt agtgaccatg gatggagaca ccatgccggg cctgtttgcc  7200
tacagagccg ccaccaaggc tggttactgc gggggagccg ttctcgccaa ggacggagcc  7260
gacacattca tcgttggcac ccactccgca ggtggtaacg gagttggata ctgctcgtgc  7320
gtgtccaggt ccatgctcct gaaaatgaag gcacacattg accctgaacc acaccacgag  7380
gggttgattg ttgataccag agatgtggaa gagcgcgtgc atgtcatgcg taaaaccaag  7440
cttgcaccca ccgtggcaca cggtgtgttt aaccctgaat ttggtcccgc tgccttgtcc  7500
aacaaggacc cgcggctgaa cgaaggggtt gtcctcgatg aagtcatctt ctccaaacac  7560
aagggagaca cgaaaatgtc tgaggaggac aaagcgctgt tccgccgctg cgctgccgac  7620
tacgcgtcgc acttgcacag cgtgctgggg acggcaaatg ccccattgag catctatgag  7680
gccatcaaag gcgtcgacgg gctcgatgcc atggagccgg acaccgcgcc cggcctcccc  7740
tgggccctcc aggggaaacg ccgtggtgcg ttgattgact tcgagaacgg cacggtcgga  7800
cccgaagtcg aggctgccct aaagctcatg gagaaaagag agtacaaatt tgcttgccag  7860
accttcctga aagacgagat tcgtccgatg gaaaaagtac gtgctggcaa gactcgcatt  7920
gtcgacgttt tgcccgtgga acacattctt tacaccagga tgatgattgg cagattctgt  7980
gctcaaatgc acacaaacaa tggaccgcag attggctcag cggtcggttg caatcctgat  8040
gttgattggc aaagatttgg cacacatttt gctcagtaca gaaacgtgtg ggatgtggac  8100
tattcggcct ttgatgctaa ccactgcagt gacgcaatga acatcatgtt tgaggaggta  8160
tttcgcacag acttcggttt ccacccaaat gctgagtgga ttctgaagac tcttgtgaac  8220
acggagcacg cctatgagaa caaacgtatc actgttgagg gcgggatgcc gtctggctgt  8280
```

```
tccgcgacaa gcatcatcaa cacaattttg aacaacattt atgtgctcta cgctcttcgt  8340
agacactatg agggagttga gctggacacc tacaccatga tctcctacgg agatgacatc  8400
gtggttgcaa gtgactacga tctggatttt gaggctctca aacccccactt caaatctctt  8460
ggtcaaacca tcactccagc tgacaaaagc gacaaaggtt ttgttcttgg tcactccatt  8520
accgatgtca ctttcctcaa aagacacttc cacatggact atggaactgg gttttacaaa  8580
cctgtgatgg cctcaaagac cctcgaggcc attctctcct ttgcacgccg tgggaccata  8640
caggagaagt tgatctccgt ggcaggactc gccgtccact caggacctga cgagtaccgg  8700
cgtctctttg agcccttcca gggtctcttc gagattccaa gctacagatc actttacctg  8760
cgttgggtga acgccgtgtg cggtgacgca taatccctca gatgtcacaa ttggcagaaa  8820
gactctgagg cgagcgacgc cgtaggagtg aaaagcccga aagggctttt cccgcttcct  8880
attccaaaaa aaaaaaaaaa aaactagttc tagagcggcc gccaccgcgg tggagctcca  8940
gcttttgttc cctttagtga gggttaattg cgcgcttggc gtaatcatgg tcatagctgt  9000
ttcctgtgtg aaattgttat ccgctcacaa ttccacacaa catacgagcc ggaagcataa  9060
agtgtaaagc ctggggtgcc taatgagtga gctaactcac attaattgcg ttgcgctcac  9120
tgcccgcttt ccagtcggga aacctgtcgt gccagctgca ttaatgaatc ggccaacgcg  9180
cggggagagg cggtttgcgt attgggcgct cttccgcttc ctcgctcact gactcgctgc  9240
gctcggtcgt tcggctgcgg cgagcggtat cagctcactc aaaggcggta atacggttat  9300
ccacagaatc aggggataac gcaggaaaga acatgtgagc aaaaggccag caaaaggcca  9360
ggaaccgtaa aaaggccgcg ttgctggcgt ttttccatag gctccgcccc cctgacgagc  9420
atcacaaaaa tcgacgctca agtcagaggt ggcgaaaccc gacaggacta taaagatacc  9480
aggcgtttcc ccctggaagc tccctcgtgc gctctcctgt tccgaccctg ccgcttaccg  9540
gatacctgtc cgcctttctc ccttcgggaa gcgtggcgct ttctcatagc tcacgctgta  9600
ggtatctcag ttcggtgtag gtcgttcgct ccaagctggg ctgtgtgcac gaaccccccg  9660
ttcagcccga ccgctgcgcc ttatccggta actatcgtct tgagtccaac ccggtaagac  9720
acgacttatc gccactggca gcagccactg gtaacaggat tagcagagcg aggtatgtag  9780
gcggtgctac agagttcttg aagtggtggc ctaactacgg ctacactaga aggacagtat  9840
ttggtatctg cgctctgctg aagccagtta ccttcggaaa aagagttggt agctcttgat  9900
ccggcaaaca aaccaccgct ggtagcggtg gtttttttgt ttgcaagcag cagattacgc  9960
gcagaaaaaa aggatctcaa gaagatcctt tgatcttttc tacggggtct gacgctcagt  10020
ggaacgaaaa ctcacgttaa gggattttgg tcatgagatt atcaaaaagg atcttcacct  10080
agatcctttt aaattaaaaa tgaagtttta aatcaatcta aagtatatat gagtaaactt  10140
ggtctgacag ttaccaatgc ttaatcagtg aggcacctat ctcagcgatc tgtctatttc  10200
gttcatccat agttgcctga ctccccgtcg tgtagataac tacgatacgg gagggcttac  10260
catctggccc cagtgctgca atgataccgc gagacccacg ctcaccggct ccagatttat  10320
cagcaataaa ccagccagcc ggaagggccg agcgcagaag tggtcctgca actttatccg  10380
cctccatcca gtctattaat tgttgccggg aagctagagt aagtagttcg ccagttaata  10440
gtttgcgcaa cgttgttgcc attgctacag gcatcgtggt gtcacgctcg tcgtttggta  10500
tggcttcatt cagctccggt tcccaacgat caaggcgagt tacatgatcc cccatgttgt  10560
gcaaaaaagc ggttagctcc ttcggtcctc cgatcgttgt cagaagtaag ttggccgcag  10620
tgttatcact catggttatg gcagcactgc ataattctct tactgtcatg ccatccgtaa  10680
gatgcttttc tgtgactggt gagtactcaa ccaagtcatt ctgagaatag tgtatgcggc  10740
gaccgagttg ctcttgcccg gcgtcaatac gggataatac cgcgccacat agcagaactt  10800
taaaagtgct catcattgga aaacgttctt cggggcgaaa actctcaagg atcttaccgc  10860
tgttgagatc cagttcgatg taacccactc gtgcacccaa ctgatcttca gcatctttta  10920
ctttcaccag cgtttctggg tgagcaaaaa caggaaggca aaatgccgca aaaaagggaa  10980
taagggcgac acggaaatgt tgaatactca tactcttcct ttttcaatat tattgaagca  11040
tttatcaggg ttattgtctc atgagcggat acatatttga atgtatttag aaaaataaac  11100
aaataggggt tccgcgcaca tttccccgaa aagtgccac                         11139

SEQ ID NO: 9            moltype = DNA  length = 2205
FEATURE                 Location/Qualifiers
source                  1..2205
                        mol_type = genomic DNA
                        organism = Foot-and-mouth disease virus
SEQUENCE: 9
ggagccgggc aatccagtcc ggcgactggg tcgcagaacc agtcaggcaa cactgggagt  60
attattaaca actactacat gcaacagtac cagaactcca tggacaccca attaggtgac  120
aacgctataa gcggaggctc caatgaggga tccacggaca caacttccac ccacacaacc  180
aacactcaga acaacgactg gttttcaaag cttgccagtt ctgctttcag cggtcttttc  240
ggcgcccttc tcgccgataa gaagaccgag gagaccactc tcctcgagga ccgcattctc  300
accacccgca acgggcacac cacctccaca acccaatcga gtgtgggagt cacgtacggg  360
tactccaccc aggaagatca tgtttccgga cctaacacat ctggtttgga gacgcgggtg  420
gtgcaggcag aaagattttt caagaagcac ctgtttgatt ggacaccgga caaagctttt  480
gggcacttag agaagttgga acttcccact gaccacaagg gagtctacgg acacttggtg  540
gactcatttg catacatgag aaatggctgg gacgtggagg tgtccgctgt tggcaaccag  600
tttaacggcg ggtgtctcct ggtggccatg gtccctgaat ggaaagagtt caccccgcgt  660
gagaagtacc agctcacttt gtttccacac cagttcatca gccccagaac caacatgact  720
gcccacatcg tagtcccgta ccttggtgtg aacaggtacg accagtataa gaagcacaaa  780
ccctggacgc tggttgtgat ggtggtctca ccgctcacca ccaacactgt tagtgcagga  840
caaatcaagg tttatgccaa cattgccccg actcacgttc acgtggccgg cgagctcccc  900
tcgaaagagg ggattgtacc ggtcgcttgt tcggacgggt acggtggctt ggtgacaaca  960
gacccaaaaa cagctgaccc tgtttatggt atggtgtaca accccccag gacaaactac  1020
cccgggcggt tcacaaacct gttggatgtg gctgaggcct gccccacctt tctctgtttc  1080
gacgaaggga aaccgtacgt tgtgacaaga acggacgagc agcgtcttct ggccaagttc  1140
gacgtctctc ttgctgcaaa gcacatgtca aacacctacc tttcagggat agcacagtac  1200
tacgcacagt actctggtac catcaacctg cacttcatgt ttaccggctc cacggattca  1260
aaagcccgct acatggtggc gtacgttcca cccggtgtgg agacaccgcc ggacacgcct  1320
gagaaagctg cacactgcat ccatgctgag tgggacacag ggttgaactc caagtttact  1380
ttctctatcc cgtacgtgtc tgccgcagat tacgcgtaca ctgcgtctga tgtggcagaa  1440
```

-continued

```
acaacaaacg tacagggatg ggtctgcata taccaaatta cacacgggaa agctgaacaa  1500
gacactctgg ttgtgtcggc tagcgccggc aaggactttg agttgcgcct cccgattgac  1560
ccccgctcac aaaccactac caccggggag tctgcagacc ctgtcaccac cactgttgaa  1620
aactacggcg gtgagacaca agtccaacga cgtcagcaca ccgacgttac tttcataatg  1680
gacagatttg taaagataca aaacttgaac cccacacatg tcattgacct catgcaaacc  1740
caccaacacg ggttggtagg tgccctgtta cgtgctgcta cgtactactt ctctgacctg  1800
gagattgtgg tacgccatga cggtaaccta acctgggtac ccaatggagc acccgaggca  1860
gctctgtcta acacgggcaa ccccaccgcc tacctcaagg caccatttac gaggctcgcg  1920
ctcccctaca ccgcgccaca ccgcgtgttg gcaacagtgt acaacgggac gagcaagtac  1980
tccgcaggtg gtacgggcag acggggcgac ctagggcctc tcgcggcgag ggtcgccgct  2040
cagcttcctg cttctttcaa ctttggtgca attcaagcca cgaccatcca cgagctcctc  2100
gtgcgcatga agcgtgccga actctactgc cccagaccac tgttggcagt ggaggtgtcg  2160
tctcaagaca gacacaaaca gaagatcatt gcacctgcaa aacaa                   2205

SEQ ID NO: 10          moltype = DNA  length = 11103
FEATURE                Location/Qualifiers
source                 1..11103
                       mol_type = other DNA
                       organism = synthetic construct
SEQUENCE: 10
ctaaattgta agcgttaata ttttgttaaa attcgcgtta aatttttgtt aaatcagctc  60
atttttaac caataggccg aaatcggcaa aatcccttat aaatcaaaag aatagaccga  120
gatagggttg agtgttgttc cagtttggaa caagagtcca ctattaaaga acgtggactc  180
caacgtcaaa gggcgaaaaa ccgtctatca gggcgatggc ccactacgtg aaccatcacc  240
ctaatcaagt tttttggggt cgaggtgccg taaagcacta aatcggaacc ctaaagggag  300
cccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac  420
cacacccgcc gcgcttaatg cgccgctaca gggcgcgtcc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc atatgtaata cgactcacta tagggttgaa agggggcgct  660
agggtctcac ccctagcatg ccaacgacag ctcctacgtc gcactccaca ctaacgtttg  720
tgtgcgcgcg ggaaccgatg gacttttgtt cacccaccta cagttggact cacggcaccg  780
cgtggccatt ttagctgggt tgtgcggacg aacactgctt gcgcatctcg cgtgaccggt  840
tagtactctt accactatcc gcctacttgg tcgttagcgc tgtcctgggc actcttgttg  900
ggggctgttc aacgctctac ggtctcccct gcgtaacaga ctacggtgtt ggggccgctt  960
cgtgcgagcc gatcgcttgg tgtgcctcgg ctgtcgcccg aagcccgcct ttcacccccc  1020
cccccccccc ccccctaggt tttaccgtcg ttcccgacgt taatggggaa acaaccacaa  1080
gcttaacacc gtcttgcccg acgtaaaagg gctgcaacca aaaagcttgt gccgcctttc  1140
ccggcgttaa tgggaggtaa ccacaagaca aaccttcacc cggaagtaaa acggcaactt  1200
cacacagttt tgcccgtttt cgtgagaaat gggccgtcaa cgcacgaaac gcgccgtcgc  1260
ttgaggagga cttgtacaaa cacgatctat gcaggtttcc acaactgaca caaaccgtgc  1320
aacttgaaac cccgcctggt ctttccaggt ctagaggggc gacattttgt actgtgcttg  1380
actccacgct cggtccacta gcgagtgtta gtagtagcac tgttgcttcg tagcggagca  1440
tgatggccgt gggagcttcc ccttggtaac aaggacccac ggggccaaaa gccacgtcct  1500
accggaccca tcatgtgtgc aaacccagca cggcaacttt actgcgaaaa ccactttaag  1560
gtgacactga tactggtact caatcactgg tgacaggcta aggatgccct tcaggtaccc  1620
cgaggtaaca cgcgacactc gggatctgag aaggggactg gggcttcttt aaaagtgccc  1680
agtttaaaaa gcttctatgc ctgaataggc gaccggaggc cggcgccttt tcactgtttt  1740
actactgttt tcatgaatac aactgactgt ttcaccgccc tgttacacgc tctcagagag  1800
atcaaaacac tgtttctttt acggacacaa ggaaagatgg aattcacact ttacaacggt  1860
gagaagaaaa ccttctactc cagacccaac aaccacgaca actgctggct taacaccatt  1920
ctccagttgt tcaggtatgt tgatgagcct ttctttgact gggtctacga ctcgcctgaa  1980
aacctcactc ttgaggcaat caaacagttg gaagagacaa ccggtcttga gctgcacgag  2040
ggtggaccac ccgctctcgt catctggaac atcaaacact tgcttcacac cggaatcggc  2100
actgcctcac gccctagcga ggtgtgtatg gtggacggaa cggacatgtg tttagctgat  2160
tttcatgctg gcattttcct gaaaggacag gaacatgctg tgttcgcctg tgtcacctcc  2220
aacgggtggt acgcgattga tgacgaggac ttttaccctt ggacaccgga cccgtccgac  2280
gttctggtgt ttgtcccgta cgatcaagaa ccgcttaacg gagagtggaa aacaaaggtc  2340
cagaaaaggc tcaagggagc cgggcaatcc agtccggcga ctgggtcgca gaaccagtca  2400
ggcaacactg ggagtattat taacaactac tacatgcaac agtaccagaa ctccatggac  2460
acccaattag gtgacaacgc tataagcgga ggctccaatg agggatccac ggacacaact  2520
tccacccaca caaccaacac tcagaacaac gactggtttt caaagcttgc cagttctgct  2580
ttcagcggtc ttttcggcgc ccttctcgcc gataagaaga ccgaggagac cactctcctc  2640
gaggaccgca ttctcaccac ccgcaacggg cacaccacct ccacaaccca atcgagtgtg  2700
ggagtcacgt acgggtactc cacccaggaa gatcatgttt ccggacctaa cacatctggt  2760
ttggagacgc gggtggtgca ggcagaaaga tttttcaaga agcacctgtt tgattggaca  2820
ccggacaaag cttttgggca cttagagaag ttggaacttc ccactgacca caagggagtc  2880
tacggacact tggtggactc atttgcatac atgagaaatg gctgggacgt ggaggtgtcc  2940
gctgttggca accagtttaa cggcgggtgt ctcctggtgg ccatggtccc tgaatggaaa  3000
gagttcaccc cgcgtgagaa gtaccagctc actttgtttc cacaccagtt catcagcccc  3060
agaaccaaca tgactgccca catcgtagtc ccgtaccttg gtgtgaacag gtacgaccag  3120
tataagaagc acaaaccctg gacgctggtt gtgatggtgg tctcaccgct caccaccaac  3180
actgttagtg caggacaaat caaggtttat gccaacattg ccccgactca cgttcacgtg  3240
gccggcgagc tcccctcgaa agaggggatt gtaccggtcg cttgttcgga cgggtacggt  3300
ggcttggtga caacagaccc aaaaacagct gaccctgttt atggtatggt gtacaacccc  3360
cccaggacaa actaccccgg gcggttcaca aacctgttgg atgtggctga ggcctgcccc  3420
acctttctct gtttcgacga agggaaaccg tacgttgtga caagaacgga cgagcagcgt  3480
cttctggcca agttcgacgt ctctcttgct gcaaagcaca tgtcaaacac ctacctttca  3540
```

-continued

```
gggatagcac agtactacgc acagtactct ggtaccatca acctgcactt catgtttacc  3600
ggctccacgg attcaaaagc ccgctacatg gtggcgtacg ttccacccgg tgtggagaca  3660
ccgccggaca cgcctgagaa agctgcacac tgcatccatg ctgagtggga cacagggttg  3720
aactccaagt ttactttctc tatcccgtac gtgtctgccg cagattacgc gtacactgcg  3780
tctgatgtgg cagaaacaac aaacgtacag ggatgggtct gcatatacca aattacacac  3840
gggaaagctg aacaagacac tctggttgtg tcggctagcg ccggcaagga ctttgagttg  3900
cgcctcccga ttgacccccg ctcacaaacc actaccaccg gggagtctgc agaccctgtc  3960
accaccactg ttgaaaacta cggcggtgag acacaagtcc aacgacgtca gcacaccgac  4020
gttactttca taatggacag atttgtaaag atacaaaact tgaaccccac acatgtcatt  4080
gacctcatgc aaacccacca acacgggttg gtaggtgccc tgttacgtgc tgctacgtac  4140
tacttctctg acctggagat tgtggtacgc catgacggta acctaacctg ggtacccaat  4200
ggagcacccg aggcagctct gtctaacacg ggcaacccca ccgcctacct caaggcacca  4260
tttacgaggc tcgcgctccc ctacaccgcg ccacaccgcg tgttggcaac agtgtacaac  4320
gggacgagca agtactccgc aggtggtacg ggcagacggg gcgacctagg gcctctcgcg  4380
gcgagggtcg ccgctcagct tcctgcttct ttcaacttgg gtgcaattca agccacgacc  4440
atccacgagc tcctcgtgcg catgaagcgt gccgaactct actgccccag accactgttg  4500
gcagtggagg tgtcgtctca agacagacac aaacagaaga tcattgcacc tgcaaaacaa  4560
cttctaaatt ttgacctgct caaattggcg ggagatgtgg agtccaaccc tgggcccttc  4620
ttcttctccg acgtcaggtc aaatttctca aaactggtag aaaccatcaa tcagatgcag  4680
gaggacatgt caacaaaaca cggggcctgac tttaaccggt tggtgtccgc atttgaggaa  4740
ttggccactg gagtgaaggc tatcagggcc ggtctcgacg aggccaaacc ctggtacaaa  4800
ctcatcaagc tcctgagccg cttgtcgtgc atggccgctg tagcagcacg gtcaaaggac  4860
ccagtccttg tggccatcat gctggctgac accggtcttg agattctgga cagcaccttt  4920
gtcgtgaaga agatctccga ctcgctctcc agtctctttc acgtgccggc ccccgtcttc  4980
agtttcggag ccccgattct gttggccggg ttggtcaaag tcgcctcgag tttcttccgg  5040
tccacacccg aagaccttga gagagcagaa aaacagctca aagcacgtga cattaacgac  5100
atattcgcca ttctcaagaa cggcgagtgg ctggtcaagc tgatccttgc catccgcgac  5160
tggatcaaag cgtggatcgc ctcagaagaa aagtttgtca ccatgacgga cttggtgcct  5220
ggtatccttg aaaagcagcg ggatctcaac gacccgagta agtacaagga agccaaggag  5280
tggctcgaca acgcgcgcca ggcgtgtttg aagagcggga acgttcacat tgccaatttg  5340
tgcaaagtgg tcgccccggc acccagcaag tcgagacccg aacccgtggt cgtttgcctc  5400
cgcggcaaat ccggccaggg gaagagtttc cttgcgaacg tgctcgcgca agcaatctcc  5460
acccacttca ccggcagaac tgattcggtt tggtactgcc cgcctgaccc tgaccacttc  5520
gacggttaca accagcagac cgttgtcgtg atggacgatt tgggccagaa ccccgatggc  5580
aaggacttca agtacttcgc ccagatggtt tcgaccacgg ggttcatccc gcccatggcc  5640
tcgcttgagg acaaaggcaa gcctttcaac agcaaagtca tcattgctac caccaacctg  5700
tactcgggtt tcaccccgag aacaatggtg tgtcctgacg cgctgaaccg gaggttccac  5760
tttgacatcg acgtgagtgc caaggacggg tacaaagtta acaacaaatt ggacataatc  5820
aaagctcttg aagacaccca caccaaccca gtggcgatgt tccaatacga ctgtgccctt  5880
ctaaacggta tggcagttga aatgaagaga atgcaacagg atatgttcaa gcctcaacca  5940
cccctccaga acgtgtacca actcgttcac gaggtgattg aacgggtcga gctccacgag  6000
aaggtgtcga gccacccgat tttcaaacag atatcaattc cttcccaaaa gtctgtgttg  6060
tacttcctca ttgagaaagg ccaacacgaa gcagcaattg aattctttga gggaatggtg  6120
catgactcca tcaaggaaga gctccggccc ctcatccaac agacctcatt tgtgaaacgc  6180
gcttttaagc gcctgaagga aaactttgag actgttgccc tgtgtttgac tcttttggca  6240
aacatagtga tcatgatccg cgagactcgc aagagacaac agatggtgga cgatgcagtg  6300
aatgactaca ttgagaaggc aaacatcacc acagatgaca agactcttga cgaggcggaa  6360
aagaaccctc tagagaccag cggtgccagc actattggtt tcagagagag aactctcccg  6420
gggcacaagg cgagcgatga cgtgagctcc gagcccgcca aacccgtgga ggaccgacca  6480
caagctgaag gaccttacga gggaccggtg aagaagcctg tcgctttgaa agtgaaagct  6540
aagaacttga ttgtcactga ggggccatat gaaggaccag tgaagaaacc tgtcgctttg  6600
aaagtgaaag caaaagcccc gattgtcact gaaggaccct acgagggacc ggtgaagaag  6660
cctgtcgctt tgaaagtgaa agccaagaac ttgattgtca ctgagagtgg tgccccaccg  6720
accgacttgc agaagatggt catgggcaac actaagcctg ttgagctcat cctcgacggg  6780
aagacggtag ccatctgctg tgctaccgga gtgtttggca ctgcctacct cgtacctcgt  6840
cacctcttcg cggagaagta cgacaagata atgttggacg gtagagccat gacagacagt  6900
gactacagag tgtttgagtt tgagattaaa gtaaaaggac aggacatgct ctcagacgct  6960
gcactcatgg tgcttcaccg tgggaaccgc gtgagagaca tcacgaaaca ttttcgtgac  7020
acagcaagaa tgaagaaagg cacccccgtt gtcggtgtga tcaacaacgc cgacgttggg  7080
agactgattt tctctggaga ggcccttacc tacaaagaca ttgtagtgac catggatgga  7140
gacaccatgc cgggcctgtt tgcctacaga gccgccacca aggctggtta ctgcggggga  7200
gccgttctcg ccaaggacgg agccgacaca ttcatcgttg gcacccactc cgcaggtggt  7260
aacggagttg gatactgctc gtgcgtgtcc aggtccatgc tcctgaaaat gaaggcacac  7320
attgaccctg aaccacacca cgaggggttg attgttgata ccagagatgt ggaagagcgc  7380
gtgcatgtca tgcgtaaaac caagcttgca cccaccgtgg cacacggtgt gtttaaccct  7440
gaatttggtc ccgctgcctt gtccaacaag gacccgcggc tgaacgaagg ggttgtcctc  7500
gatgaagtca tcttctccaa acacaaggga gacacgaaaa tgtctgagga ggacaaagcg  7560
ctgttccgcc gctgcgctgc cgactacgcg tcgcacttgc acagcgtgct ggggacggca  7620
aatgccccat tgagcatcta tgaggccatc aaaggcgtcg acgggctcga tgccatggag  7680
ccggacaccg cgcccggcct cccctgggcc ctccagggga aacgccgtgg tgcgttgatt  7740
gacttcgaga acggcacggt cggacccgaa gtcgaggctg ccctaaagct catggagaaa  7800
agagagtaca aatttgcttg ccagaccttc ctgaaagacg agattcgtcc gatggaaaaa  7860
gtacgtgctg gcaagactcg cattgtcgac gttttgcccg tggaacacat tctttacacc  7920
aggatgatga ttggcagatt ctgtgctcaa atgcacacaa acaatggacc gcagattggc  7980
tcagcggtcg gttgcaatcc tgatgttgat tggcaaagat ttggcacaca ttttgctcag  8040
tacagaaacg tgtgggatgt ggactattcg gcctttgatg ctaaccactg cagtgacgca  8100
atgaacatca tgtttgagga ggtatttcgc acagacttcg gtttccaccc aaatgctgag  8160
tggattctga agactcttgt gaacacggag cacgcctatg agaacaaacg tatcactgtt  8220
gagggcggga tgccgtctgg ctgttccgcg acaagcatca tcaacacaat tttgaacaac  8280
```

```
atttatgtgc tctacgctct tcgtagacac tatgagggag ttgagctgga cacctacacc  8340
atgatctcct acggagatga catcgtggtt gcaagtgact acgatctgga ttttgaggct  8400
ctcaaacccc acttcaaatc tcttggtcaa accatcactc cagctgacaa aagcgacaaa  8460
ggttttgttc ttggtcactc cattaccgat gtcactttcc tcaaaagaca cttccacatg  8520
gactatggaa ctgggtttta caaacctgtg atggcctcaa agaccctcga ggccattctc  8580
tcctttgcac gccgtgggac catacaggag aagttgatct ccgtggcagg actcgccgtc  8640
cactcaggac ctgacgagta ccggcgtctc tttgagccct tccagggtct cttcgagatt  8700
ccaagctaca gatcacttta cctgcgttgg gtgaacgccg tgtgcggtga cgcataatcc  8760
ctcagatgtc acaattggca gaaagactct gaggcgagcg acgccgtagg agtgaaaagc  8820
ccgaaagggc ttttcccgct tcctattcca aaaaaaaaaa aaaaaaacta gttctagagc  8880
ggccgccacc gcggtggagc tccagctttt gttcccttta gtgagggtta attgcgcgct  8940
tggcgtaatc atggtcatag ctgtttcctg tgtgaaattg ttatccgctc acaattccac  9000
acaacatacg agccggaagc ataaagtgta aagcctgggg tgcctaatga gtgagctaac  9060
tcacattaat tgcgttgcgc tcactgcccg ctttccagtc gggaaacctg tcgtgccagc  9120
tgcattaatg aatcggccaa cgcgcgggga gaggcggttt gcgtattggg cgctcttccg  9180
cttcctcgct cactgactcg ctgcgctcgg tcgttcggct gcggcgagcg gtatcagctc  9240
actcaaaggc ggtaatacgg ttatccacag aatcagggga taacgcagga aagaacatgt  9300
gagcaaaagg ccagcaaaag gccaggaacc gtaaaaaggc cgcgttgctg gcgtttttcc  9360
ataggctccg cccccctgac gagcatcaca aaaatcgacg ctcaagtcag aggtggcgaa  9420
acccgacagg actataaaga taccaggcgt ttccccctgg aagctccctc gtgcgctctc  9480
ctgttccgac cctgccgctt accggatacc tgtccgcctt tctcccttcg ggaagcgtgg  9540
cgctttctca tagctcacgc tgtaggtatc tcagttcggt gtaggtcgtt cgctccaagc  9600
tgggctgtgt gcacgaaccc cccgttcagc ccgaccgctg cgccttatcc ggtaactatc  9660
gtcttgagtc caacccggta agacacgact tatcgccact ggcagcagcc actggtaaca  9720
ggattagcag agcgaggtat gtaggcggtg ctacagagtt cttgaagtgg tggcctaact  9780
acggctacac tagaaggaca gtatttggta tctgcgctct gctgaagcca gttaccttcg  9840
gaaaaagagt tggtagctct tgatccggca aacaaaccac cgctggtagc ggtggttttt  9900
ttgtttgcaa gcagcagatt acgcgcagaa aaaaaggatc tcaagaagat cctttgatct  9960
tttctacggg gtctgacgct cagtggaacg aaaactcacg ttaagggatt ttggtcatga  10020
gattatcaaa aaggatcttc acctagatcc ttttaaatta aaaatgaagt tttaaatcaa  10080
tctaaagtat atatgagtaa acttggtctg acagttacca atgcttaatc agtgaggcac  10140
ctatctcagc gatctgtcta tttcgttcat ccatagttgc ctgactcccc gtcgtgtaga  10200
taactacgat acgggagggc ttaccatctg gccccagtgc tgcaatgata ccgcgagacc  10260
cacgctcacc ggctccagat ttatcagcaa taaaccagcc agccggaagg gccgagcgca  10320
gaagtggtcc tgcaacttta tccgcctcca tccagtctat taattgttgc cgggaagcta  10380
gagtaagtag ttcgccagtt aatagtttgc gcaacgttgt tgccattgct acaggcatcg  10440
tggtgtcacg ctcgtcgttt ggtatggctt cattcagctc cggttcccaa cgatcaaggc  10500
gagttacatg atcccccatg ttgtgcaaaa aagcggttag ctccttcggt cctccgatcg  10560
ttgtcagaag taagttggcc gcagtgttat cactcatggt tatggcagca ctgcataatt  10620
ctcttactgt catgccatcc gtaagatgct tttctgtgac tggtgagtac tcaaccaagt  10680
cattctgaga atagtgtatg cggcgaccga gttgctcttg cccggcgtca atacgggata  10740
ataccgcgcc acatagcaga actttaaaag tgctcatcat tggaaaacgt tcttcggggc  10800
gaaaactctc aaggatctta ccgctgttga gatccagttc gatgtaaccc actcgtgcac  10860
ccaactgatc ttcagcatct tttactttca ccagcgtttc tgggtgagca aaaacaggaa  10920
ggcaaaatgc cgcaaaaaag ggaataaggg cgacacggaa atgttgaata ctcatactct  10980
tcctttttca atattattga agcatttatc agggttattg tctcatgagc ggatacatat  11040
ttgaatgtat ttagaaaaat aaacaaatag gggttccgcg cacatttccc cgaaaagtgc  11100
cac                                                                11103
```

```
SEQ ID NO: 11          moltype = DNA  length = 11142
FEATURE                Location/Qualifiers
source                 1..11142
                       mol_type = other DNA
                       organism = synthetic construct
SEQUENCE: 11
ctaaattgta agcgttaata ttttgttaaa attcgcgtta aatttttgtt aaatcagctc  60
atttttttaac caataggccg aaatcggcaa aatcccttat aaatcaaaag aatagaccga  120
gatagggttg agtgttgttc cagtttggaa caagagtcca ctattaaaga acgtggactc  180
caacgtcaaa gggcgaaaaa ccgtctatca gggcgatggc ccactacgtg aaccatcacc  240
ctaatcaagt tttttggggt cgaggtgccg taaagcacta aatcggaacc ctaaagggag  300
cccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac  420
cacacccgcc gcgcttaatg cgccgctaca gggcgcgtcc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc atatgtaata cgactcacta tagggttgaa agggggcgct  660
agggtctcac ccctagcatg ccaacgacag ctcctacgtc gcactccaca ctaacgtttg  720
tgtgcgcgcg ggaaccgatg gacttttgtt cacccaccta cagttggact cacggcaccg  780
cgtggccatt ttagctgggt tgtgcggacg aacactgctt gcgcatctcg cgtgaccggt  840
tagtactctt accactatcc gcctacttgg tcgttagcgc tgtcctgggc actcttgttg  900
ggggctgttc aacgctctac ggtctcccct gcgtaacaga ctacggtgtt ggggccgctt  960
cgtgcgagcc gatcgcttgg tgtgcctcgg ctgtcgcccg aagcccgcct ttcacccccc  1020
cccccccccc cccccctaggt tttaccgtcg ttcccgacgt taatggggaa acaaccacaa  1080
gcttaacacc gtcttgcccg acgtaaaagg gctgcaacca aaaagcttgt gccgcctttc  1140
ccggcgttaa tgggaggtaa ccacaagaca aaccttcacc cggaagtaaa acggcaactt  1200
cacacagttt tgcccgtttt cgtgagaaat gggccgtcaa cgcacgaaac gcgccgtcgc  1260
ttgaggagga cttgtacaaa cacgatctat gcaggtttcc acaactgaca caaaccgtgc  1320
aacttgaaac cccgcctggt ctttccaggt ctagaggggc gacattttgt actgtgcttg  1380
actccacgct cggtccacta gcgagtgtta gtagtagcac tgttgcttcg tagcggagca  1440
```

-continued

```
tgatggccgt gggagcttcc ccttggtaac aaggacccac ggggccaaaa gccacgtcct  1500
accggaccca tcatgtgtgc aaacccagca cggcaacttt actgcgaaaa ccactttaag  1560
gtgacactga tactggtact caatcactgg tgacaggcta aggatgccct tcaggtaccc  1620
cgaggtaaca cgcgacactc gggatctgag aaggggactg gggcttcttt aaaagtgccc  1680
agtttaaaaa gcttctatgc ctgaataggc gaccggaggc cggcgccttt tcactgtttt  1740
actactgttt tcatgaatac aactgactgt ttcaccgccc tgttacacgc tctcagagag  1800
atcaaaacac tgtttctttt acggacacaa ggaaagatgg aattcacact ttacaacggt  1860
gagaagaaaa ccttctactc cagacccaac aaccacgaca actgctggct taacaccatt  1920
ctccagttgt tcaggtatgt tgatgagcct ttctttgact gggtctacga ctcgcctgaa  1980
aacctcactc ttgaggcaat caaacagttg gaagagacaa ccggtcttga gctgcacgag  2040
ggtggaccac ccgctctcgt catctggaac atcaaacact tgcttcacac cggaatcggc  2100
actgcctcac gccctagcga ggtgtgtatg gtggacggaa cggacatgtg tttagctgat  2160
tttcatgctg gcattttcct gaaaggacag gaacatgctg tgttcgcctg tgtcacctcc  2220
aacgggtggt acgcgattga tgacgaggac ttttaccctt ggacaccgga cccgtccgac  2280
gttctggtgt ttgtcccgta cgatcaagaa ccgcttaacg gagagtggaa aacaaaggtc  2340
cagaaaaggc tcaagggagc cgggcaatcc agtccggcga ctgggtcgca gaaccagtca  2400
ggcaacactg ggagtattat taacaactac tacatgcaac agtaccagaa ctccatggac  2460
acccaattag gtgacaacgc tataagcgga ggctccaatg agggatccac ggacacaact  2520
tccacccaca caaccaacac tcagaacaac gactggtttt caaagcttgc cagttctgct  2580
ttcagcggtc ttttcggcgc ccttctcgcc gataagaaga ccgaggagac cactctcctc  2640
gaggaccgca ttctcaccac ccgcaacggg cacaccacct ccacaaccca atcgagtgtg  2700
ggagtcacgt acgggtactc cacccaggaa gatcatgttt ccggacctaa cacatctggt  2760
ttggagacgc gggtggtgca ggcagaaaga tttttcaaga agcacctgtt tgattggaca  2820
ccggacaaag cttttgggca cttagagaag ttggaacttc ccactgacca caagggagtc  2880
tacggacact tggtggactc atttgcatac atgagaaatg gctgggacgt ggaggtgtcc  2940
gctgttggca accagtttaa cggcgggtgt ctcctggtgg ccatggtccc tgaatggaaa  3000
gagttcaccc cgcgtgagaa gtaccagctc actttgtttc cacaccagtt catcagcccc  3060
agaaccaaca tgactgccca catcgtagtc ccgtaccttg gtgtgaacag gtacgaccag  3120
tataagaagc acaaaccctg gacgctggtt gtgatggtgg tctcaccgct caccaccaac  3180
actgttagtg caggacaaat caaggtttat gccaacattg ccccgactca cgttcacgtg  3240
gccggcgagc tcccctcgaa agaggggatt gtaccggtcg cttgttcgga cgggtacggt  3300
ggcttggtga caacagaccc aaaaacagct gaccctgttt atggtatggt gtacaacccc  3360
cccaggacaa actaccccgg gcggttcaca aacctgttgg atgtggctga ggcctgcccc  3420
acctttctct gtttcgacga agggaaaccg tacgttgtga caagaacgga cgagcagcgt  3480
cttctggcca agttcgacgt ctctcttgct gcaaagcaca tgtcaaacac ctacctttca  3540
gggatagcac agtactacgc acagtactct ggtaccatca acctgcactt catgtttacc  3600
ggctccacgg attcaaaagc ccgctacatg gtggcgtacg ttccacccgg tgtggagaca  3660
ccgccggaca cgcctgagaa agctgcacac tgcatccatg ctgagtggga cacagggttg  3720
aactccaagt ttactttctc tatcccgtac gtgtctgccg cagattacgc gtacactgcg  3780
tctgatgtgg cagaaacaac aaacgtacag ggatgggtct gcatatacca aattacacac  3840
gggaaagctg aacaagacac tctggttgtg tcggctagcg ccggcaagga ctttgagttg  3900
cgcctcccga ttgacccccg ctcacaaacc actaccaccg ggagtctgc agaccctgtc  3960
accaccactg ttgaaaacta cggcggtgag acacaagtcc aacgacgtca gcacaccgac  4020
gttactttca taatggacag atttgtaaag atacaaaact tgaaccccac acatgtcatt  4080
gacctcatgc aaacccacca acacgggttg gtaggtgccc tgttacgtgc tgctacgtac  4140
tacttctctg acctggagat tgtggtacgc catgacggta acctaacctg ggtacccaat  4200
ggagcacccg aggcagctct gtctaacacg ggcaacccca ccgcctacct caaggcacca  4260
tttacgaggc tcgcgctccc ctacaccgcg ccacaccgcg tgttggcaac agtgtacaac  4320
gggacgagca agtactccgc aggtggtacg ggcagacggg gcgacctagg gcctctcgcg  4380
ggtaagcagc tctacaacgt ggaggccaca tcctatgccg cgagggtcgc cgctcagctt  4440
cctgcttctt tcaactttgg tgcaattcaa gccacgacca tccacgagct cctcgtgcgc  4500
atgaagcgtg ccgaactcta ctgccccaga ccactgttgg cagtggaggt gtcgtctcaa  4560
gacagacaca aacagaagat cattgcacct gcaaaacaac ttctaaattt tgacctgctc  4620
aaattggcgg gagatgtgga gtccaaccct gggcccttct tcttctccga cgtcaggtca  4680
aatttctcaa aactggtaga aaccatcaat cagatgcagg aggacatgtc aacaaaacac  4740
gggcctgact ttaaccggtt ggtgtccgca tttgaggaat tggccactgg agtgaaggct  4800
atcagggccg gtctcgacga ggccaaaccc tggtacaaac tcatcaagct cctgagccgc  4860
ttgtcgtgca tggccgctgt agcagcacgg tcaaaggacc cagtccttgt ggccatcatg  4920
ctggctgaca ccggtcttga gattctggac agcacctttg tcgtgaagaa gatctccgac  4980
tcgctctcca gtctctttca cgtgccggcc cccgtcttca gtttcggagc cccgattctg  5040
ttggccgggt tggtcaaagt cgcctcgagt ttcttccggt ccacacccga agaccttgag  5100
agagcagaaa aacagctcaa agcacgtgac attaacgaca tattcgccat tctcaagaac  5160
ggcgagtggc tggtcaagct gatccttgcc atccgcgact ggatcaaagc gtggatcgcc  5220
tcagaagaaa agtttgtcac catgacggac ttggtgcctg gtatccttga aaagcagcgg  5280
gatctcaacg acccgagtaa gtacaaggaa gccaaggagt ggctcgacaa cgcgcgccag  5340
gcgtgtttga agagcgggaa cgttcacatt gccaatttgt gcaaagtggt cgccccggca  5400
cccagcaagt cgagacccga acccgtggtc gtttgcctcc gcggcaaatc cggccagggg  5460
aagagtttcc ttgcgaacgt gctcgcgcaa gcaatctcca cccacttcac cggcagaact  5520
gattcggttt ggtactgccc gcctgaccct gaccacttcg acggttacaa ccagcagacc  5580
gttgtcgtga tggacgattt gggccagaac cccgatggca aggacttcaa gtacttcgcc  5640
cagatggttt cgaccacggg gttcatcccg cccatggcct cgcttgagga caaaggcaag  5700
cctttcaaca gcaaagtcat cattgctacc accaacctgt actcgggttt caccccgaga  5760
acaatggtgt gtcctgacgc gctgaaccgg aggttccact ttgacatcga cgtgagtgcc  5820
aaggacgggt acaaagttaa caacaaattg gacataatca aagctcttga agacacccac  5880
accaacccag tggcgatgtt ccaatacgac tgtgcccttc taaacggtat ggcagttgaa  5940
atgaagagaa tgcaacagga tatgttcaag cctcaaccac ccctccagaa cgtgtaccaa  6000
ctcgttcacg aggtgattga acgggtcgag ctccacgaga aggtgtcgag ccacccgatt  6060
ttcaaacaga tatcaattcc ttcccaaaag tctgtgttgt acttcctcat tgagaaaggc  6120
caacacgaag cagcaattga attctttgag ggaatggtgc atgactccat caaggaagag  6180
```

```
ctccggcccc tcatccaaca gacctcattt gtgaaacgcg cttttaagcg cctgaaggaa  6240
aactttgaga ctgttgccct gtgtttgact cttttggcaa acatagtgat catgatccgc  6300
gagactcgca agagacaaca gatggtggac gatgcagtga atgactacat tgagaaggca  6360
aacatcacca cagatgacaa gactcttgac gaggcggaaa agaaccctct agagaccagc  6420
ggtgccagca ctattggttt cagagagaga actctcccgg ggcacaaggc gagcgatgac  6480
gtgagctccg agcccgccaa acccgtggag gaccgaccac aagctgaagg accttacgag  6540
ggaccggtga agaagcctgt cgctttgaaa gtgaaagcta agaacttgat tgtcactgag  6600
gggccatatg aaggaccagt gaagaaacct gtcgctttga aagtgaaagc aaaagccccg  6660
attgtcactg aaggaccct a cgagggaccg gtgaagaagc ctgtcgcttt gaaagtgaaa  6720
gccaagaact tgattgtcac tgagagtggt gccccaccga ccgacttgca gaagatggtc  6780
atgggcaaca ctaagcctgt tgagctcatc ctcgacggga agacggtagc catctgctgt  6840
gctaccggag tgtttggcac tgcctacctc gtacctcgtc acctcttcgc ggagaagtac  6900
gacaagataa tgttggacgg tagagccatg acagacagtg actacagagt gtttgagttt  6960
gagattaaag taaaaggaca ggacatgctc tcagacgctg cactcatggt gcttcaccgt  7020
gggaaccgcg tgagagacat cacgaaacat tttcgtgaca cagcaagaat gaagaaaggc  7080
acccccgttg tcggtgtgat caacaacgcc gacgttggga gactgatttt ctctggagag  7140
gcccttacct acaaagacat tgtagtgacc atggatggag acaccatgcc gggcctgttt  7200
gcctacagag ccgccaccaa ggctggttac tgcgggggag ccgttctcgc caaggacgga  7260
gccgacacat tcatcgttgg cacccactcc gcaggtggta acggagttgg atactgctcg  7320
tgcgtgtcca ggtccatgct cctgaaaatg aaggcacaca ttgaccctga accacaccac  7380
gaggggttga ttgttgatac cagagatgtg gaagagcgcg tgcatgtcat gcgtaaaacc  7440
aagcttgcac ccaccgtggc acacggtgtg tttaaccctg aatttggtcc cgctgccttg  7500
tccaacaagg acccgcggct gaacgaaggg gttgtcctcg atgaagtcat cttctccaaa  7560
cacaagggag acacgaaaat gtctgaggag gacaaagcgc tgttccgccg ctgcgctgcc  7620
gactacgcgt cgcacttgca cagcgtgctg gggacggcaa atgcccccatt gagcatctat  7680
gaggccatca aaggcgtcga cgggctcgat gccatggagc cggacaccgc gcccggcctc  7740
ccctgggccc tccaggggaa acgccgtggt gcgttgattg acttcgagaa cggcacggtc  7800
ggacccgaag tcgaggctgc cctaaagctc atggagaaaa gagagtacaa atttgcttgc  7860
cagaccttcc tgaaagacga gattcgtccg atggaaaaag tacgtgctgg caagactcgc  7920
attgtcgacg ttttgcccgt ggaacacatt ctttacacca ggatgatgat tggcagattc  7980
tgtgctcaaa tgcacacaaa caatggaccg cagattggct cagcggtcgg ttgcaatcct  8040
gatgttgatt ggcaaagatt tggcacacat tttgctcagt acagaaacgt gtgggatgtg  8100
gactattcgg cctttgatgc taaccactgc agtgacgcaa tgaacatcat gtttgaggag  8160
gtatttcgca cagacttcgg tttccaccca aatgctgagt ggattctgaa gactcttgtg  8220
aacacggagc acgcctatga gaacaaacgt atcactgttg agggcgggat gccgtctggc  8280
tgttccgcga caagcatcat caacacaatt ttgaacaaca tttatgtgct ctacgctctt  8340
cgtagacact atgagggagt tgagctggac acctacacca tgatctccta cggagatgac  8400
atcgtggttg caagtgacta cgatctggat tttgaggctc tcaaaccccca cttcaaatct  8460
cttggtcaaa ccatcactcc agctgacaaa agcgacaaag gttttgttct tggtcactcc  8520
attaccgatg tcactttcct caaaagacac ttccacatgg actatggaac tgggttttac  8580
aaacctgtga tggcctcaaa gaccctcgag gccattctct cctttgcacg ccgtgggacc  8640
atacaggaga agttgatctc cgtggcagga ctcgccgtcc actcaggacc tgacgagtac  8700
cggcgtctct ttgagccctt ccagggtctc ttcgagattc caagctacag atcactttac  8760
ctgcgttggg tgaacgccgt gtgcggtgac gcataatccc tcagatgtca caattggcag  8820
aaagactctg aggcgagcga cgccgtagga gtgaaaagcc cgaaagggct tttcccgctt  8880
cctattccaa aaaaaaaaaa aaaaaactag ttctagagcg gccgccaccg cggtggagct  8940
ccagcttttg ttccctttag tgagggttaa ttgcgcgctt ggcgtaatca tggtcatagc  9000
tgtttcctgt gtgaaattgt tatccgctca caattccaca caacatacga gccggaagca  9060
taaagtgtaa agcctggggt gcctaatgag tgagctaact cacattaatt gcgttgcgct  9120
cactgcccgc tttccagtcg ggaaacctgt cgtgccagct gcattaatga atcggccaac  9180
gcgcggggag aggcggtttg cgtattgggc gctcttccgc ttcctcgctc actgactcgc  9240
tgcgctcggt cgttcggctg cggcgagcgg tatcagctca ctcaaaggcg gtaatacggt  9300
tatccacaga atcaggggat aacgcaggaa agaacatgtg agcaaaaggc cagcaaaagg  9360
ccaggaaccg taaaaaggcc gcgttgctgg cgtttttcca taggctccgc ccccctgacg  9420
agcatcacaa aaatcgacgc tcaagtcaga ggtggcgaaa cccgacagga ctataaagat  9480
accaggcgtt tccccctgga agctccctcg tgcgctctcc tgttccgacc ctgccgctta  9540
ccggatacct gtccgccttt ctcccttcgg gaagcgtggc gctttctcat agctcacgct  9600
gtaggtatct cagttcggtg taggtcgttc gctccaagct gggctgtgtg cacgaacccc  9660
ccgttcagcc cgaccgctgc gccttatccg gtaactatcg tcttgagtcc aacccggtaa  9720
gacacgactt atcgccactg gcagcagcca ctggtaacag gattagcaga gcgaggtatg  9780
taggcggtgc tacagagttc ttgaagtggt ggcctaacta cggctacact agaaggacag  9840
tatttggtat ctgcgctctg ctgaagccag ttaccttcgg aaaaagagtt ggtagctctt  9900
gatccggcaa acaaaccacc gctggtagcg gtggtttttt tgtttgcaag cagcagatta  9960
cgcgcagaaa aaaaggatct caagaagatc ctttgatctt ttctacgggg tctgacgctc  10020
agtggaacga aaactcacgt taagggattt tggtcatgag attatcaaaa aggatcttca  10080
cctagatcct tttaaattaa aaatgaagtt ttaaatcaat ctaaagtata tatgagtaaa  10140
cttggtctga cagttaccaa tgcttaatca gtgaggcacc tatctcagcg atctgtctat  10200
ttcgttcatc catagttgcc tgactccccg tcgtgtagat aactacgata cgggagggct  10260
taccatctgg ccccagtgct gcaatgatac cgcgagaccc acgctcaccg gctccagatt  10320
tatcagcaat aaaccagcca gccggaaggg ccgagcgcag aagtggtcct gcaactttat  10380
ccgcctccat ccagtctatt aattgttgcc gggaagctag agtaagtagt tcgccagtta  10440
atagtttgcg caacgttgtt gccattgcta caggcatcgt ggtgtcacgc tcgtcgtttg  10500
gtatggcttc attcagctcc ggttcccaac gatcaaggcg agttacatga tcccccatgt  10560
tgtgcaaaaa agcggttagc tccttcggtc ctccgatcgt tgtcagaagt aagttggccg  10620
cagtgttatc actcatggtt atggcagcac tgcataattc tcttactgtc atgccatccg  10680
taagatgctt ttctgtgact ggtgagtact caaccaagtc attctgagaa tagtgtatgc  10740
ggcgaccgag ttgctcttgc ccggcgtcaa tacgggataa taccgcgcca catagcagaa  10800
ctttaaaagt gctcatcatt ggaaaacgtt cttcggggcg aaaactctca aggatcttac  10860
cgctgttgag atccagttcg atgtaaccca ctcgtgcacc caactgatct tcagcatctt  10920
```

```
ttactttcac cagcgtttct gggtgagcaa aaacaggaag gcaaaatgcc gcaaaaaagg  10980
gaataagggc gacacggaaa tgttgaatac tcatactctt cctttttcaa tattattgaa  11040
gcatttatca gggttattgt ctcatgagcg gatacatatt tgaatgtatt tagaaaaata  11100
aacaaatagg ggttccgcgc acatttcccc gaaaagtgcc ac                     11142

SEQ ID NO: 12          moltype = DNA  length = 17
FEATURE                Location/Qualifiers
source                 1..17
                       mol_type = other DNA
                       organism = synthetic construct
SEQUENCE: 12
agngcnggna artttga                                                 17

SEQ ID NO: 13          moltype = DNA  length = 18
FEATURE                Location/Qualifiers
source                 1..18
                       mol_type = other DNA
                       organism = synthetic construct
SEQUENCE: 13
catgtcntcc atctggtt                                                18

SEQ ID NO: 14          moltype = DNA  length = 20
FEATURE                Location/Qualifiers
source                 1..20
                       mol_type = other DNA
                       organism = synthetic construct
SEQUENCE: 14
catctgctct ctgggctgtg                                              20

SEQ ID NO: 15          moltype = DNA  length = 20
FEATURE                Location/Qualifiers
source                 1..20
                       mol_type = other DNA
                       organism = synthetic construct
SEQUENCE: 15
tgaggggatc caaagtccct                                              20

SEQ ID NO: 16          moltype = DNA  length = 21
FEATURE                Location/Qualifiers
source                 1..21
                       mol_type = other DNA
                       organism = synthetic construct
SEQUENCE: 16
tgcaaccacc acaattccag a                                            21

SEQ ID NO: 17          moltype = DNA  length = 20
FEATURE                Location/Qualifiers
source                 1..20
                       mol_type = other DNA
                       organism = synthetic construct
SEQUENCE: 17
ggtttcattc cagccagtgc                                              20

SEQ ID NO: 18          moltype = DNA  length = 21
FEATURE                Location/Qualifiers
source                 1..21
                       mol_type = other DNA
                       organism = synthetic construct
SEQUENCE: 18
gccattcaaa ggagcatgga t                                            21

SEQ ID NO: 19          moltype = DNA  length = 20
FEATURE                Location/Qualifiers
source                 1..20
                       mol_type = other DNA
                       organism = synthetic construct
SEQUENCE: 19
ctgatggctt tgcgctggat                                              20

SEQ ID NO: 20          moltype = DNA  length = 22
FEATURE                Location/Qualifiers
source                 1..22
                       mol_type = other DNA
                       organism = synthetic construct
SEQUENCE: 20
agccagtctt cattgttcag gt                                           22

SEQ ID NO: 21          moltype = DNA  length = 21
FEATURE                Location/Qualifiers
```

-continued

```
source                  1..21
                        mol_type = other DNA
                        organism = synthetic construct
SEQUENCE: 21
tcatctcttt ggggccatca g                                             21

SEQ ID NO: 22           moltype = DNA  length = 20
FEATURE                 Location/Qualifiers
source                  1..20
                        mol_type = other DNA
                        organism = synthetic construct
SEQUENCE: 22
ctcgtgaagg cgggaatcat                                               20

SEQ ID NO: 23           moltype = DNA  length = 20
FEATURE                 Location/Qualifiers
source                  1..20
                        mol_type = other DNA
                        organism = synthetic construct
SEQUENCE: 23
ggtgtgctcc ggttcaagat                                               20

SEQ ID NO: 24           moltype = DNA  length = 20
FEATURE                 Location/Qualifiers
source                  1..20
                        mol_type = other DNA
                        organism = synthetic construct
SEQUENCE: 24
ccatatccag tgcggggatg                                               20

SEQ ID NO: 25           moltype = DNA  length = 20
FEATURE                 Location/Qualifiers
source                  1..20
                        mol_type = other DNA
                        organism = synthetic construct
SEQUENCE: 25
aggccttggt ggatcctttg                                               20

SEQ ID NO: 26           moltype = DNA  length = 20
FEATURE                 Location/Qualifiers
source                  1..20
                        mol_type = other DNA
                        organism = synthetic construct
SEQUENCE: 26
tccctcattg caaagcacaa                                               20

SEQ ID NO: 27           moltype = DNA  length = 22
FEATURE                 Location/Qualifiers
source                  1..22
                        mol_type = other DNA
                        organism = synthetic construct
SEQUENCE: 27
gcatctcctc ttgcaagcaa at                                            22

SEQ ID NO: 28           moltype = DNA  length = 20
FEATURE                 Location/Qualifiers
source                  1..20
                        mol_type = other DNA
                        organism = synthetic construct
SEQUENCE: 28
aagctctgga gggagtgcta                                               20

SEQ ID NO: 29           moltype = DNA  length = 23
FEATURE                 Location/Qualifiers
source                  1..23
                        mol_type = other DNA
                        organism = synthetic construct
SEQUENCE: 29
caacagcagt tactgtctca tca                                           23

SEQ ID NO: 30           moltype = DNA  length = 20
FEATURE                 Location/Qualifiers
source                  1..20
                        mol_type = other DNA
                        organism = synthetic construct
SEQUENCE: 30
cggcccagtg aagagtttct                                               20

SEQ ID NO: 31           moltype = DNA  length = 20
```

```
FEATURE                Location/Qualifiers
source                 1..20
                       mol_type = other DNA
                       organism = synthetic construct
SEQUENCE: 31
tgccttcggc attacgtctt                                         20

SEQ ID NO: 32          moltype = DNA  length = 20
FEATURE                Location/Qualifiers
source                 1..20
                       mol_type = other DNA
                       organism = synthetic construct
SEQUENCE: 32
ggctgtcctt tgatgtcacc                                         20

SEQ ID NO: 33          moltype = DNA  length = 18
FEATURE                Location/Qualifiers
source                 1..18
                       mol_type = other DNA
                       organism = synthetic construct
SEQUENCE: 33
ggccagaatt gaacccgt                                           18

SEQ ID NO: 34          moltype = DNA  length = 20
FEATURE                Location/Qualifiers
source                 1..20
                       mol_type = other DNA
                       organism = synthetic construct
SEQUENCE: 34
ctcacctccc aactgatccc                                         20

SEQ ID NO: 35          moltype = DNA  length = 20
FEATURE                Location/Qualifiers
source                 1..20
                       mol_type = other DNA
                       organism = synthetic construct
SEQUENCE: 35
tgtgtccgtg gacgaagttg                                         20

SEQ ID NO: 36          moltype = DNA  length = 20
FEATURE                Location/Qualifiers
source                 1..20
                       mol_type = other DNA
                       organism = synthetic construct
SEQUENCE: 36
ctgcagtcac agaacgagtg                                         20

SEQ ID NO: 37          moltype = DNA  length = 20
FEATURE                Location/Qualifiers
source                 1..20
                       mol_type = other DNA
                       organism = synthetic construct
SEQUENCE: 37
cggcatcaat ctcaggtgcc                                         20

SEQ ID NO: 38          moltype = DNA  length = 20
FEATURE                Location/Qualifiers
source                 1..20
                       mol_type = other DNA
                       organism = synthetic construct
SEQUENCE: 38
gtcatcagca caaatactgc                                         20

SEQ ID NO: 39          moltype = DNA  length = 20
FEATURE                Location/Qualifiers
source                 1..20
                       mol_type = other DNA
                       organism = synthetic construct
SEQUENCE: 39
cacaagtggt gtctgttttc                                         20

SEQ ID NO: 40          moltype = DNA  length = 20
FEATURE                Location/Qualifiers
source                 1..20
                       mol_type = other DNA
                       organism = synthetic construct
SEQUENCE: 40
tcaggcatcg ttcaggtgac                                         20
```

```
SEQ ID NO: 41          moltype = DNA  length = 20
FEATURE                Location/Qualifiers
source                 1..20
                       mol_type = other DNA
                       organism = synthetic construct
SEQUENCE: 41
tgacagccag caccatttca                                        20

SEQ ID NO: 42          moltype = DNA  length = 25
FEATURE                Location/Qualifiers
source                 1..25
                       mol_type = other DNA
                       organism = synthetic construct
SEQUENCE: 42
tgggactgag taacattctc tttgt                                  25

SEQ ID NO: 43          moltype = DNA  length = 20
FEATURE                Location/Qualifiers
source                 1..20
                       mol_type = other DNA
                       organism = synthetic construct
SEQUENCE: 43
ccagctcatc caggcttagg                                        20

SEQ ID NO: 44          moltype = DNA  length = 21
FEATURE                Location/Qualifiers
source                 1..21
                       mol_type = other DNA
                       organism = synthetic construct
SEQUENCE: 44
tgagctattt ctacaccgcc g                                      21

SEQ ID NO: 45          moltype = DNA  length = 19
FEATURE                Location/Qualifiers
source                 1..19
                       mol_type = other DNA
                       organism = synthetic construct
SEQUENCE: 45
tcgtccacgt agccgactt                                         19

SEQ ID NO: 46          moltype = DNA  length = 20
FEATURE                Location/Qualifiers
source                 1..20
                       mol_type = other DNA
                       organism = synthetic construct
SEQUENCE: 46
ctccagtgat gctgggtcag                                        20

SEQ ID NO: 47          moltype = DNA  length = 20
FEATURE                Location/Qualifiers
source                 1..20
                       mol_type = other DNA
                       organism = synthetic construct
SEQUENCE: 47
tgacagagtg cccgttcttc                                        20

SEQ ID NO: 48          moltype = DNA  length = 20
FEATURE                Location/Qualifiers
source                 1..20
                       mol_type = other DNA
                       organism = synthetic construct
SEQUENCE: 48
tgccatgcct acaaagctga                                        20

SEQ ID NO: 49          moltype = DNA  length = 20
FEATURE                Location/Qualifiers
source                 1..20
                       mol_type = other DNA
                       organism = synthetic construct
SEQUENCE: 49
gtagtaacca gggcggcatt                                        20

SEQ ID NO: 50          moltype = DNA  length = 20
FEATURE                Location/Qualifiers
source                 1..20
                       mol_type = other DNA
                       organism = synthetic construct
SEQUENCE: 50
tcaaaggagt tccgggcatc                                        20
```

```
SEQ ID NO: 51          moltype = DNA  length = 20
FEATURE                Location/Qualifiers
source                 1..20
                       mol_type = other DNA
                       organism = synthetic construct
SEQUENCE: 51
ctgaagcagg cgggagtaat                                              20

SEQ ID NO: 52          moltype = DNA  length = 20
FEATURE                Location/Qualifiers
source                 1..20
                       mol_type = other DNA
                       organism = synthetic construct
SEQUENCE: 52
ggatgtgcag cctttgttgt                                              20

SEQ ID NO: 53          moltype = DNA  length = 20
FEATURE                Location/Qualifiers
source                 1..20
                       mol_type = other DNA
                       organism = synthetic construct
SEQUENCE: 53
cagagcgtac caaattgcgg                                              20

SEQ ID NO: 54          moltype = DNA  length = 20
FEATURE                Location/Qualifiers
source                 1..20
                       mol_type = other DNA
                       organism = synthetic construct
SEQUENCE: 54
gagtatgggt ctgcaggcaa                                              20

SEQ ID NO: 55          moltype = DNA  length = 20
FEATURE                Location/Qualifiers
source                 1..20
                       mol_type = other DNA
                       organism = synthetic construct
SEQUENCE: 55
atatgtcgcg gcacagactt                                              20

SEQ ID NO: 56          moltype = DNA  length = 20
FEATURE                Location/Qualifiers
source                 1..20
                       mol_type = other DNA
                       organism = synthetic construct
SEQUENCE: 56
caccatcacc gtgactcgaa                                              20

SEQ ID NO: 57          moltype = DNA  length = 20
FEATURE                Location/Qualifiers
source                 1..20
                       mol_type = other DNA
                       organism = synthetic construct
SEQUENCE: 57
agttcgtgcc gtggaatctt                                              20

SEQ ID NO: 58          moltype = DNA  length = 20
FEATURE                Location/Qualifiers
source                 1..20
                       mol_type = other DNA
                       organism = synthetic construct
SEQUENCE: 58
cccagcgtcg tgattagtga                                              20

SEQ ID NO: 59          moltype = DNA  length = 20
FEATURE                Location/Qualifiers
source                 1..20
                       mol_type = other DNA
                       organism = synthetic construct
SEQUENCE: 59
gccgttcagt cctgtccata                                              20
```